United States Patent
de Min et al.

(10) Patent No.: US 10,556,960 B2
(45) Date of Patent: Feb. 11, 2020

(54) METHODS AND COMPOSITIONS FOR DIAGNOSIS AND TREATMENT OF DISORDERS IN PATIENTS WITH ELEVATED LEVELS OF TLR4 LIGANDS AND OTHER BIOMARKERS

(71) Applicant: NovImmune SA, Geneva (CH)

(72) Inventors: Cristina de Min, Geneva (CH); Limin Shang, Geneva (CH); Emmanuel Monnet, Geneva (CH); Greg Elson, Collonges sous Saleve (FR); Eric Hatterer, Geneva (CH)

(73) Assignee: NovImmune SA, Geneva (CH)

( * ) Notice: Subject to any disclaimer, the term of this patent is extended or adjusted under 35 U.S.C. 154(b) by 0 days.

(21) Appl. No.: 15/632,882

(22) Filed: Jun. 26, 2017

(65) Prior Publication Data
US 2017/0298140 A1   Oct. 19, 2017

Related U.S. Application Data

(62) Division of application No. 14/520,904, filed on Oct. 22, 2014, now Pat. No. 9,688,769.

(60) Provisional application No. 61/894,042, filed on Oct. 22, 2013.

(51) Int. Cl.
| | | |
|---|---|---|
| *A61K 39/395* | (2006.01) | |
| *A61K 38/00* | (2006.01) | |
| *C07K 16/28* | (2006.01) | |
| *G01N 33/564* | (2006.01) | |
| *A61K 39/00* | (2006.01) | |

(52) U.S. Cl.
CPC ....... *C07K 16/2896* (2013.01); *G01N 33/564* (2013.01); *A61K 2039/505* (2013.01); *C07K 2317/76* (2013.01); *G01N 2440/18* (2013.01); *G01N 2800/102* (2013.01)

(58) Field of Classification Search
None
See application file for complete search history.

(56) References Cited

U.S. PATENT DOCUMENTS

| | | | |
|---|---|---|---|
| 7,312,320 | B2 | 12/2007 | Elson |
| 7,674,884 | B2 | 3/2010 | Elson et al. |
| 2006/0165686 | A1 | 7/2006 | Elson et al. |
| 2008/0050366 | A1 | 2/2008 | Elson et al. |
| 2011/0047632 | A1* | 2/2011 | Robinson ........... G01N 33/5082 800/9 |
| 2012/0142098 | A1 | 6/2012 | Elson et al. |
| 2012/0177648 | A1 | 7/2012 | Kosco-Vilbois et al. |

FOREIGN PATENT DOCUMENTS

| | | |
|---|---|---|
| WO | WO 2005/065015 A2 | 7/2005 |
| WO | WO 2006/020930 A2 | 2/2006 |
| WO | WO 2007/022999 A1 | 3/2007 |
| WO | WO 2007/039280 A1 | 4/2007 |
| WO | WO 2007/110678 A2 | 10/2007 |
| WO | WO 2009/101479 A2 | 8/2009 |
| WO | WO 2009/138494 A2 | 11/2009 |
| WO | WO 2012/059598 A2 | 5/2012 |
| WO | WO 2012/096917 A1 | 7/2012 |
| WO | WO 2013/116590 A1 | 8/2013 |
| WO | WO 2015/010791 A2 | 1/2015 |
| WO | WO 2015/059168 A1 | 4/2015 |

OTHER PUBLICATIONS

Takizawa et al. 2006. Ann Rheum Dis. 65:1013-1020 (Year: 2006).*
Sohn et al. 2015. Arth. Rheum. 67:2877-2887 (Year: 2015).*
Abdollahi-Roodsaz, S. et al. (2007) "Inhibition of Toll-like Receptor 4 Breaks the Inflammatory Loop in Autoimmune Destructive Arthritis" *Arth Rheum*, 56:2957-2967.
Abdollahi-Roodsaz et al. (2008) "Stimulation of TLR2 and TLR4 differentially skews the balance of T cells in a mouse model of arthritis" *J Clin Invest* 118:205-216.
Abdulahad, D. A., et al. (2011) "High mobility group box 1 (HMGB1) and anti-HMGB1 antibodies and their relation to disease characteristics in systemic lupus erythematosus" *Arthritis Res Ther*, 13:R71, 9 pages.
Arai, K. et al. (2008) "S100A8 and S100A9 Overexpression Is Associated with Poor Pathological Parameters in Invasive ductal Carcinoma of the Breast" *Curr Cancer Drug Targets*, 8:243-252.
Barochia, A. et al. (2011) "Eritoran tetrasodium (E5564) treatment for sepsis: review of preclinical and clinical studies" *Expert Opin Drug Metab Toxicol*, 7:479-494.
Bouma, G. et al. (2004) "Increased serum levels of MRP-8/14 in type 1 diabetes induce an increased expression of CD11b and an enhanced adhesion of circulating monocytes to fibronectin" *Diabetes*, 53:1979-1986.
Cambridge, G. et al. (May 2013) "Antibodies to citrullinated peptides and risk of coronary heart disease" *Atherosclerosis*, 228(1):243-246.
Chen, J. et al. (2011) "Toll-like receptor 4 regulates early endothelial activation during ischemic acute kidney injury" *Kidney Int*, 79:288-299.
Chen, J. et al. (2011) "Early interleukin 6 production by leukocytes during ischemic acute kidney injury is regulated by TLR4" *Kidney Int*, 80:504-515.
Chen, Y. et al. (2013) "The role of high mobility group box chromosomal protein 1 in rheumatoid arthritis" *Rheumatology*, 52:1739-1747.

(Continued)

*Primary Examiner* — Shulamith H Shafer
(74) *Attorney, Agent, or Firm* — Cooley LLP; Ivor R. Elrifi; Cynthia Kozakiewicz

(57) ABSTRACT

This invention relates generally to methods and compositions for diagnosing and treating disorders associated with elevated levels of Toll-like Receptor 4 (TLR4) ligands and other biomarkers. The invention also relates to methods of treating, delaying the progression of, or otherwise ameliorating a symptom of a disorder associated with elevated levels of TLR4 ligands and other biomarkers using agents that interfere with or otherwise antagonize TLR4 signaling, including neutralizing anti-TLR4 antibodies.

18 Claims, 11 Drawing Sheets

Specification includes a Sequence Listing.

(56) References Cited

OTHER PUBLICATIONS

Dalmady, S. et al. (2013) "Higher levels of autoantibodies targeting mutated citrullinated vimentin in patients with psoriatic arthritis" *Clin Dev Immunol*, 2013:474028, 9 pages.

Frosh, M. et al. (Mar. 2009) "The myeloid-related proteins 8 and 14 complex, a novel ligand of toll-like receptor 4, and interleukin-1beta form a positive feedback mechanism in systemic-onset juvenile idiopathic arthritis" *Arthritis Rheum*, 60:883-891.

Giles, J.T. et al. (2014) "Association of fine specificity and repertoire expansion of anticitrullinated peptide antibodies with rheumatoid arthritis associated interstitial lung disease" *Ann Rheum Dis*, 73:1487-1494.

Gómara, M.J. and Haro, I. (2013) "Citrullinated peptides in the diagnosis of rheumatoid arthritis" *Curr Top Med Chem*, 13(6):743-751.

*Guideline for the use of tocilizumab against rheumatoid arthritis (RA) [Kansetsu riumachi (RA) nitaisuru tocilizumab shiyou guideline]*. Japan College of Rheumatology; Jun. 3, 2013 [online]. Retrieved from the Internet: URL:http://www.ryumachi-jp.com/info/guideline_tcz_130524.pdf. Retrieved on Jun. 28, 2013, 7 pages.

Herrara-Esparza, R. et al. (2013) "Posttranslational Protein Modification in the Salivary Glands of Sjögren's Syndrome Patients" *Autoimmune Dis*, 2013:548064, 7 pages.

Huang, W. et al. (2010) "HMGB1, a potent proinflammatory cytokine in sepsis" *Cytokine*, 51:119-126.

Informed Health Online [Internet]. Cologne, Germany: Institute for Quality and Efficiency in Health Care (IQWiG) (Jan. 22, 2013) "Understanding Urine Tests." PubMed Health, US National Library of Medicine, National Institutes of Health. Retrieved from: http://www.ncbi.nlm.nih.gov/pubmedhealth/PMH0072534/?report=printable, on May 13, 2016; 5 pages.

Ionita, M.G. et al. (2009) "High levels of myeloid-related protein 14 in human atherosclerotic plaques correlate with the characteristics of rupture-prone lesions" *Arterioscler Thromb Vase Biol*, 29:1220-1227, including Supplemental Material, 11 pages.

Jiang, W. and Pisetsky, D.S. (2008) "Expression of high mobility group protein 1 in the sera of patients and mice with systemic lupus erythematosus" *Ann Rheum Dis*, 67:727-728.

Johnson, G.B. et al. (2003) "Activation of Mammalian Toll-like Receptors by Endogenous Agonists" *Crit Rev Immunol*, 23(1&2):15-44.

Jung, D-Y. et al. (2008) "Combined use of myeloid-related protein 8/14 and procalcitonin as diagnostic markers for acute allograft rejection in kidney transplantation recipients" *Transpl Immunol*, 18:338-343.

Kawai, H. et al. (2011) "Prognostic impact of S100A9 overexpression in non-small cell lung cancer" *Tumor Biol*, 32:641-646.

Kuhns, D.B. et al. (Oct. 5, 2007) "Induction of human monocyte interleukin (IL-)8 by fibrinogen through the toll-like receptor pathway" *Inflammation*, 30:178-188.

Kuriyama, N. et al. (2011) "Tenascin-C: A novel mediator of hepatic ischemia and reperfusion injury" *Hepatology*, 54:2125-2136.

LeFranc, M.-P. (2000) "Nomenclature of the Human Immunoglobullin Genes" *Current Protocols in Immunology*. New York: J. Wiley and Sons; Supplement 40, A1.P.1-A.1P.37.

Lehnardt, S. et al. (Jul. 8, 2003) "Activation of innate immunity in the CNS triggers nerodegeneration through a Toll-like receptor 4-dependent pathway" *Proc Natl Acad Sci USA*, 100:8514-8519.

Li, M. et al. (2012) "Toll-like receptor 4 on islet beta cells senses expression changes in high-mobility group box 1 and contributes to the initiation of type 1 diabetes" *Exp Mol Med*, 44(4):260-267.

Loser, K. et al. (2010) "The Toll-like receptor 4 ligands Mrp8 and Mrp14 are crucial in the development of autoreactive CD8+ T cells" *Nat Med*, 16:713-717.

Lucas, K. et al. (Aug. 2013) "Role of the Toll-Like Receptor (TLR) Radial Cycle in Chronic Inflammation: Possible Treatments Targeting the TLR4 Pathway" *Mol Neurobiol*, 48(1):190-204.

Matsuoka, N. et al. (2010) "High-mobility group box 1 is involved in the initial events of early loss of transplanted islets in mice" *J Clin Invest*, 120:735-743.

Midwood, K. et al. (Jul. 2009) "Tenascin-C is an endogenous activator of Toll-like receptor 4 that is essential for maintaining inflammation in arthritic joint disease" *Nat Med*, 15:774-780.

Nicholas, A.P. (Jun. 2013) "Dual immunofluorescence study of citrullinated proteins in Alzheimer diseased frontal cortex" *Neurosci Lett*, 545:107-111.

Nijhuis, C.S.M.O. et al. (Jul. 2003) "Endothelial Cells Are Main Producers of Interleukin 8 through Toll-Like Receptor 2 and 4 Signaling during Bacterial Infection in Leukopenic Cancer Patients" *Clin Diag Lab Immunol*, 10(4):558-563.

Nogueira-Machado, J.A. et al. (2011) "HMGB1, TLR and RAGE: a functional tripod that leads to diabetic inflammation" *Expert Opin Ther Targets*, 15:1023-1035.

Notice of Reasons for Rejection dated Jul. 4, 2018, in Japanese Patent Application No. 2016-525584, filed Oct. 22, 2014, by NovImmune SA; English translation, 8 pages.

Ohashi, K. et al. (2000) "Cutting Edge: Heat Shock Protein 60 Is a Putative Endogenous Ligand of the Toll-Like Receeptor-4 Complex" *J Immunol*, 164:558-561.

Okamura, Y. et al. (Mar. 30, 2001) "The Extra Domain A of Fibronectin Activates Toll-like Receptor 4" *J Biol Chem*, 276(13):10229-10233.

O'Neill, L.A.J. (2003) "Therapeutic targeting of Toll-like receptors for inflammatory and infectious diseases" *Curr Opin Pharmacol*, 3:396-403.

O'Neill, L.A.J. et al.(2009) "Therapeutic Targeting of Toll-Like Receptors for Infectious and Inflammatory Diseases and Cancer" *Pharmacol Rev*, 61(2):177-197.

Opal, S.M. (2007) "The host response to endotoxin, antilipopolysaccharide strategies, and the management of severe sepsis" *Int J Med Microbial*, 297:365-377.

Page, T.H. et al. (2012) "Raised circulating tenascin-C rheumatoid arthritis" *Arthritis Research & Therapy*, 14:R260, 9 pages.

Peng, W.H. et al. (2011) "Increased serum myeloid-related protein 8/14 level is associated with atherosclerosis in type 2 diabetic patients" *Cardiovasc Diabetol*, 10:41, 7 pages.

Pivarcsi, A. et al. (2003) "Expression and function of Toll-like receptors 2 and 4 in human keratinocytes" *Intl Immunol*, 15(6):721-730.

Quirke, A-M. et al.(Jun. 2011) "Citrullination of autoantigens: Upstream of TNFα in the pathogenesis of rheumatoid arthritis" *FEBS Lett*, 585(23):3681-3688.

"Rheumatoid Arthritis" in *Pharmacology Glossary* [*Yakugaku Yougo Kaisetsu*]. The Pharmacological Society of Japan, 2005-2008 [online]. Retrieved from the Internet: URL:http://www.pharm.or.jp/dictionary/wiki.cgi?%E9%96%A2%E7%AF%80%E3%83%AA%E3%82%A6%E3%83%9E%E3%83%81. Retrieved on Jun. 28, 2018, 2 pages (Japanese).

Roelofs, M.F. et al.(2006) "Identification of Small Heat Shock Protein BS (HSP22) as a Novel TLR4 Ligand and Potential Involvement in the Pathogenesis of Rheumatoid Arthritis" *J Immunol*, 176:7021-7027.

Sabroe, I. et al.(2003). "Toll-Like Receptors in Health and Disease: Complex Questions Remain" *J Immunol*, 171:1630-1635.

Schierbeck, H. et al.(Sep.-Oct. 2011) "Monoclonal anti-HMGB1 antibody protection in two experimental arthritis models" *Mol Med*, 17(9-10):1039-1044.

Schulze Zur Wiesch, A. et al. (2004) "Myeloid related proteins MRP8/MRP14 may predict disease flares in juvenile idiopathic arthritis" *Clin Exp Rheumatol*, 22:368-373.

Shimazu, R. et al. (1999) "MD-2, a Molecule that Confers Lipopolysaccharide Responsiveness on Toll-like Receptor 4" *J Exp Med*, 189:1777-1782.

Smiley, S.T. et al. (2001) "Fibrinogen stimulates macrophage chemokine secretion through toll-like receptor 4" *J Immunol*, 167:2887-2894.

Sokolove, J. et al. (Jan. 2011) "Immune Complexes Containing Citrullinated Fibrinogen Costimulate Macrophages via Toll-like Receptor 4 and Fcγ Receptor" *Arthritis & Rheumatism*, 63(1):53-62.

(56) References Cited

OTHER PUBLICATIONS

Soyfoo, M.S. et al. (2009) "Phagocyte-specific S100A8/A9 protein levels during disease exacerbations and infections in systemic lupus erythematosus" *J Rheumatol*, 36(10):2190-2194.

Sunahori, K. et al. (2006) "The S100A8/A9 heterodimer amplifies proinflammatory cytokine production by macrophages via activation of nuclear factor kappa B and p38 mitogen-activated protein kinase in rheumatoid arthritis" *Arthritis Res Ther*, 8:R69, 12 pages.

Szekaneez, Z. et al. (2008) "Anti-Citrullinated Protein Antibodies in Rheumatoid Arthritis: As Good as it Gets'?" *Clinic. Rev. Allerg Immunol*, 34:26-31.

Taki, J. et al. (Jul. 2010) "Dynamic expression of tenascin-C after myocardial ischemia and reperfusion: assessment by $^{125}$I-anti-tenascin-C antibody imaging" *J Nucl Med*, 51(7):1116-1122.

Urbonaviciute, V. and Voll, R.E. (2011) "High-mobility group box 1 represents a potential marker of disease activity and novel therapeutic target in systemic lupus erythematosus" *J Intern Med*, 270:309-318.

Van Den Berg, W. et al. (2007) "Amplifying elements of arthritis and joint destruction" *Ann Rheum Dis*, 66 (Suppl III):iii45-iii48.

Van Lent, P.L. et al. (Nov. 2010) "S100A8 causes a shift toward expression of activatory Fcgamma receptors on macrophages via toll-like receptor 4 and regulates Fcgamma receptor expression in synovium during chronic experimental arthritis" *Arthritis Rheum*, 62(11):3353-3364.

Van Zoelen, M.A. et al. (2009) "Expression and role of myeloid-related protein-14 in clinical and experimental sepsis" *Am J Respir Crit Care Med*, 180:1098-1106.

Wähämaa, H. et al. (2011) "High mobility group box protein 1 in complex with lipopolysaccharide or IL-1 promotes an increased inflammatory phenotype in synovial fibroblasts" *Arthritis Res Ther*, 13:R136, 12 pages.

Wu, H. et al. (2010) "HMGB1 contributes to kidney ischemia reperfusion injury" *J Am Soc Nephrol*, 21:1878-1890.

Zreiqat, H. et al. (2010) "S100A8 and S100A9 in experimental osteoarthritis" *Arthritis Res Ther*, 12:R16, 13 pages.

Hasegawa, M. et al. (May 2007) "Expression of Large Tenascin-C Splice Variants in Synovial Fluid of Patients with Rheumatoid Arthritis" *J Orthopaedic Research*, 25:563-568.

Zhao, X. et al. (2008) "Circulating immune complexes contain citrullinated fibrinogen in rheumatoid arthritis" *Arth Res Ther*, 10(4):R94, 13 pages.

Ehrchen, J. M. et al., "The endogenous Toll-like receptor 4 agonist S100A8/S10A9 (calprotectin) asinnate amplifier of infection, autoimmunity, and cancer," Journal of Leukocyte Biology, 86:557-566 (2009).

* cited by examiner

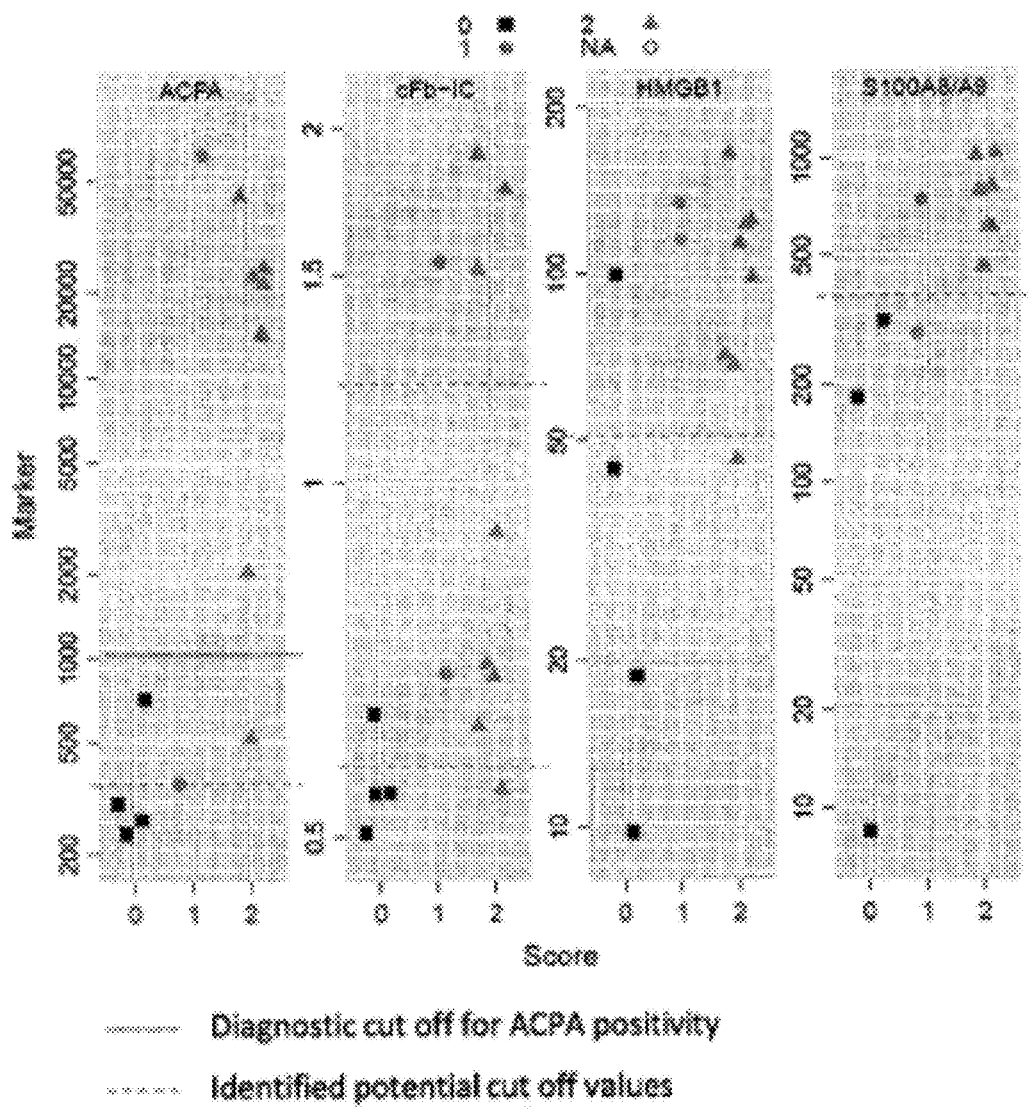

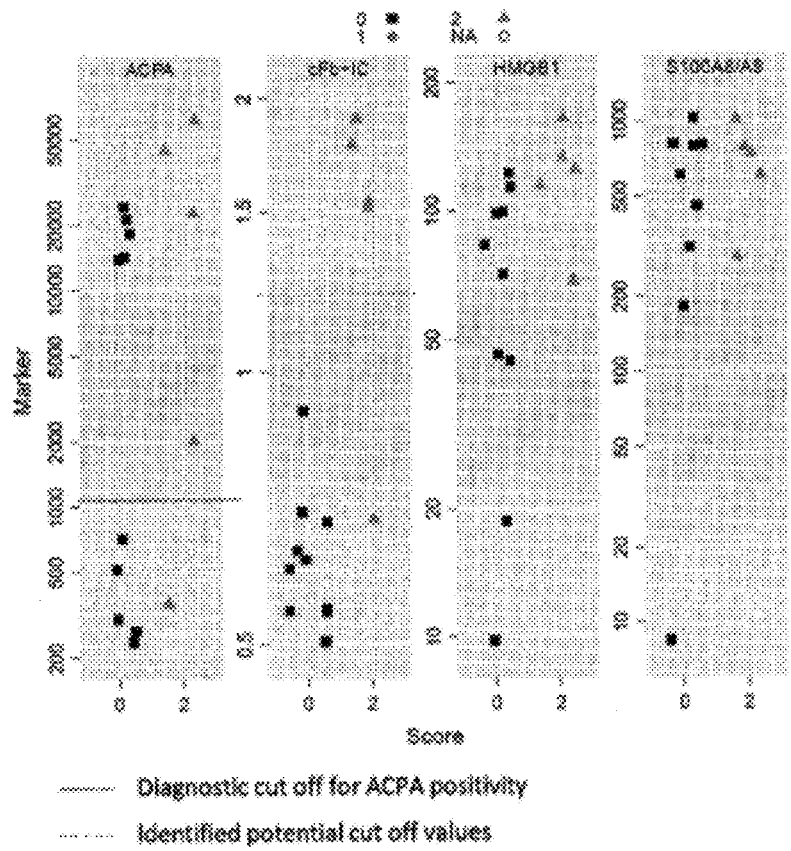

METHODS AND COMPOSITIONS FOR DIAGNOSIS AND TREATMENT OF DISORDERS IN PATIENTS WITH ELEVATED LEVELS OF TLR4 LIGANDS AND OTHER BIOMARKERS

RELATED APPLICATIONS

This application is a divisional of U.S. application Ser. No. 14/520,904, filed Oct. 22, 2014, which claims the benefit of U.S. Provisional Application No. 61/894,042, filed Oct. 22, 2013. The contents of each of which are hereby incorporated by reference in their entirety.

INCORPORATION OF SEQUENCE LISTING

The contents of the text file named "NOVI032D01US_SeqList", which was created on Jun. 23, 2017 and is 115 KB in size, are hereby incorporated by reference in their entirety.

FIELD OF THE INVENTION

This invention relates generally to methods and compositions for diagnosing and treating disorders associated with elevated levels of Toll-like Receptor 4 (TLR4) ligands and other biomarkers. The invention also relates to methods of treating, delaying the progression of, or otherwise ameliorating a symptom of a disorder in patients with elevated levels of TLR4 ligands and other biomarkers using agents that interfere with or otherwise antagonize TLR-4 signaling, including neutralizing anti-TLR4 antibodies.

BACKGROUND OF THE INVENTION

Toll receptors, first discovered in *Drosophila*, are type I transmembrane protein having leucine-rich repeats (LRRs) in the extracellular portion of the protein, and one or two cysteine-rich domains. The mammalian homologs of the *Drosophila* Toll receptors are known as "Toll-like receptors" (TLRs). TLRs play a role in innate immunity by recognizing microbial particles and activating immune cells against the source of these microbial particles. In humans, eleven Toll-like receptors, TLRs 1-11, have been identified and are characterized by the homology of their intracellular domains to that of the IL-1 receptor, and by the presence of extracellular leucine-rich repeats. The different types of TLRs are activated by different types of microbial particles. For example, TLR4 is primarily activated by lipopolysaccharide (LPS). TLR4 has been shown to associate with an accessory protein, myeloid differentiation protein-2 (MD-2). This protein has been found to interact directly with TLR4, and MD-2 has the ability to enable post-translational modifications of TLR4, as well as facilitate its transport to the cell surface. TLR4 and MD-2 form a complex on the cell surface.

TLR4 has been implicated in a number of disorders; and anti-TLR4 agents are being developed as therapeutic agents. Not all patients respond to current standard of care therapies. Accordingly, there exists a need for compositions and methods for use in identifying patients that are likely candidates for a particular treatment, for example, treatment with a particular anti-TLR4 therapy.

SUMMARY OF THE INVENTION

The compositions and methods provided herein are useful in identifying or otherwise refining a patient population suffering from a disorder, where the patient has an elevated level of one or more TLR4 ligands or other TLR4-related biomarkers. These patients are identified as suitable candidates for treatment with an agent (e.g., antibodies or other polypeptide-based therapeutics, peptide-based therapeutics, small molecule inhibitors, nucleic acid-based therapeutics and derivatives thereof) that interferes with or otherwise antagonizes TLR4 signaling and neutralizes at least one biological activity of TLR4, alone or in the context of the accessory protein MD-2 as the TLR4/MD-2 complex.

In some patients suffering from or suspected of suffering from a disorder, fluids and other biological samples contain elevated levels of TLR4 ligands and other biomarkers. These TLR4 ligands and other biomarkers stimulate cells to produce pro-inflammatory cytokines. However, use of an anti-TLR4 antagonist that interferes with, inhibits, reduces or otherwise antagonizes TLR4 signaling, e.g., a neutralizing anti-TLR4 antibody or other polypeptide-based therapeutic, a peptide-based therapeutic, a small molecule inhibitor, a nucleic acid-based therapeutic and derivatives thereof, is shown herein to block this stimulation in samples from patients exhibiting an elevated level of expression for one or more TLR4 ligands and/or other biomarkers. Thus, the compositions and methods are useful in treating, delaying the progression of or otherwise ameliorating a symptom of a disorder that is dependent on, driven by, associated with, or otherwise impacted by TLR4 signaling, aberrant, e.g., elevated, TLR4 ligand expression and/or activity, aberrant pro-inflammatory cytokine production and/or combinations thereof, by administering an anti-TLR4 antagonist, e.g., a neutralizing anti-TLR4 antibody or other polypeptide-based therapeutic, a peptide-based therapeutic, a small molecule inhibitor, a nucleic acid-based therapeutic and derivatives thereof, to patients exhibiting an elevated level of expression for one or more TLR4 ligands and/or other biomarkers. Patients that are likely suitable candidates for treatment with the anti-TLR4 antagonist, e.g., neutralizing anti-TLR4 antibody such as those described herein, are identified by detecting the level of one or more TLR4 ligands or other biomarkers. In some embodiments, patients that do not have elevated levels of one or more TLR4 ligands or other biomarkers may still be treated with an anti-TLR4 antagonist, including any of the neutralizing anti-TLR4 antibodies described herein or other polypeptide-based therapeutic, a peptide-based therapeutic, a small molecule inhibitor, a nucleic acid-based therapeutic and derivatives thereof.

Suitable TLR4 ligands and other biomarkers for use in these methods of identifying likely candidates include anti-citrullinated protein antibodies (ACPA), citrullinated proteins, citrullinated proteins in an immune complex, e.g., citrullinated fibrinogen (cFb) in an immune complex with an IgG protein (cFb-IC) or an IgE protein, HMGB1, S100A8/A9, Tenascin C, LPS, heat shock proteins (HSPs), fibronectin, hyaluronan, Der P2, Respiratory Syncytial Virus F (RSV) F protein, Surfactant A, Coxsakievirus B4 (CSV B4), CXCL10, Resistin, Fetuin A, Saturated Fatty Acid (SFA), Biglycan, Modified Low-Density Lipoprotein (mLDL), advanced glycation end products (AGE) and combinations thereof. In some embodiments, the citrullinated protein is citrullinated fibrinogen, citrullinated fibrin, citrullinated vimentin, a citrullinated histone (e.g., citrullinated histone 2b), citrullinated enolase or a citrullinated chemokine, (e.g. citrullinated CXCL10). In some embodiments, a combination of TLR4 ligand and/or other biomarker is detected, for example, at least two TLR4 ligands and/or other biomarkers are detected, at least three TLR4 ligands and/or other biomarkers are detected, at least four TLR4 ligands and/or other biomarkers are detected, at least five TLR4 ligands and/or other biomarkers are detected, at least six TLR4 ligands and/or other biomarkers are detected, at least eight TLR4 ligands and/or other biomarkers are detected, at least nine TLR4 ligands and/or other biomarkers are detected, or at least ten or more TLR4 ligands and/or other biomarkers are detected.

In some embodiments, the TLR4 ligand or other biomarker is S100A8/A9. In some embodiments, the TLR4 ligand or other biomarker is cFb-IC. In some embodiments, the TLR4 ligand or other biomarker is ACPA. In some embodiments, the TLR4 ligand or other biomarker is HMGB1. In some embodiments, the TLR4 ligand or other biomarker is a combination of S100A8/A9 and HMGB1. In some embodiments, the TLR4 ligand or other biomarker is a combination of S100A8/A9 and cFb-IC. In some embodiments, the TLR4 ligand or other biomarker is a combination of S100A8/A9 and ACPA. In some embodiments, the TLR4 ligand or other biomarker is a combination of ACPA and cFb-IC. In some embodiments, the TLR4 ligand or other biomarker is a combination of ACPA and HMGB1. In some embodiments, the TLR4 ligand or other biomarker is a combination of HMGB1 and cFb-IC. In some embodiments, the TLR4 ligand or other biomarker is a combination of S100A8/A9, ACPA and HMGB1. In some embodiments, the TLR4 ligand or other biomarker is a combination of S100A8/A9, ACPA and cFb-IC. In some embodiments, the TLR4 ligand or other biomarker is a combination of S100A8/A9, cFb-IC and HMGB1. In some embodiments, the TLR4 ligand or other biomarker is a combination of ACPA, HMGB1 and cFb-IC. In some embodiments, the TLR4 ligand or other biomarker is a combination of S100A8/A9, cFb-IC, ACPA and HMGB1.

In some embodiments, the TLR4 ligand or other biomarker is a predictor of monocyte response to exposure to an anti-TLR4 agent, e.g., an anti-TLR4 mAb such as NI-0101. In some embodiments, the predictor of monocyte response to anti-TLR4 treatment is S100A8/A9. In some embodiments, the predictor of monocyte response to anti-TLR4 treatment is ACPA. In some embodiments, the predictor of monocyte response to anti-TLR4 treatment is HMGB1. In some embodiments, the predictor of monocyte response to anti-TLR4 treatment is cFb-IC.

In some embodiments, the TLR4 ligand or other biomarker is a predictor of fibroblast response to exposure to an anti-TLR4 agent, e.g., an anti-TLR4 mAb such as NI-0101. In some embodiments, the predictor of fibroblast response to anti-TLR4 treatment is cFb-IC.

In some embodiments, the TLR4 ligand or other biomarker is a predictor of monocyte and fibroblast response to exposure to an anti-TLR4 agent, e.g., an anti-TLR4 mAb such as NI-0101. In some embodiments, the predictor of monocyte and fibroblast response is ACPA. In some embodiments, the predictor of monocyte and fibroblast response is cFb-IC. In some embodiments, the predictor of monocyte and fibroblast response is S100A8/A9. In some embodiments, the predictor of monocyte and fibroblast response is HMGB1. In some embodiments, the predictor of monocyte and fibroblast response is a combination of S100A8/A9 and HMGB1. In some embodiments, the predictor of monocyte and fibroblast response is a combination of S100A8/A9 and cFb-IC. In some embodiments, the predictor of monocyte and fibroblast response is a combination of S100A8/A9 and ACPA. In some embodiments, the predictor of monocyte and fibroblast response is a combination of ACPA and cFb-IC. In some embodiments, the predictor of monocyte and fibroblast response is a combination of ACPA and HMGB1. In some embodiments, the predictor of monocyte and fibroblast response is a combination of HMGB1 and cFb-IC. In some embodiments, the predictor of monocyte and fibroblast response is a combination of S100A8/A9, ACPA and HMGB1. In some embodiments, the predictor of monocyte and fibroblast response is a combination of S100A8/A9, ACPA and cFb-IC. In some embodiments, the predictor of monocyte and fibroblast response is a combination of S100A8/A9, cFb-IC and HMGB1. In some embodiments, the predictor of monocyte and fibroblast response is a combination of ACPA, HMGB1 and cFb-IC. In some embodiments, the predictor of monocyte and fibroblast response is a combination of S100A8/A9, cFb-IC, ACPA and HMGB1.

Patients with elevated levels of one or more of these markers are identified as suitable candidates for therapy with one or more anti-TLR4 antagonists, e.g., a neutralizing anti-TLR4 antibody described herein. As used herein, the phrase "elevated level of expression" refers to a level of expression that is greater than a baseline level of expression of the TLR4 ligand or other biomarker in a sample from a patient that is not suffering from or suspected of suffering from a disorder or other control sample. By way of non-limiting example, baseline levels of several TLR4 ligands are shown in FIGS. 2A-2E. For example, a baseline level of ACPA expression is less than about 2000 Ul/ml, e.g., less than about 1500 Ul/ml, less than about 1000 Ul/ml, and/or less than about 750 Ul/ml (FIG. 2A, Table 1). A baseline level of cFb-IC is, for example, an OD 450 nM reading of 1.5 or less when measured using a standard ELISA (coat plate with 50 μL/well of 1 μg/mL of mouse anti-human citrullinated fibrinogen (cFb) antibody, 3D1, (anti-cFb, clone 3D1, # AM32004PU-N, Acris) in PBS; add 50 μL of 1/10 diluted (in PBS) synovial fluid sample from RA patients; detect binding with anti-human-IgG-Fc-HRP (SIGMA, #A0170), 1/10000 in PBS, 50 μL/well in all wells followed by 50 μL/well of TMB), e.g., an OD 450 nM reading of 1.0 or less, and/or an OD 450 nM reading of 0.5 or less (FIG. 2B, Table 1). A baseline level of HMGB1 is less than about 100 ng/ml, e.g., less than about 75 ng/ml, less than about 50 ng/ml, and/or less than about 25 ng/ml (FIG. 2C, Table 1). A baseline level of S100A8/A9 is less than about 500 ng/ml, e.g., less than about 400 ng/ml, less than about 300 ng/ml, less than about 200 ng/ml, and/or less than about 100 ng/ml (FIG. 2D, Table 1). A baseline level of Tenascin C is less than about 100 ng/ml, e.g., less than about 75 ng/ml, less than about 50 ng/ml, less than about 25 ng/ml, and/or less than about 10 ng/ml (FIG. 2C, Table 1). In some embodiments, the elevated level of expression of the TLR4 ligand or other biomarker is a significant level of elevation.

Patients with certain detected levels of one or more of these markers are identified as "responders" or "non-responders" based on the detected level of the marker as compared to a cutoff level for each marker. By way of non-limiting example, cutoff levels of several TLR4 ligands are shown in Example 5. For example, patients with a detected level of S100A8/A9 of greater than or equal to 387 ng/ml for the monocyte response score in synovial fluid samples are identified as "responders" to treatment with an anti-TLR4 therapy, such as a neutralizing anti-TLR4 antibody, e.g., NI-0101, while patients with a detected level of S100A8/A9 of less than 387 ng/ml for the monocyte response score in synovial fluid samples are identified as "non-responders" to treatment with an anti-TLR4 therapy. Patients with a detected level of ACPA of greater than or equal to 1000 Ul/ml for the monocyte response score in synovial fluid samples are identified as "responders" to treatment with an anti-TLR4 therapy, such as a neutralizing anti-TLR4 antibody, e.g., NI-0101, while patients with a detected level of ACPA of less than 1000 Ul/ml for the monocyte response score in synovial fluid samples are identified as "non-responders" to treatment with an anti-TLR4 therapy. Patients with a detected level of HMGB1 of greater than or equal to 50 ng/ml for the monocyte response score in synovial fluid samples are identified as "responders" to treatment with an anti-TLR4 therapy, such as a neutralizing anti-TLR4 antibody, e.g., NI-0101, while patients with a detected level of HMGB1 of less than 50 ng/ml for the monocyte response score in synovial fluid samples are identified as "non-responders" to treatment with an anti-TLR4 therapy. Patients with a detected cFb-IC OD 450 nm reading greater than or equal to 1.2 for the monocyte response score in synovial fluid samples are identified as "responders" to treatment with an anti-TLR4 therapy such as a neutralizing anti-TLR4 antibody, e.g., NI-0101, while patients with a detected cFb-IC OD 450 nm reading less than 1.2 for the monocyte response score in synovial fluid samples are identified as "non-responders" to treatment with an anti-TLR4 therapy.

Patients with a detected cFb-IC OD 450 nm reading greater than or equal to 1.2 for the fibroblast response score in synovial fluid samples are identified as "responders" to treatment with an anti-TLR4 therapy such as a neutralizing anti-TLR4 antibody, e.g., NI-0101, while patients with a detected cFb-IC OD 450 nm reading less than 1.2 for the fibroblast response score in synovial fluid samples are identified as "non-responders" to treatment with an anti-TLR4 therapy. Patients with a detected level of ACPA of greater than or equal to 1000 Ul/ml for the fibroblast response score in synovial fluid samples are identified as "responders" to treatment with an anti-TLR4 therapy, such as a neutralizing anti-TLR4 antibody, e.g., NI-0101, while patients with a detected level of ACPA of less than 1000 Ul/ml for the fibroblast response score in synovial fluid samples are identified as "non-responders" to treatment with an anti-TLR4 therapy.

Patients with a detected cFb-IC OD 450 nm reading greater than or equal to 0.55 for the combined monocyte and fibroblast response score (cMFRS) in synovial fluid samples are identified as "responders" to treatment with an anti-TLR4 therapy such as a neutralizing anti-TLR4 antibody, e.g., NI-0101, while patients with a detected cFb-IC OD 450 nm reading less than 0.55 for the cMFRS in synovial fluid samples are identified as "non-responders" to treatment with an anti-TLR4 therapy. Patients with a detected level of ACPA of greater than or equal to 330 Ul/ml for the cMFRS in synovial fluid samples are identified as "responders" to treatment with an anti-TLR4 therapy, such as a neutralizing anti-TLR4 antibody, e.g., NI-0101, while patients with a detected level of ACPA of less than 330 Ul/ml for the cMFRS in synovial fluid samples are identified as "non-responders" to treatment with an anti-TLR4 therapy. Patients with a detected level of HMGB1 of greater than or equal to 45 ng/ml for the cMFRS in synovial fluid samples are identified as "responders" to treatment with an anti-TLR4 therapy, such as a neutralizing anti-TLR4 antibody, e.g., NI-0101, while patients with a detected level of HMGB1 of less than 45 ng/ml for the cMFRS in synovial fluid samples are identified as "non-responders" to treatment with an anti-TLR4 therapy. Patients with a detected level of S1008A8/A9 of greater than or equal to 387 ng/ml for the cMFRS in synovial fluid samples are identified as "responders" to treatment with an anti-TLR4 therapy, such as a neutralizing anti-TLR4 antibody, e.g., NI-0101, while patients with a detected level of S1008A8/A9 of less than 387 ng/ml for the cMFRS in synovial fluid samples are identified as "non-responders" to treatment with an anti-TLR4 therapy.

Patients with a detected cFb-IC OD 450 nm reading greater than or equal to 0.55 for the combined monocyte and fibroblast response score (cMFRS) in synovial fluid samples and a detected level of S1008A8/A9 of greater than or equal to 387 ng/ml for the cMFRS in synovial fluid samples are identified as "responders" to treatment with an anti-TLR4 therapy such as a neutralizing anti-TLR4 antibody, e.g., NI-0101, while patients with a detected cFb-IC OD 450 nm reading less than 0.55 for the cMFRS in synovial fluid samples a detected level of Si008A8/A9 less than 387 ng/ml for the cMFRS in synovial fluid samples are identified as "non-responders" to treatment with an anti-TLR4 therapy.

The sample is, for example, blood or a blood component, e.g., serum, plasma. In some embodiments, the sample is urine. In some embodiments, the fluid is synovial fluid. In some embodiments, the fluid is bronchial alveolar fluid. In some embodiments, the fluid is cerebrospinal fluid. In some embodiments, the fluid is saliva.

In addition to detecting the level of one or more of these TLR4 ligands and/or biomarkers, suitable patients for treatment with an anti-TLR4 antagonist can also be identified by evaluating any of a number of additional biological and clinical parameters that will improve the sensitivity and specificity of the biomarker for identifying or otherwise refining the patient population. Alternatively, these additional biological and clinical parameters can be used alone as a means for identifying patients that are suitable candidates for treatment with an anti-TLR4 antagonist or other suitable therapy. These biological and clinical parameters include, by way of non-limiting example, any of the following: rheumatoid factor levels, C-reactive protein (CRP) levels, blood cells count, presence of TLR4 receptor on blood cell subpopulations, TLR4 polymorphisms, human leukocyte antigen (HLA) polymorphisms, peptidyl arginine deiminase (PAD) enzymes and PAD enzyme polymorphisms, Fcγ Receptor IIa (FcγIIa) polymorphisms, MD-2 levels, soluble CD14 levels, baseline patient demographic data (e.g., body mass index (BMI), sex, age, etc.) and/or patient medical history (e.g., disability assessment schedule (DAS 28) at diagnosis, DAS28 at treatment initiation, duration of disease, age at disease onset, response to prior treatments based on DAS28, American College of Rheumatology (ACR) and/or European League Against Rheumatism (EULAR) response criteria, etc.).

Disorders that are useful with the compositions and methods of the invention include any disorder where aberrant, e.g., elevated, TLR4 expression and/or activity, with aberrant TLR4/MD-2 activation and/or aberrant TLR4 ligand activity (e.g., aberrant stimulation of pro-inflammatory cytokine production such as aberrant stimulation of IL-6, TNFα and/or IL-8 production). For example, some TLR4 ligands are believed to be associated with various disorders. By way of non-limiting example, LPS is known to be associated with disorders such as sepsis, acute lung injury, and/or RA; Tenascin C is known to be associated with disorders such as arthritis, hepatic and/or cardiac ischemial reperfusion; HMGB1 is known to be associated with disorders such as RA, Osteoarthritis (OA), ischemia/reperfusion, Type 1 diabetes, islet transplantation, lupus and/or sepsis; S100A8/A9 is known to be associated with disorders such as RA, OA, juvenile idiopathic arthritis (JIA), diabetes, transplant rejection, lupus, atherosclerosis, sepsis and/or cancer; citrullinated fibrinogen is known to be associated with disorders such as RA and atherosclerosis; ACPA is known to be associated with disorders such as RA, psoriatic arthritis, systemic lupus erythematosus (SLE), Sjogren's syndrome, Alzheimer disease and/or atherosclerosis.

By way of non-limiting examples, the methods and compositions provided herein are suitable for diagnosing and/or treating disorders such as autoimmune and/or inflammatory disorders. Suitable autoimmune and/or inflammatory disorders include, by way of non-limiting example, autoimmune and/or inflammatory disorders associated with aberrant TLR4 signaling, autoimmune and/or inflammatory disorders associated with aberrant, e.g., elevated, TLR4 ligand expression and/or activity, autoimmune and/or inflammatory disorders associated with aberrant pro-inflammatory cytokine production, and combinations thereof.

In some embodiments, the disorder is an arthritis condition, including by way of non-limiting example, RA, Osteoarthritis (OA), psoriatic arthritis or juvenile idiopathic arthritis (JIA). In some embodiments, the disorder is rheumatoid arthritis (RA). In some embodiments, the disorder is cancer. In some embodiments, the disorder is inflammatory bowel disease (IBD). In some embodiments, the disorder is atherosclerosis. In some embodiments, the disorder is associated with ischemial reperfusion, including by way of non-limiting example, hepatic and/or cardiac ischemia/reperfusion. In some embodiments, the disorder is sepsis. In some embodiments, the disorder is acute lung injury. In some embodiments, the disorder is Type 1 diabetes. In some embodiments, the disorder is associated with islet transplantation. In some embodiments, the disorder is lupus. In some embodiments, the disorder is associated with transplant rejection or other disorder associated with cell, tissue and/or organ transplant. In some embodiments, the disorder is systemic lupus erythematosus (SLE). In some embodiments, the disorder is Sjogren's syndrome. In some embodiments, the disorder is Alzheimer's disease.

Once patients are identified as having an elevated level of one or more TLR4 ligands or other biomarkers, they are then treated with an anti TLR4 antagonist. For example, the anti TLR4 antagonist is a neutralizing anti TLR4 antibody or an immunologically active (e.g., antigen binding) fragment thereof. Suitable neutralizing antiTLR4 antibodies include any of the anti-TLR4 antibodies described herein and other antibodies with increased affinity for Fc receptor (FcR) and/or increased avidity for cell surface binding through interaction with FcR.

In some embodiments, the antibody or immunologically active fragment thereof that binds TLR4 comprises a variable heavy chain complementarity determining region 1 (VH CDR1) comprising an amino acid sequence at least 90%, 92%, 95%, 96%, 97% 98%, 99% or more identical to the amino acid sequence of GGYSWH (SEQ ID NO: 1); a VH CDR2 region comprising an amino acid sequence at least 90%, 92%, 95%, 96%, 97% 98%, 99% or more identical to the amino acid sequence of YIHYSGYTDFNPSLKT (SEQ ID NO: 2); and a VH CDR3 region comprising an amino acid sequence at least 90%, 92%, 95%, 96%, 97% 98%, 99% or more identical to the amino acid sequence of KDPSDAFPY (SEQ ID NO: 3); a variable light chain complementarity determining region 1 (VL CDR1) region comprising an amino acid sequence at least 90%, 92%, 95%, 96%, 97% 98%, 99% or more identical to the amino acid sequence of RASQSISDHLH (SEQ ID NO: 4); a VL CDR2 region comprising an amino acid sequence at least 90%, 92%, 95%, 96%, 97% 98%, 99% or more identical to the amino acid sequence of YASHAIS (SEQ ID NO: 5); and a VL CDR3 region comprising an amino acid sequence at least 90%, 92%, 95%, 96%, 97% 98%, 99% or more identical to the amino acid sequence of QQGHSFPLT (SEQ ID NO: 6). In some embodiments, the antibody or immunologically active fragment thereof that binds TLR4 further comprises an amino acid sequence at least 90%, 92%, 95%, 96%, 97% 98%, 99% or more identical to the heavy chain variable amino acid sequence QVQLQESGPGLVKPSDTLSLTCAVSGYSITGGYSWHWIRQPPGKGLEWMGYIHYSGYT DFNPSLKTRITISRDTSKNQFSLKLSSVTAVDTAVYYCARKDPSDAFPYWGQGTLVTVSS (SEQ ID NO: 7) and an amino acid sequence at least 90%, 92%, 95%, 96%, 97% 98%, 99% or more identical to the light chain variable amino acid sequence EIVLTQSPDFQSVTPKEKVTITCRASQSISDHLHWYQQKPDQSPKLLIKYASHAISGVPSR FSGSGSGTDFTLTINSLEAEDAATYYCQQGHSFPLTFGGGTKVEIK (SEQ ID NO: 8). In some embodiments, the antibody or immunologically active fragment thereof that binds TLR4 further comprises an amino acid sequence at least 90%, 92%, 95%, 96%, 97%, 98%, 99% or more identical to the heavy chain amino acid sequence MGWSWIFLFLLSGTAGVHCQVQLQESGPGLVKPSDTLSLTCAVSGYSITGGYSWHWIR QPPGKGLEWMGYIHYSGYTDFNPSLKTRITISRDTSKNQFSLKLSSVTAVDTAVYYCAR KDPSDAFPYWGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTKVDKRVE PKSCDKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSSKAFPAPIE KTISKAKGQPREPQVYTLPPSREEMTKNQVSLTCLVKGFYPSDIAVEWESNGQPENNYK TTPPVLDSDGSFFLYSKLTVDKSRWQQGNVFSCSVMHEALHNHYTQKSLSLSPGK (SEQ ID NO: 9) and an amino acid sequence at least 90%, 92%, 95%, 96%, 97% 98%, 99% or more identical to the light chain amino acid sequence MEWSWVFLFFLSVTTGVHSEIVLTQSPDF QSVTPKEKVTITCRASQSISDHLHWYQQKPDQSPKLLIKYASHAISGVPSRFSGSGSGTDF TLTINSLEAEDAATYYCQQGHSFPLTFGGGTKVEIKRTVAAPSVFIFPPSDEQLKSGTASV VCLLNNFYPREAKVQWKVDNALQSGNSQESVTEQDSKDSTYSLSSTLTLSKADYEKHK VYACEVTHQGLSSPVTKSFNRGEC (SEQ ID NO: 10).

In some embodiments, anti-TLR4 antibody or immunologically active fragment thereof is or is derived from an antibody as described in PCT/IB2005/004206, filed Jun. 14, 2005 and published as WO 20071110678, the contents of which are hereby incorporated by reference in their entirety.

In some embodiments, anti-TLR4 antibody or immunologically active fragment thereof is or is derived from an antibody as described in PCT application PCT/IB2008/003978, filed May 14, 2008 and published as WO 2009/101479, the contents of which are hereby incorporated by reference in their entirety.

In some embodiments, anti-TLR4 antibody or immunologically active fragment thereof is or is derived from the anti-TLR4 antibody known as HTA125, which is described, for example, in Shimazu, et al., J. Exp. Med., val. 189:1777-1782 (1999); Nijhuis et al., Clin Diag. Lab. Immunol., val. 10(4): 558-63 (2003); and Pivarcsi et al., Intl. Immunopharm., vol. 15(6):721-730 (2003), the contents of each of which are hereby incorporated by reference in their entirety.

In some embodiments, the anti-TLR4 antibody or immunologically active fragment thereof is or is derived from a domain antibody such as, for example, the domain antibodies that bind TLR4 described in PCT application PCT/EP2009/055926, filed May 15, 2009 and published as WO 2009/13848, the contents of which are hereby incorporated by reference in their entirety.

In some embodiments, the anti-TLR4 antibody or immunologically active fragment thereof is or is derived from monoclonal antibodies recognizing human and/or cynomolgus monkey TLR4/MD-2 receptor expressed on the cell surface. The antibodies are capable of blocking, e.g., neutralizing, receptor activation and subsequent intracellular signaling induced TLR4 ligands, e.g., LPS or any other TLR4 ligand described herein. Antibodies of the invention include antibodies that bind human and cynomolgus monkey TLR4/MD-2 receptor complex and also bind TLR4 independently of the presence of MD-2.

In some embodiments, the anti-TLR4 antibody or immunologically active fragment thereof interferes with or otherwise antagonizes signaling via human and/or cynomolgus monkey TLR4/MD-2 receptor expressed on the cell surface, e.g., by blocking receptor activation and subsequent intracellular signaling induced by LPS. Exemplary monoclonal antibodies of these embodiments include: 1A1, 1A6, 1B12, 1C7, 1C10, 1C12, 1D10, 1E11, 1E11 N103D, 1G12, 1E11.C1, 1E11.C2, 1E11.C3, 1E11.C4, 1E11.C5, 1E11.C6, 1E11.E1, 1E11.E2, 1E11.E3, 1E11.E4, 1E11.E5, 1E11.C2E1, 1E11.C2E3, 1E11.C2E4 and 1E11.C2E5.

These antibodies have distinct specificities. Some antibodies show specificity for both the human and cynomolgus monkey TLR4 and/or both the human and cynomolgus monkey TLR4/MD-2 receptor complex, and they have been shown to inhibit receptor activation and subsequent intracellular signaling via LPS. For example, 1C12, 1E11, 1E11 N103D, 1E11.C1, 1E11.C2, 1E11.C3, 1E11.C4, 1E11.C5, 1E11.C6, 1E11.C2E1, 1E11.C2E2, 1E11.C2E3, 1E11.C2E4 and 1E11.C2E5 bind both human and cynomolgus monkey TLR4 independently of the presence of human or cynomolgus monkey MD-2. 1A1, 1A6, 1B12, 1C7, 1C10, 1D10 and 1G12 only bind to cynomolgus monkey TLR4 independently of the presence of cynomolgus monkey MD-2. 1E11.E1, 1E11.E2, 1E11.E3, 1E11.E4 and 1E11.E5 bind only to human TLR4 independently of the presence of human MD-2.

The humanized antibodies of the invention contain a heavy chain variable region having an amino acid sequence shown herein. The humanized antibodies of the invention contain a light chain variable region having an amino acid sequence shown herein.

The three heavy chain CDRs include an amino acid sequence at least 90%, 92%, 95%, 97% 98%, 99% or more identical to a variable heavy chain complementarity determining region 1 (VH CDR1, also referred to herein as CDRH1) amino acid sequence selected from the group consisting of G(F/Y)PI(R/G/W)(Y/F/G)GYS (SEQ ID NO: 14), GYSITGGYS (SEQ ID NO: 15); GFPIRYGYS (SEQ ID NO: 16); GYPIRFGYS (SEQ ID NO: 17); GYPIRHGYS (SEQ ID NO: 18); GFPIGQGYS (SEQ ID NO: 19); GYPIWGGYS (SEQ ID NO: 20) and GYPIGGGYS (SEQ ID NO: 21), a variable heavy chain complementarity determining region 2 (VH CDR2, also referred to herein as CDRH2) amino acid sequence of IHYSGYT (SEQ ID NO: 22); and a variable heavy chain complementarity determining region 3 (VH CDR3, also referred to herein as CDRH3) amino acid sequence selected from the group consisting of ARKDSG(N/Q/D/E)$X_1X_2$PY. (SEQ ID NO: 23) where $X_1$ and $X_2$ are each independently any hydrophobic amino acid, ARKDSGNYFPY (SEQ ID NO: 24), ARKDSGRLLPY (SEQ ID NO: 25); ARKDSGKWLPY (SEQ ID NO: 26); ARKDSGHLMPY (SEQ ID NO: 27); ARKDSGHNYPY (SEQ ID NO: 28); ARKDSGKNFPY (SEQ ID NO: 29); ARKDSGQLFPY (SEQ ID NO: 30); ARKDSGHNLPY (SEQ ID NO: 31); ARKDSGDYFPY (SEQ ID NO: 32) and ARKDSGRYWPY (SEQ ID NO: 33). The three light chain CDRs include an amino acid sequence at least 90%, 92%, 95%, 97% 98%, 99% or more identical to a variable light chain complementarity determining region 1 (VL CDR1, also referred to herein as CDRL1) amino acid sequence of QSISDH (SEQ ID NO: 34); a variable light chain complementarity determining region 2 (VL CDR2, also referred to herein as CDRL2) amino acid sequence of YAS (SEQ ID NO: 35); and a variable light chain complementarity determining region 3 (VL CDR3, also referred to herein as CDRL3) amino acid sequence selected from the group consisting of QQG(Y/N)(D/E)(F/Y)PXT (SEQ ID NO: 36) where X is any hydrophobic amino acid, QQGHSFPLT (SEQ ID NO: 6); QQGNDFPVT (SEQ ID NO: 37); QQGYDEPFT (SEQ ID NO: 38); QQGYDFPFT (SEQ ID NO: 39); QQGYDYPFT (SEQ ID NO: 40) and QQGYEFPFT (SEQ ID NO: 41). The antibodies bind to human and cynomolgus monkey TLR4/MD-2 complex, to human and cynomolgus TLR4 when not complexed with human and cynomolgus MD-2, to human TLR4/MD-2 complex, to human TLR4 when not complexed with human MD-2, to cynomolgus monkey TLR4/MD-2 complex or cynomolgus TLR4 when not complexed with cynomolgus MD-2.

The anti-TLR4 antibodies of the invention also include antibodies that include a heavy chain variable amino acid sequence that is at least 90%, 92%, 95%, 97%, 98%, 99% or more identical an amino acid sequence shown herein, and/or a light chain variable amino acid that is at least 90%, 92%, 95%, 97%, 98%, 99% or more identical an amino acid sequence shown herein.

In some embodiments, the anti-TLR4 antibodies described herein also include at least one specific amino acid substitution within, for example, an Fc region or an FcR binding fragment thereof (e.g., a polypeptide having amino acid substitutions within an IgG constant domain) such that the modified antibody elicits alterations in antigen-dependent effector function while retaining binding to antigen as compared to an unaltered antibody. For example, the altered antibodies elicit the prevention of proinflammatory mediator release. In a preferred embodiment, the altered antibodies are human and of the IgG1 isotype.

The anti-TLR4 antibodies of the invention include an altered antibody in which at least one amino acid residue in the constant region of the Fc portion of the antibody has been modified. For example, at least one amino acid in the CH2 domain of the Fc portion has been replaced by a different residue, i.e., an amino acid substitution. In the altered antibodies described herein, one or more of the amino acid residues that correspond to residues 325, 326 and 328 is substituted with a different residue as compared to an unaltered antibody. The numbering of the residues in the gamma heavy chain is that of the EU index (see Edelman, G. M. et al., 1969; Kabat, E, A., T. T. Wu, H. M. Perry, K. S. Gottesman, and C. Foeller., 1991. *Sequences of Proteins of Immunological Interest,* 5th Ed. U.S. Dept. of Health and Human Services, Bethesda, M D, NIH Publication n. 91-3242). In a preferred embodiment, EU amino acid position 325 of the gamma heavy chain constant region is substituted with serine, and EU amino acid position 328 of the gamma heavy chain constant region is substituted with phenylalanine, such that the EU positions 325 to 328 of the gamma heavy chain constant region of the altered human IgG1 antibody comprise the amino acid sequence SKAF (SEQ ID NO: 137).

The present invention also provides methods of treating or preventing pathologies associated with aberrant TLR4/MD-2 activation, aberrant TLR4 signaling, aberrant, e.g., elevated, TLR4 ligand expression and/or activity, aberrant pro-inflammatory cytokine production, and combinations thereof, or alleviating a symptom associated with such pathologies, by identifying a patient suitable for therapy with a neutralizing anti-TLR4 agent, e.g., a neutralizing anti-TLR4 antibody, and administering the agent, e.g., a monoclonal antibody of the invention (e.g., a murine monoclonal or humanized monoclonal antibody) to a subject in which such treatment or prevention is desired. The subject to be treated is, e.g., human. The monoclonal antibody is administered in an amount sufficient to treat, prevent or alleviate a symptom associated with the pathology. The amount of monoclonal antibody sufficient to treat or prevent the pathology in the subject is, for example, an amount that is sufficient to reduce TLR4 ligand-induced production of one or more pro-inflammatory cytokines (e.g., IL-6, IL-8, TNFα). As used herein, the term "reduced" refers to a decreased production of a pro-inflammatory cytokine in the presence of a monoclonal antibody of the invention, wherein the production is, for example, local pro-inflammatory cytokine production (e.g., at a site of inflamed tissue) or systemic pro-inflammatory cytokine production. TLR4 ligand-induced production of a pro-inflammatory cytokine is decreased when the level of pro-inflammatory cytokine production in the presence of a monoclonal antibody of the invention is greater than or equal to 5%, 10%, 20%, 25%, 30%, 40%, 50%, 60%, 70%, 75%, 80%, 90%, 95%, 99%, or 100% lower than a control level of pro-inflammatory cytokine production (i.e., the level of pro-inflammatory cytokine production in the absence of the monoclonal antibody). Level of pro-inflammatory cytokine production is measured. Those skilled in the art will appreciate that the level of pro-inflammatory cytokine production can be measured using a variety of assays, including, for example, the methods described herein as well as commercially available ELISA kits.

Pharmaceutical compositions according to the invention can include an anti-TLR4 antibody of the invention and a carrier. These pharmaceutical compositions can be included in kits, such as, for example, diagnostic kits.

The invention also provides kits for practicing any of the methods provided herein. For example, in some embodiments, the kits include a detection reagent specific for one or more TLR4 ligands or other biomarkers and a means for detecting the detection reagent.

BRIEF DESCRIPTION OF THE DRAWINGS

FIG. 2A, anti-citrullinated protein antibodies (ACPA); FIG. 2B, immune complex containing citrullinated fibrinogen (cFb-IC); FIG. 2C, high-mobility group protein B1 (HMGB1); FIG. 2D, S100A8/A9; FIG. 2E, Tenascin C.

FIG. 3A depicts a RASF (from patient #1; RASF 1) that does stimulate RA synovial fibroblasts to produce the pro-inflammatory cytokine, IL-6. This stimulation is significantly blocked by the presence of an anti-human TLR4 mAb (e.g., NI-0101). In contrast, FIG. 3B depicts a RASF sample (from patient #2; RASF 2) that is unable to stimulate IL-6 production from RA synovial fibroblasts and the anti-TLR4 mAb has no effect in this circumstance. higG1 is used as the isotype control. Student's t tests were performed. ***p<0.001, ns: not significant.

FIGS. 4A, 4B and 4C depict the ability of a RASF sample (from patient #3; RASF 3) to stimulate production of the pro-inflammatory cytokines, IL-6, IL8 and TNFα, respectively, from human monocytes isolated from RA patients. This stimulation is significantly blocked by the presence of an anti-human TLR4 mAb (e.g., NI-0101). In contrast, FIGS. 4D, 4E and 4F depict a RASF sample (from patient #4; RASF 4) that is unable to stimulate the production of IL-6, IL8 and TNFα from human monocytes isolated from RA patients and the anti-TLR4 mAb has no effect in this circumstance. hIgG1 is used as the isotype control. Student's t tests were performed. *p<0.05, p<0.01, *p<0.001, ns: not significant.

FIGS. 6A and 6B are a series of graphs illustrating the marker levels by cellular response scores to treatment with the anti-human TLR4 mAb, NI-0101 in monocytes (FIG. 6A) or fibroblasts (FIG. 6B). Cellular response scores: 0, 1, or 2 cell donors responded to rheumatoid arthritis synovial fluids (RASF) stimulation and was/were inhibited by treatment with NI-0101.

DETAILED DESCRIPTION OF THE INVENTION

The compositions and methods provided herein are useful in identifying or otherwise refining a patient population suffering from a disorder, where the patient has an elevated level of one or more TLR4 ligands or other biomarkers. These patients are identified as suitable candidates for treatment with an agent (e.g., an antibody or other polypeptide-based therapeutic, a peptide-based therapeutic, a small molecule inhibitor, a nucleic acid-based therapeutic and derivatives thereof) that interferes with or otherwise antagonizes TLR4 signaling and neutralizes at least one biological activity of TLR4, alone or in the context of the accessory protein MD-2 as the TLR4/MD-2 complex.

In some patients suffering from or suspected of suffering from a disorder, fluids and other biological samples contain elevated levels of TLR4 ligands and other biomarkers. These TLR4 ligands and other biomarkers stimulate cells to produce pro-inflammatory cytokines. However, use of an anti-TLR4 antagonist that interferes with or otherwise antagonizes TLR4 signaling, e.g., a neutralizing anti-TLR4 antibody or other anti-TLR4 agent, is shown herein to block this stimulation in patients exhibiting an elevated level of expression for one or more TLR4 ligands and/or other biomarkers. Thus, the compositions and methods are useful in treating, delaying the progression of or otherwise ameliorating a symptom of a disorder that is dependent on, driven by, or otherwise associated with TLR4 signaling, aberrant, e.g., elevated, TLR4 ligand expression and/or activity, aberrant pro-inflammatory cytokine production, and/or combinations thereof, by administering an anti-TLR4 antagonist, e.g., a neutralizing anti-TLR4 antibody or other polypeptide-based therapeutic, a peptide-based therapeutic, a small molecule inhibitor, a nucleic acid-based therapeutic and derivatives thereof, to patients exhibiting an elevated level of expression for one or more TLR4 ligands and/or biomarkers. Patients that are likely suitable candidates for treatment with the anti-TLR4 antagonist, e.g., neutralizing anti-TLR4 antibody such as those described herein, are identified by detecting the level of one or more TLR4 ligands or other biomarkers.

Figure 1A:
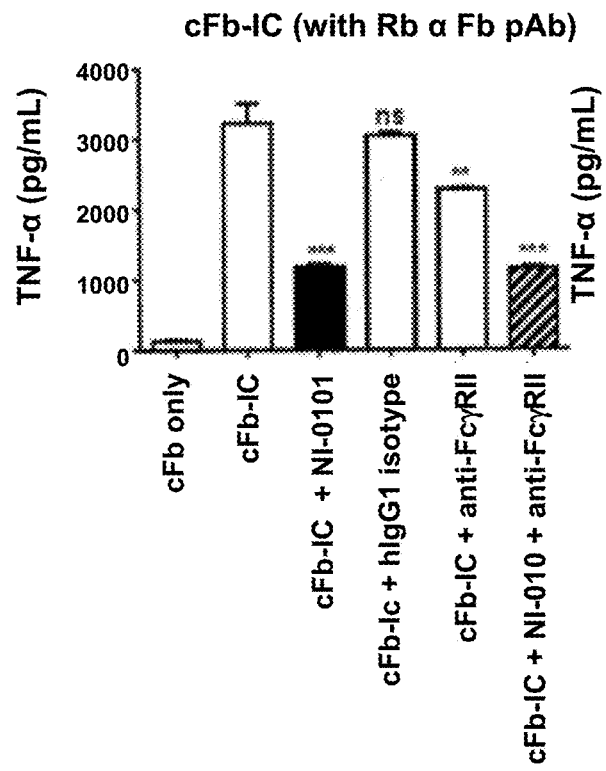
FIGS. 1A and 1B are a series of graphs that depict the activation of human blood-derived macrophages (HBDMs) by immune complexed citrullinated fibrinogen (cFb-IC) and the mechanism of action being dependent on TLR4 and a partial contribution from Fc gamma receptors. As demonstrated in FIG. 1A, cFb does not induce the secretion of the pro-inflammatory cytokine, TNFα, by HBDM, whereas when presented as an immune complex with rabbit anti-fibrinogen polyclonal antibodies (Rb α Fb pAb), the cFb-IC is activating. In the presence of HBDM, cFb-IC and an anti-human TLR4 mAb (e.g., NI-0101), the activation potential is significantly blocked. In the presence of HBDM, cFb-IC and an anti-human FcRII mAb, a partial impairment is observed. When adding both mAbs to the HBDM and cFb-IC, no additional inhibition to that of anti-human TLR4 mAb (e.g., NI-0101) is observed. higG1 is used with HBDM and cFb-IC as the isotype control. As demonstrated in FIG. 1B, these results of stimulation and blockade are repeated when the source for the immune complex is purified human IgG from rheumatoid arthritis patient's sera. Student's t test were performed. *p<0.05, p<0.01, *p<0.001, ns: not significant.
Figure 1B:
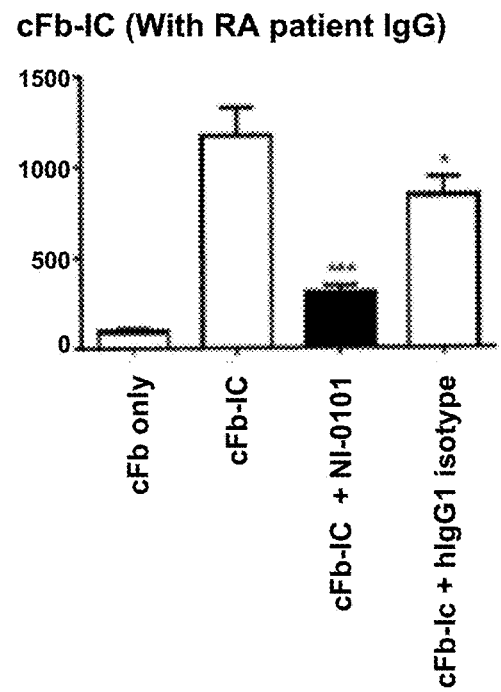
Figure 2A:
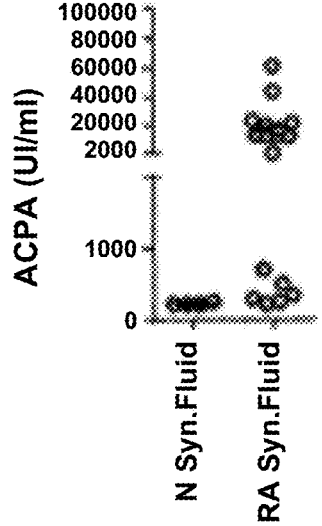
FIGS. 2A-2E are a series of graphs that depict examples of the levels of anti-citrullinated protein antibodies and different TLR4 ligands contained in synovial fluid of healthy subjects (N Syn.Fluid) or patients with rheumatoid arthritis (RA Syn.Fluid).
Figure 2B:
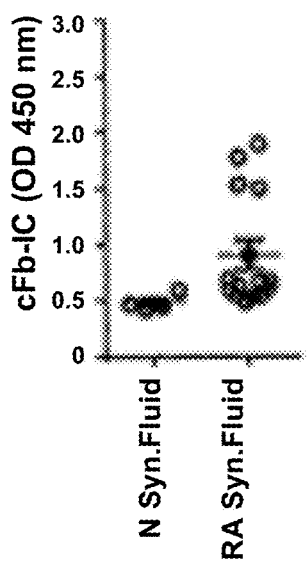
Figure 2C:
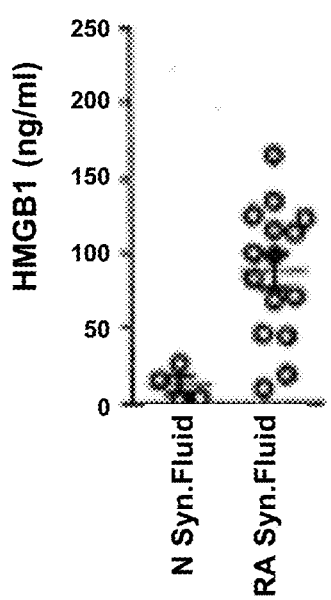
Figure 2D:
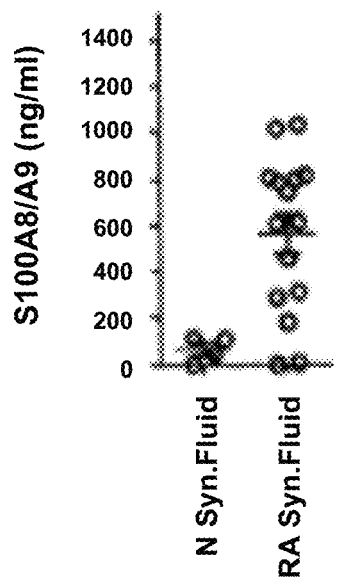
Figure 2E:
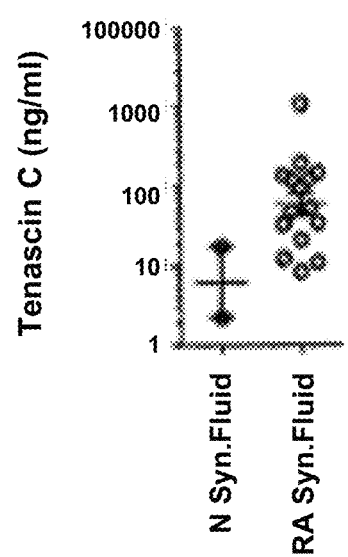

Previous studies demonstrated that citrullinated fibrinogen (cFb) in an immune complex (cFb-IC) stimulated secretion of pro-inflammatory cytokines, and this stimulation could be inhibited by an anti-TLR4 antagonist. See Sokolove et al., "Immune Complexes Containing Citrullinated Fibrinogen Costimulate Macrophages via Toll-like Receptor 4 and Fcγ Receptor," Arthritis & Rheumatism, vol. 63, No. 1, January 2011, pp 53-62. Similar studies were run using the anti-TLR4 antibody described herein, referred to as NI-0101 (FIGS. 1A-1B). Human blood-derived macrophages (HBDMs) were activated by immune complexed citrullinated fibrinogen (cFb-IC), and the mechanism of action being dependent on TLR4 and a partial contribution from Fc gamma receptors. As shown in FIG. 1A, cFb did not induce the secretion of the pro-inflammatory cytokine, TNFα, by HBDM, whereas when presented as an immune complex with rabbit anti-fibrinogen polyclonal antibodies (Rb α Fb pAb), the cFb-IC was activating. In the presence of HBDM, cFb-IC and an anti-human TLR4 mAb (e.g., NI-0101), the activation potential was significantly blocked. In the presence of HBDM, cFb-IC and an anti-human FcRII mAb, a partial impairment was observed. When adding both mAbs to the HBDM and cFb-IC, no additional inhibition to that of anti-human TLR4 mAb (e.g., NI-0101) was observed.

The studies provided herein build upon and expand the findings in these initial studies by determining additional TLR4 ligands and other biomarkers that can be used to identify patients that are likely candidates for treatment with an anti-TLR4 antagonist.

Suitable TLR4 ligands and other biomarkers for use in identifying likely candidates include anti-citrullinated protein antibodies (ACPA), citrullinated proteins, citrullinated proteins in an immune complex, e.g., citrullinated fibrinogen (cFb) in an immune complex with an IgG protein (cFb-IC) or an IgE protein, HMGB1, S100A8/A9, Tenascin C, LPS, heat shock proteins (HSPs), fibronectin, hyaluronan, Der P2, Respiratory Syncytial Virus F (RSV) F protein, Surfactant A, Coxsakievirus B4 (CSV B4), CXCL10, Resistin, Fetuin A, Saturated Fatty Acid (SFA), Biglycan, Modified Low-Density Lipoprotein (mLDL), advanced glycation end products (AGE) and combinations thereof. In some embodiments, the citrullinated protein is citrullinated fibrinogen, citrullinated fibrin, citrullinated vimentin, a citrullinated histone (e.g., citrullinated histone 2b), citrullinated enolase or a citrullinated chemokine, (e.g. citrullinated CXCL10). In addition to detecting the level of one or more of these TLR4 ligands and/or biomarkers, suitable patients for treatment with an anti-TLR4 antagonist can also be identified by evaluating any of a number of additional biological and clinical parameters that will improve the sensitivity and specificity of the biomarker for identifying or otherwise refining the patient population. Alternatively, these additional biological and clinical parameters can be used alone as a means for identifying patients that are suitable candidates for treatment with an anti-TLR4 antagonist or other suitable therapy. These biological and clinical parameters include, by way of non-limiting example, any of the following: rheumatoid factor levels, C-reactive protein (CRP) levels, blood cells count, presence of TLR4 receptor on blood cell subpopulations, TLR4 polymorphisms, human leukocyte antigen (HLA) polymorphisms, peptidyl arginine deiminase (PAD) enzymes and PAD enzyme polymorphisms, Fcγ Receptor IIa (FcγIIa) polymorphisms, MD-2 levels, soluble CD14 levels, baseline patient demographic data (e.g., body mass index (BMI), sex, age, etc.) and/or patient medical history (e.g., disability assessment schedule (DAS 28) at diagnosis, DAS 28 at treatment initiation, duration of disease, age at disease onset, response to prior treatments based on DAS28, American College of Rheumatology (ACR) and/or European League Against Rheumatism (EULAR) response criteria, etc.) In some embodiments, a combination of TLR4 ligands, other biomarkers and/or additional biological/clinical parameters is detected, for example, at least two TLR4 ligands, other biomarkers and/or additional biological/clinical parameters are detected, at least three TLR4 ligands, other biomarkers and/or additional biological/clinical parameters are detected, at least four TLR4 ligands, other biomarkers and/or additional biological/clinical parameters are detected, at least five TLR4 ligands, other biomarkers and/or additional biological/clinical parameters are detected, at least six TLR4 ligands, other biomarkers and/or additional biological/clinical parameters are detected, at least seven TLR4 ligands, other biomarkers and/or additional biological/clinical parameters are detected, at least eight TLR4 ligands, other biomarkers and/or additional biological/clinical parameters are detected, at least nine TLR4 ligands, other biomarkers and/or additional biological/clinical parameters are detected, or at least ten TLR4 ligands, other biomarkers and/or additional biological/clinical parameters or more are detected.

In some embodiments, the TLR4 ligand or other biomarker is S100A8/A9. In some embodiments, the TLR4 ligand or other biomarker is cFb-IC. In some embodiments, the TLR4 ligand or other biomarker is ACPA. In some embodiments, the TLR4 ligand or other biomarker is HMGB1. In some embodiments, the TLR4 ligand or other biomarker is a combination of S100A8/A9 and HMGB1. In some embodiments, the TLR4 ligand or other biomarker is a combination of S100A8/A9 and cFb-IC. In some embodiments, the TLR4 ligand or other biomarker is a combination of S100A8/A9 and ACPA. In some embodiments, the TLR4 ligand or other biomarker is a combination of ACPA and cFb-IC. In some embodiments, the TLR4 ligand or other biomarker is a combination of ACPA and HMGB1. In some embodiments, the TLR4 ligand or other biomarker is a combination of HMGB1 and cFb-IC. In some embodiments, the TLR4 ligand or other biomarker is a combination of S100A8/A9, ACPA and HMGB1. In some embodiments, the TLR4 ligand or other biomarker is a combination of S100A8/A9, ACPA and cFb-IC. In some embodiments, the TLR4 ligand or other biomarker is a combination of S100A8/A9, cFb-IC and HMGB1. In some embodiments, the TLR4 ligand or other biomarker is a combination of ACPA, HMGB1 and cFb-IC. In some embodiments, the TLR4 ligand or other biomarker is a combination of S100A8/A9, cFb-IC, ACPA and HMGB1.

In some embodiments, the TLR4 ligand or other biomarker is a predictor of monocyte response to exposure to an anti-TLR4 agent, e.g., an anti-TLR4 mAb such as NI-0101. In some embodiments, the predictor of monocyte response to anti-TLR4 treatment is S100A8/A9. In some embodiments, the predictor of monocyte response to anti-TLR4 treatment is ACPA. In some embodiments, the predictor of monocyte response to anti-TLR4 treatment is HMGB1. In some embodiments, the predictor of monocyte response to anti-TLR4 treatment is cFb-IC.

In some embodiments, the TLR4 ligand or other biomarker is a predictor of fibroblast response to exposure to an anti-TLR4 agent, e.g., an anti-TLR4 mAb such as NI-0101. In some embodiments, the predictor of fibroblast response to anti-TLR4 treatment is cFb-IC.

In some embodiments, the TLR4 ligand or other biomarker is a predictor of monocyte and fibroblast response to exposure to an anti-TLR4 agent, e.g., an anti-TLR4 mAb such as NI-0101. In some embodiments, the predictor of monocyte and fibroblast response is ACPA. In some embodiments, the predictor of monocyte and fibroblast response is cFb-IC. In some embodiments, the predictor of monocyte and fibroblast response is S100A8/A9. In some embodiments, the predictor of monocyte and fibroblast response is HMGB1. In some embodiments, the predictor of monocyte and fibroblast response is a combination of S100A8/A9 and HMGB1. In some embodiments, the predictor of monocyte and fibroblast response is a combination of ACPA and cFb-IC. In some embodiments, the predictor of monocyte and fibroblast response is a combination of S100A8/A9 and cFb-IC. In some embodiments, the predictor of monocyte and fibroblast response is a combination of S100A8/A9 and ACPA. In some embodiments, the predictor of monocyte and fibroblast response is a combination of ACPA and cFb-IC. In some embodiments, the predictor of monocyte and fibroblast response is a combination of ACPA and HMGB1. In some embodiments, the predictor of monocyte and fibroblast response is a combination of HMGB1 and cFb-IC. In some embodiments, the predictor of monocyte and fibroblast response is a combination of S100A8/A9, ACPA and HMGB1. In some embodiments, the predictor of monocyte and fibroblast response is a combination of S100A8/A9, ACPA and cFb-IC. In some embodiments, the predictor of monocyte and fibroblast response is a combination of S100A8/A9, cFb-IC and HMGB1. In some embodiments, the predictor of monocyte and fibroblast response is a combination of ACPA, HMGB1 and cFb-IC. In some embodiments, the predictor of monocyte and fibroblast response is a combination of S100A8/A9, cFb-IC, ACPA and HMGB1.

The studies provided herein demonstrate that agents that neutralize TLR4 activity, e.g., TLR4-mediated signaling, are effective to substantially or completely block pro-inflammatory cytokine production by activated cells in samples from patients suffering from or at risk for a disorder. The studies provided herein also demonstrate that targeting only the Fc region, e.g., through the use of agents that neutralize Fc activity, e.g., anti-CD32 antibodies, is effective to partially block pro-inflammatory cytokine production by activated cells in patients suffering from or at risk for a disorder. Anti-TLR4 antagonists are considered to completely block pro-inflammatory cytokine production by activated cells when the level of pro-inflammatory cytokine production by activated cells in the presence of the anti-TLR4 is decreased by at least 95%, e.g., by 96%, 97%, 98%, 99% or 100% as compared to the level of pro-inflammatory cytokine production by activated cells in the absence of interaction, e.g., binding, with the anti-TLR4 antagonist. Anti-TLR4 antagonists are considered to partially block pro-inflammatory cytokine production by activated cells when the level of pro-inflammatory cytokine production by activated cells in the presence of the anti-TLR4 is decreased by at least 50%, e.g., 55%, 60%, 75%, 80%, 85% or 90% as compared to the level of pro-inflammatory cytokine production by activated cells in the absence of interaction, e.g., binding, with the anti-TLR4 antagonist. Targeting only the Fc region, e.g., through the use of anti-Fc agents, is considered to partially block pro-inflammatory cytokine production by activated cells when the level of pro-inflammatory cytokine production by activated cells after targeting only the Fc region is decreased by less than 95%, e.g., 10%, 20%, 25%, 30%, 40%, 50%, 60%, 75%, 80%, 85% or 90% as compared to the level of pro-inflammatory cytokine production by activated cells in the absence of targeting only the Fc region, e.g., in the absence of an interaction, e.g., binding, with an anti-Fc agent.

Disorders that are useful with the compositions and methods of the invention include any disorder where aberrant, e.g., elevated, TLR4 expression and/or activity, with aberrant TLR4/MD-2 activation and/or aberrant TLR4 ligand activity (e.g., aberrant stimulation of pro-inflammatory cytokine production such as aberrant stimulation of IL-6, TNFα and/or IL-8 production). For example, some TLR4 ligands are believed to be associated with various disorders.

By way of non-limiting example, LPS is known to be associated with disorders such as sepsis, acute lung injury, and/or RA. (See e.g., Opal, S. M. 2007. The host response to endotoxin, antilipopolysaccharide strategies, and the management of severe sepsis. Int. J. Med. Microbial. 297: 365-377; Wahamaa, H., et al. High mobility group box protein 1 in complex with lipopolysaccharide or IL-1 promotes an increased inflammatory phenotype in synovial fibroblasts. Arthritis Res. Ther. 13: R136).

By way of non-limiting example, Tenascin C is known to be associated with disorders such as arthritis, hepatic and/or cardiac ischemial reperfusion. (See e.g., Kuriyama, N., et al. 2011. Tenascin-c: A novel mediator of hepatic ischemia and reperfusion injury. Hepatology; Midwood, K. et al. 2009. Tenascin-C is an endogenous activator of Toll-like receptor 4 that is essential for maintaining inflammation in arthritic joint disease. Nat. Med. 15: 774-780; Taki, J., et al. 2010. Dynamic expression of tenascin-C after myocardial ischemia and reperfusion: assessment by 125I-anti-tenascin-C antibody imaging. J. Nucl. Med. 51: 1116-1122).

By way of non-limiting example, HMGB1 is known to be associated with disorders such as RA, Osteoarthritis (OA), ischemial reperfusion, Type 1 diabetes, islet transplantation, lupus and/or sepsis. (See e.g., Chen, J., et al. 2011. Toll-like receptor 4 regulates early endothelial activation during ischemic acute kidney injury. Kidney Int. 79: 288-299; Wahamaa, H., et al. High mobility group box protein 1 in complex with lipopolysaccharide or IL-1 promotes an increased inflammatory phenotype in synovial fibroblasts. Arthritis Res. Ther. 13: R136); Abdulahad, D. A., et al. 2011. High mobility group box 1 (HMGB1) and anti-HMGB1 antibodies and their relation to disease characteristics in systemic lupus erythematosus. Arthritis Res. Ther. 13: R71; Chen, J., et al. 2011. Early interleukin 6 production by leukocytes during ischemic acute kidney injury is regulated by TLR4. Kidney Int. 80: 504-515; Huang, W., et al. 2010. HMGB1, a potent proinflammatory cytokine in sepsis. Cytokine 51: 119-126; Jiang, W., and D. S. Pisetsky. 2008. Expression of high mobility group protein 1 in the sera of patients and mice with systemic lupus erythematosus. Ann. Rheum. Dis. 67: 727-728; Li, M., et al. 2012. Toll-like receptor 4 on beta cells senses expression changes in high-mobility group box 1 and contributes to the initiation of type 1 diabetes. Exp. Mol. Med; Matsuoka, N., et al. 2010. High-mobility group box 1 is involved in the initial events of early loss of transplanted islets in mice. J. Clin. Invest 120:735-743; Nogueira-Machado, J. A., et al., 2011. HMGB1, TLR and RAGE: a functional tripod that leads to diabetic inflammation. Expert. Opin. Ther. Targets. 15: 1023-1035; Schierbeck, H., et al. 2011. Monoclonal anti-HMGB1 antibody protection in two experimental arthritis models. Mol. Med. September-October; 17(9-10):1039-44. Epub 2011 Jun. 7; Urbonaviciute, V., and R. E. Voll. 2011. High-mobility group box 1 represents a potential marker of disease activity and novel therapeutic target in systemic lupus erythematosus. J. Intern. Med. 270: 309-318; Wu, H., et al. 2010. HMGB1 contributes to kidney ischemia reperfusion injury. J. Am. Soc. Nephrol. 21: 1878-1890).

By way of non-limiting example, S100A8/A9 is known to be associated with disorders such as RA, OA, juvenile idiopathic arthritis (JIA), diabetes, transplant rejection, lupus, atherosclerosis, sepsis and/or cancer. (See e.g., Arai, K., et al. 2008. S100A8 and S100A9 overexpression is associated with poor pathological parameters in invasive ductal carcinoma of the breast. Curr. Cancer Drug Targets. 8: 243-252; Bouma, G., et al. 2004. Increased serum levels of MRP-8114 in type 1 diabetes induce an increased expression of CD11b and an enhanced adhesion of circulating monocytes to fibronectin. Diabetes 53: 1979-1986; Frosch, M., et al. 2009. The myeloid-related proteins 8 and 14 complex, a novel ligand of toll-like receptor 4, and interleukin-lbeta form a positive feedback mechanism in systemic-onset juvenile idiopathic arthritis. Arthritis Rheum. 60: 883-891; Ionita, M. G., et al. 2009. High levels of myeloid-related protein 14 in human atherosclerotic plaques correlate with the characteristics of rupture-prone lesions. Arterioscler. Thromb. Vasc. Biol. 29: 1220-1227; Jung, D. Y., et al. 2008. Combined use of myeloid-related protein 8114 and procalcitonin as diagnostic markers for acute allograft rejection in kidney transplantation recipients. Transpl. Immunol. 18: 338-343; Kawai, H., et al. 2011. Prognostic impact of S100A9 overexpression in non-small cell lung cancer. Tumour. Biol. 32: 641-646; Loser, K., et al. 2010. The Toll-like receptor 4 ligands Mrp8 and Mrp14 are crucial in the development of autoreactive $CD8^+$ T cells. Nat. Med. 16: 713-717; Peng, W. H., et al. 2011. Increased serum myeloid-related protein 8/14 level is associated with atherosclerosis in type 2 diabetic patients. Cardiovasc. Diabetol. 10: 41; Schulze zur, W. A., et al. 2004. Myeloid related proteins MRP8/MRP14 may predict disease flares in juvenile idiopathic arthritis. Clin. Exp. Rheumatol. 22: 368-373; Soyfoo, M. S., et al. 2009. Phagocyte-specific S100A8/A9 protein levels during disease exacerbations and infections in systemic lupus erythematosus. J. Rheumatol. 36: 2190-2194; Sunahori, K., et al. 2006. The S100A8/A9 heterodimer amplifies proinflammatory cytokine production by macrophages via activation of nuclear factor kappa B and p38 mitogen-activated protein kinase in rheumatoid arthritis. Arthritis Res. Ther. 8: R69; van Lent, P. L., et al. 2010. S100A8 causes a shift toward expression of activatory Fcgamma receptors on macrophages via toll-like receptor 4 and regulates Fcgamma receptor expression in synovium during chronic experimental arthritis. Arthritis Rheum. 62: 3353-3364; van Zoelen, M. A., et al. 2009. Expression and role of myeloid-related protein-14 in clinical and experimental sepsis. Am. J. Respir. Crit Care Med. 180: 1098-1106; Zreiqat, H., et al. 2010. S100A8 and S100A9 in experimental osteoarthritis. Arthritis Res. Ther. 12: R16).

By way of non-limiting example, citrullinated fibrinogen is known to be associated with disorders such as RA and atherosclerosis. (See e.g., Kuhns, D. B., et al. 2007. Induction of human monocyte interleukin (IL)-8 by fibrinogen through the toll-like receptor pathway. Inflammation 30: 178-188; Smiley, S. T., et al. 2001. Fibrinogen stimulates macrophage chemokine secretion through toll-like receptor 4. J. Immunol. 167: 2887-2894; Sokolove, J., et al. 2011. Immune complexes containing citrullinated fibrinogen costimulate macrophages via Toll-like receptor 4 and Fcgamma receptor. Arthritis Rheum. 63: 53-62).

By way of non-limiting example, ACPA is known to be associated with disorders such as RA, psoriatic arthritis, systemic lupus erythematosus (SLE), Sjogren's syndrome, Alzheimer disease and/or atherosclerosis. (See e.g., Nicholas A P. Dual immunofluorescence study of citrullinated proteins in Alzheimer diseased frontal cortex. Neurosci Lett. 2013 Jun. 17; 545:107-11. Epub 2013 May 3. PubMed PMID: 23648390); Giles J T, et al. Association of fine specificity and repertoire expansion of anticitrullinated peptide antibodies with rheumatoid arthritis associated interstitial lung disease. Ann Rheum Dis. 2013 May 28. (Epub ahead of print) PubMed PMID: 23716070); Gómara M J, Haro I. Citrullinated peptides in the diagnosis of rheumatoid arthritis. Curr Top Med Chem. 2013; 13(6):743-51. PubMed PMID: 23574523); Dalmady S, et al. Higher levels of autoantibodies targeting mutated citrullinated vimentin in patients with psoriatic arthritis than in patients with psoriasis vulgaris. Clin Dev Immunol. 2013; 2013:474028. March 18. PubMed PMID: 23573111; PubMed Central PMCID: PMC3614022); Herrera-Esparza R, et al. Posttranslational Protein Modification in the Salivary Glands of Sjogren's Syndrome Patients. Autoimmune Dis. 2013; 2013:548064. Epub 2013 Mar. 5. PubMed PMID: 23533719; PubMed Central PMCID: PMC3603161); and Cambridge G, et al. Antibodies to citrullinated peptides and risk of coronary heart disease. Atherosclerosis. 2013 May; 228(1):243-6. Epub 2013 Feb. 18. PubMed PMID: 23474125).

In other non-limiting examples, TLR4 ligands such as heat shock proteins (HSPs), HMGB1 and/or S100A8/A9 are believed to be associated with ischemia/reperfusion injury (I/R injury). By way of non-limiting example, TLR4 ligands such as HMGB1, S100A8/A9, fibronectin, citrullinated Fibrinogen and/or Tenascin C are believed to be associated with arthritis. By way of non-limiting example, TLR4 ligands such as heat shock proteins (HSPs), hyaluronan, Der P2, Respiratory Syncytial Virus F (RSV) F protein, Surfactant A and/or LPS are believed to be associated with lung diseases. By way of non-limiting example, TLR4 ligands such as Coxsakievirus B4 (CSV B4), CXCL10, Resistin, Fetuin A, Saturated Fatty Acid (SFA), HMGB1 and/or S100A8/A9 are believed to be associated with diabetes. By way of non-limiting example, TLR4 ligands such as heat shock proteins (HSPs), hyaluronan, Der P2, Respiratory Syncytial Virus F (RSV) F protein, Surfactant A and/or LPS are associated with lung diseases. By way of non-limiting example, TLR4 ligands such as HMGB1, S100A8/A9 Biglycan, Modified Low-Density Lipoprotein (mLDL) and/ or are advanced glycation end products (AGE) are believed to be associated with kidney diseases.

Neutralizing anti-TLR4 antibodies of the invention include, for example, the heavy chain complementarity determining regions (CDRs) shown below in Table 2A, the light chain CDRs shown in Table 2B, and combinations thereof.

TABLE 2A

VH CDR sequences from antibody clones that bind and neutralize TLR4

| Clone ID | Heavy CDR1 | Heavy CDR2 | Heavy CDR3 |
|---|---|---|---|
| N1-0101 | GGYSWH (SEQ ID NO: 1) | YIHYSGYTDFNPSLKT (SEQ ID NO: 2) | KDPSDAFPY (SEQ ID NO: 3) |
| 1A1 | GYSIT...GGYS (SEQ ID NO: 15) | IHYS...GYT (SEQ ID NO: 22) | ARKDSGRLLPY (SEQ ID NO: 25) |
| 1A6 | GYSIT...GGYS (SEQ ID NO: 15) | IHYS...GYT (SEQ ID NO: 22) | ARKDSGKWLPY (SEQ ID NO: 26) |
| 1B12 | GYSIT...GGYS (SEQ ID NO: 15) | IHYS...GYT (SEQ ID NO: 22) | ARKDSGHLMPY (SEQ ID NO: 27) |
| 1C7 | GYSIT...GGYS (SEQ ID NO: 15) | IHYS...GYT (SEQ ID NO: 22) | ARKDSGHNYPY (SEQ ID NO: 28) |
| 1C10 | GYSIT...GGYS (SEQ ID NO: 15) | IHYS...GYT (SEQ ID NO: 22) | ARKDSGKNFPY (SEQ ID NO: 29) |
| 1C12 | GYSIT...GGYS (SEQ ID NO: 15) | IHYS...GYT (SEQ ID NO: 22) | ARKDSGQLFPY (SEQ ID NO: 30) |
| 1D10 | GYSIT...GGYS (SEQ ID NO: 15) | IHYS...GYT (SEQ ID NO: 22) | ARKDSGHNLPY (SEQ ID NO: 31) |
| 1E11 | GYSIT...GGYS (SEQ ID NO: 15) | IHYS...GYT (SEQ ID NO: 22) | ARKDSGNYFPY (SEQ ID NO: 24) |
| 1E11 N103D | GYSIT...GGYS (SEQ ID NO: 15) | IHYS...GYT (SEQ ID NO: 22) | ARKDSGDYFPY (SEQ ID NO: 32) |
| 1G12 | GYSIT...GGYS (SEQ ID NO: 15) | IHYS...GYT (SEQ ID NO: 22) | ARKDSGRYWPY (SEQ ID NO: 33) |
| 1E11.C1 | GFPIR...YGYS (SEQ ID NO: 16) | IHYS...GYT (SEQ ID NO: 22) | ARKDSGNYFPY (SEQ ID NO: 24) |
| 1E11.C2 | GYPIR...FGYS (SEQ ID NO: 17) | IHYS...GYT (SEQ ID NO: 22) | ARKDSGNYFPY (SEQ ID NO: 24) |
| 1E11.C3 | GYPIR...HGYS (SEQ ID NO: 18) | IHYS...GYT (SEQ ID NO: 22) | ARKDSGNYFPY (SEQ ID NO: 24) |
| 1E11.C4 | GFPIG...QGYS (SEQ ID NO: 19) | IHYS...GYT (SEQ ID NO: 22) | ARKDSGNYFPY (SEQ ID NO: 24) |
| 1E11.C5 | GYPIW...GGYS (SEQ ID NO: 20) | IHYS...GYT (SEQ ID NO: 22) | ARKDSGNYFPY (SEQ ID NO: 24) |

TABLE 2A-continued

VH CDR sequences from antibody clones that
bind and neutralize TLR4

| Clone ID | Heavy CDR1 | Heavy CDR2 | Heavy CDR3 |
|---|---|---|---|
| 1E11.C6 | GYPIG...GGYS (SEQ ID NO: 21) | IHYS...GYT (SEQ ID NO: 22) | ARKDSGNYFPY (SEQ ID NO: 24) |
| 1E11.E1 | GYSIT...GGYS (SEQ ID NO: 15) | IHYS...GYT (SEQ ID NO: 22) | ARKDSGNYFPY (SEQ ID NO: 24) |
| 1E11.E2 | GYSIT...GGYS (SEQ ID NO: 15) | IHYS...GYT (SEQ ID NO: 22) | ARKDSGNYFPY (SEQ ID NO: 24) |
| 1E11.E3 | GYSIT...GGYS (SEQ ID NO: 15) | IHYS...GYT (SEQ ID NO: 22) | ARKDSGNYFPY (SEQ ID NO: 24) |
| 1E11.E4 | GYSIT...GGYS (SEQ ID NO: 15) | IHYS...GYT (SEQ ID NO: 22) | ARKDSGNYFPY (SEQ ID NO: 24) |
| 1E11.E5 | GYSIT...GGYS (SEQ ID NO: 15) | IHYS...GYT (SEQ ID NO: 22) | ARKDSGNYFPY (SEQ ID NO: 24) |
| 1E11.C2E1 | GYPIR...FGYS (SEQ ID NO: 17) | IHYS...GYT (SEQ ID NO: 22) | ARKDSGNYFPY (SEQ ID NO: 24) |
| 1E11.C2E3 | GYPIR...FGYS (SEQ ID NO: 17) | IHYS...GYT (SEQ ID NO: 22) | ARKDSGNYFPY (SEQ ID NO: 24) |
| 1E11.C2E4 | GYPIR...FGYS (SEQ ID NO: 17) | IHYS...GYT (SEQ ID NO: 22) | ARKDSGNYFPY (SEQ ID NO: 24) |
| 1E11.C2E5 | GYPIR...FGYS (SEQ ID NO: 17) | IHYS...GYT (SEQ ID NO: 22) | ARKDSGNYFPY (SEQ ID NO: 24) |

TABLE 2B

VL CDR sequences from antibody clones that
bind and neutralize TLR4

| Clone ID | Light CDR1 | Light CDR2 | Light CDR3 |
|---|---|---|---|
| N1-0101 | RASQSISDHLH (SEQ ID NO: 4) | YASHAIS (SEQ ID NO: 5) | QQGHSFPLT (SEQ ID NO: 6) |
| 1A1 | QSI......SDH (SEQ ID NO: 34) | YA.......S (SEQ ID NO: 35) | QQGHSFPLT (SEQ ID NO: 6) |
| 1A6 | QSI......SDH (SEQ ID NO: 34) | YA.......S (SEQ ID NO: 35) | QQGHSFPLT (SEQ ID NO: 6) |
| 1B12 | QSI......SDH (SEQ ID NO: 34) | YA.......S (SEQ ID NO: 35) | QQGHSFPLT (SEQ ID NO: 6) |
| 1C7 | QSI......SDH (SEQ ID NO: 34) | YA.......S (SEQ ID NO: 35) | QQGHSFPLT (SEQ ID NO: 6) |
| 1C10 | QSI......SDH (SEQ ID NO: 34) | YA.......S (SEQ ID NO: 35) | QQGHSFPLT (SEQ ID NO: 6) |
| 1C12 | QSI......SDH (SEQ ID NO: 34) | YA.......S (SEQ ID NO: 35) | QQGHSFPLT (SEQ ID NO: 6) |
| 1D10 | QSI......SDH (SEQ ID NO: 34) | YA.......S (SEQ ID NO: 35) | QQGHSFPLT (SEQ ID NO: 6) |
| 1E11 | QSI......SDH (SEQ ID NO: 34) | YA.......S (SEQ ID NO: 35) | QQGHSFPLT (SEQ ID NO: 6) |
| 1E11 N103D | QSI......SDH (SEQ ID NO: 34) | YA.......S (SEQ ID NO: 35) | QQGHSFPLT (SEQ ID NO: 6) |
| 1G12 | QSI......SDH (SEQ ID NO: 34) | YA.......S (SEQ ID NO: 35) | QQGHSFPLT (SEQ ID NO: 6) |
| 1E11.C1 | QSI......SDH (SEQ ID NO: 34) | YA.......S (SEQ ID NO: 35) | QQGHSFPLT (SEQ ID NO: 6) |

TABLE 2B-continued

VL CDR sequences from antibody clones that
bind and neutralize TLR4

| Clone ID | Light CDR1 | Light CDR2 | Light CDR3 |
|---|---|---|---|
| 1E11.C2 | QSI......SDH (SEQ ID NO: 34) | YA.......S (SEQ ID NO: 35) | QQGHSFPLT (SEQ ID NO: 6) |
| 1E11.C3 | QSI......SDH (SEQ ID NO: 34) | YA.......S (SEQ ID NO: 35) | QQGHSFPLT (SEQ ID NO: 6) |
| 1E11.C4 | QSI......SDH (SEQ ID NO: 34) | YA.......S (SEQ ID NO: 35) | QQGHSFPLT (SEQ ID NO: 6) |
| 1E11.C5 | QSI......SDH (SEQ ID NO: 34) | YA.......S (SEQ ID NO: 35) | QQGHSFPLT (SEQ ID NO: 6) |
| 1E11.C6 | QSI......SDH (SEQ ID NO: 34) | YA.......S (SEQ ID NO: 35) | QQGHSFPLT (SEQ ID NO: 6) |
| 1E11.E1 | QSI......SDH (SEQ ID NO: 34) | YA.......S (SEQ ID NO: 35) | QQGNDFPVT (SEQ ID NO: 37) |
| 1E11.E2 | QSI......SDH (SEQ ID NO: 34) | YA.......S (SEQ ID NO: 35) | QQGYDEPFT (SEQ ID NO: 38) |
| 1E11.E3 | QSI......SDH (SEQ ID NO: 34) | YA.......S (SEQ ID NO: 35) | QQGYDFPLT (SEQ ID NO: 39) |
| 1E11.E4 | QSI......SDH (SEQ ID NO: 34) | YA.......S (SEQ ID NO: 35) | QQGYDYPLT (SEQ ID NO: 40) |
| 1E11.E5 | QSI......SDH (SEQ ID NO: 34) | YA.......S (SEQ ID NO: 35) | QQGYEFPLT (SEQ ID NO: 41) |
| 1E11.C2E1 | QSI......SDH (SEQ ID NO: 34) | YA.......S (SEQ ID NO: 35) | QQGNDFPVT (SEQ ID NO: 37) |
| 1E11.C2E3 | QSI......SDH (SEQ ID NO: 34) | YA.......S (SEQ ID NO: 35) | QQGYDFPLT (SEQ ID NO: 39) |
| 1E11.C2E4 | QSI......SDH (SEQ ID NO: 34) | YA.......S (SEQ ID NO: 35) | QQGYDYPLT (SEQ ID NO: 40) |
| 1E11.C2E5 | QSI......SDH (SEQ ID NO: 34) | YA.......S (SEQ ID NO: 35) | QQGYEFPLT (SEQ ID NO: 41) |

TLR4 antibodies of the invention include, for example, antibodies having the combination of heavy chain and light chain sequences shown below.

Exemplary antibodies of the invention include, for example, the anti-TLR4 antibodies described in PCT/IB2005/004206, filed Jun. 14, 2005 and published as WO 2007/110678, the anti-TLR4 antibodies described in PCT application PCT/M2008/003978, filed May 14, 2008 and published as WO 2009/101479, the contents of each of which are hereby incorporated by reference in their entirety, and commercially available antibodies such as HTA125.

Exemplary antibodies of the invention include, for example, the antibody referred to herein as NI-0101, which is also referred to herein and in the Figures as "hu15C1," which binds the human TLR4/MD2 complex and also binds TLR4 independently of the presence of MD-2. The sequences of the N1-0101 (hu15c1) antibody are shown below, with the CDR sequences underlined in the VH and VL amino acid sequences:

NI-0101 heavy chain nucleotide sequence:
(SEQ ID NO: 11)
ATGGGATGGAGCTGGATCTTTCTCTTCCTCCTGTCAGGAACTGCAGGTGT

ACATTGCCAGGTGCAGCTTCAGGAGTCCGGCCCAGGACTGGTGAAGCCTT

-continued

CGGACACCCTGTCCCTCACCTGCGCTGTCTCTGGTTACTCCATCACCGGT

GGTTATAGCTGGCACTGGATACGGCAGCCCCCAGGGAAGGGACTGGAGTG

GATGGGGTATATCCACTACAGTGGTTACACTGACTTCAACCCCTCCCTCA

AGACTCGAATCACCATATCACGTGACACGTCCAAGAACCAGTTCTCCCTG

AAGCTGAGCTCTGTGACCGCTGTGGACACTGCAGTGTATTACTGTGCGAG

AAAAGATCCGTCCGACGCCTTTCCTTACTGGGGCCAAGGGACTCTGGTCA

CTGTCTCTTCCGCCTCCACCAAGGGCCCATCGGTCTTCCCCCTGGCACCC

TCCTCCAAGAGCACCTCTGGGGGCACAGCGGCCCTGGGCTGCCTGGTCAA

GGACTACTTCCCCGAACCGGTGACGGTGTCGTGGAACTCAGGCGCCCTGA

CCAGCGGCGTGCACACCTTCCCGGCTGTCCTACAGTCCTCAGGACTCTAC

TCCCTCAGCAGCGTGGTGACCGTGCCCTCCAGCAGCTTGGGCACCCAGAC

CTACATCTGCAACGTGAATCACAAGCCCAGCAACACCAAGGTGGACAAGA

GAGTTGAGCCCAAATCTTGTGACAAAACTCACACATGCCCACCGTGCCCA

GCACCTGAACTCCTGGGGGGACCGTCAGTCTTCCTCTTCCCCCCAAAACC

-continued

CAAGGACACCCTCATGATCTCCCGGACCCCTGAGGTCACATGCGTGGTGG

TGGACGTGAGCCACGAAGACCCTGAGGTCAAGTTCAACTGGTACGTGGAC

GGCGTGGAGGTGCATAATGCCAAGACAAAGCCGCGGGAGGAGCAGTACAA

CAGCACGTACCGTGTGGTCAGCGTCCTCACCGTCCTGCACCAGGACTGGC

TGAATGGCAAGGAGTACAAATGCAAGGTCTCCAGTAAAGCTTTCCCTGCC

CCCATCGAGAAAACCATCTCCAAAGCCAAAGGGCAGCCCCGAGAACCACA

GGTGTACACCCTGCCCCCATCCCGGGAGGAGATGACCAAGAACCAGGTCA

GCCTGACCTGCCTGGTCAAAGGCTTCTATCCCAGCGACATCGCCGTGGAG

TGGGAGAGCAATGGGCAGCCGGAGAACAACTACAAGACCACGCCTCCCGT

GCTGGACTCCGACGGCTCCTTCTTCCTCTATAGCAAGCTCACCGTGGACA

AGAGCAGGTGGCAGCAGGGGAACGTCTTCTCATGCTCCGTGATGCATGAG

GCTCTGCACAACCACTACACGCAGAAGAGCCTCTCCCTGTCTCCGGGTAA

ATAG

NI-0101 heavy chain amino acid sequence:
(SEQ ID NO: 9)
MGWSWIFLFLLSGTAGVHCQVQLQESGPGLVKPSDTLSLTCAVSGYSITG

GYSWHWIRQPPGKGLEWMGYIHYSGYTDFNPSLKTRITISRDTSKNQFSL

KLSSVTAVDTAVYYCARKDPSDAFPYWGQGTLVTVSSASTKGPSVFPLAP

SSKSTSGGTAALGCLVKDYFPEPVTVSWNSGALTSGVHTFPAVLQSSGLY

SLSSVVTVPSSSLGTQTYICNVNHKPSNTKVDKRVEPKSCDKTHTCPPCP

APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSSKAFPA

PIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHE

ALHNHYTQKSLSLSPGK

NI-0101 light chain nucleotide sequence:
(SEQ ID NO: 12)
ATGGAATGGAGCTGGGTCTTTCTCTTCTTCCTGTCAGTAACTACAGGTGT

CCACTCCGAAATTGTGTTGACGCAGTCTCCAGACTTTCAGTCTGTGACTC

CAAAGGAAAAAGTCACCATCACCTGCAGGGCCAGTCAGAGTATCAGCGAC

CACTTACACTGGTACCAACAGAAACCTGATCAGTCTCCCAAGCTCCTCAT

CAAATATGCTTCCCATGCCATTTCTGGGGTCCCATCGAGGTTCAGTGGCA

GTGGGTCTGGGACAGACTTCACTCTCACCATCAATAGCCTAGAGGCTGAA

GATGCTGCAACGTATTACTGTCAGCAGGGTCACAGTTTTCCGCTCACTTT

CGGCGGAGGGACCAAGGTGGAGATCAAACGTACGGTGGCTGCACCATCTG

TCTTCATCTTCCCGCCATCTGATGAGCAGTTGAAATCTGGAACTGCCTCT

GTTGTGTGCCTGCTGAATAACTTCTATCCCAGAGAGGCCAAAGTACAGTG

GAAGGTGGATAACGCCCTCCAATCGGGTAACTCCCAGGAGAGTGTCACAG

AGCAGGACAGCAAGGACAGCACCTACAGCCTCAGCAGCACCCTGACGCTG

AGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGTT

AG

NI-0101 light chain amino acid sequence:
(SEQ ID NO: 10)
MEWSWVFLFFLSVTTGVHSEIVLTQSPDFQSVTPKEKVTITCRASQSISD

HLHWYQQKPDQSPKLLIKYASHAISGVPSRFSGSGSGTDFTLTINSLEAE

DAATYYCQQGHSFPLTFGGGTKVEIKRTVAAPSVFIFPPSDEQLKSGTAS

VVCLLNNFYPREAKVQWKVDNALQSGNSQESVTEQDSKDSTYSLSSTLTL

SKADYEKHKVYACEVTHQGLSSPVTKSFNRGEC

The NI-0101 (hu15c1) antibody includes VH CDRs having the sequences GGYSWH (SEQ ID NO: 1), YIHYSGYTDFNPSLKT (SEQ ID NO: 2), and KDPSDAFPY (SEQ ID NO: 3), and VL CDRs having the sequences RASQSISDHLH (SEQ ID NO: 4), YASHAIS (SEQ ID NO: 5) and QQGHSFPLT (SEQ ID NO: 6).

The amino acid and nucleic acid sequences of the heavy chain variable (VH) and light chain variable (VL) regions of the anti-TLR4/MD2 antibodies are shown below. The amino acids encompassing the complementarity determining regions (CDR) as defined by Chothia et al. 1989, E. A. Kabat et al., 1991 are highlighted in underlined and italicized text below. (See Chothia, C, et al., Nature 342:877-883 (1989); Kabat, E A, et al., Sequences of Protein of immunological interest, Fifth Edition, US Department of Health and Human Services, US Government Printing Office (1991)).

Anti-TLR4 antibodies include the antibodies described in co-pending U.S. application Ser. No. 11/009,939, filed Dec. 10, 2004 and Ser. No. 11/151,916, filed Jun. 15, 2004 and in WO 05/065015, filed Dec. 10, 2004 and PCT/US2005/020930, filed Jun. 15, 2004, each of which is hereby incorporated by reference in its entirety. Several exemplary antibodies include the antibodies referred to therein as 18H10, 1607, 15C1 and 7E3.

Anti-TLR4 antibodies include the antibodies described in co-pending U.S. application Ser. No. 11/151,916, filed Jun. 15, 2004 (U.S. Patent Publication No. US 2008-0050366 A1) and in PCT/M2005/004206, filed Jun. 15, 2004 (PCT Publication No. WO 07/110678), each of which is hereby incorporated by reference in its entirety. The sequences of several exemplary antibodies are shown below.

15C1 Hu V$_H$ version 4-28

(SEQ ID NO: 42)
QVQLQESGPGLVKPSDTLSLTCAVSGYSIX$_1$ GGYSWH WIRQPPGKGLEWX$_2$G YIHYSGYTDFNPSLKT RX$_3$

TX$_4$SRDTSKNQFSLKLSSVTAVDTAVYYCAR KDPSDGFPY WGQGTLVTVSS

CDR 1: GGYSWH (SEQ ID NO: 1)
CDR 2: YIHYSGYTDFNPSLKT (SEQ ID NO: 2)
CDR 3: KDPSDGFPY (SEQ ID NO: 138)

Where X₁ is Thr or Ser
Where X₂ is Ile or Met
Where X₄ is Met or Ile

15Cl Hu V<sub>H</sub> version 3-66
_____

(SEQ ID NO: 43)
EVQLVESGGGLVQPGGSLRLSCAX₁SGYSIT`GGYSWH`WVRQAPGKGLEWX₂S`YIHYSGYTDFNPSLKT`RFT

ISRDNSKNTX₃YLQMNSLRAEDTAVYYCAR`KDPSDGFPY`WGQGTLVTSS

CDR 1: GGYSWH (SEQ ID NO: 1)
CDR 2: YIHYSGYTDFNPSLKT (SEQ ID NO: 2)
CDR 3: KDPSKGFPY (SEQ ID NO: 138)
Where X₁ is Ala or Val
Where X₂ is Val or Met
Where X₃ is Leu or Phe 15Cl Hu VL version L6
_____

(SEQ ID NO: 44)
EIVLTQSPATLSLSPGERATLSC`RASQSISDHLH`WYQQKPGQAPRLLIX₁`YASHAIS`GIRARFSGSGSGT

DFTLTISSLEPEDFAVYYC`QNGHSFPLT`FGGGTKVEIK

CDR1: RASQSISDHLH (SEQ ID NO: 4)
CDR2: YASHAIS (SEQ ID NO: 5)
CDR3: QNGHSFPLT (SEQ ID NO: 139)
Where X₁ is Lys or Tyr 15Cl Hu VL version A26
_____

(SEQ ID NO: 45)
EIVLTQSPDFQSVTPKEKVTITC`RASQSISDHLH`WYQQKPDQSPKLLIK`YASHAIS`GVPSRFSGSGSGTD

FTLTINSLEAEDAATYYC`QNGHSFPLT`FGGGTKVEIK

CDR1: RASQSISDHLH (SEQ ID NO: 4)
CDR2: YASHAIS (SEQ ID NO: 5)
CDR3: QNGHSFPLT (SEQ ID NO: 139)

18H10 Hu VH version 1-69
_____

(SEQ ID NO: 46)
QVQLVQSGAEVKKPGSSVKVSCKASGFNIK`DSYIH`WVRQAPGQGLEWX₁G`WTDPENVNSIYDPRFQG`RVT

ITADX₂STSTAYX₃ELSSLRSEDTAVYYCAR`GYNGVYYAMDY`WGQGTTVTVSS

CDR1: DSYIH (SEQ ID NO: 47)
CDR2: WTDPENVNSIYDPRFQG (SEQ ID NO: 48)
CDR3: GYNGVYYAMDY (SEQ ID NO: 49)
Where X₁ is Met or Ile
Where X₂ is Lys or Thr
Where X₃ is Met or Leu 18H10 Hu VL version L6
_____

(SEQ ID NO: 50)
EIVLTQSPATLSLSPGERATLSC`SASSSVIYMH`WYQQKPGQAPRLLIY`RTYNLAS`GIPARFSGSGSGTDX₁

TLTISSLEPEDFAVYYC`HQWSSFPYT`FGQGTKVEIK

CDR1: SASSSVIYMH (SEQ ID NO: 51)
CDR2: RTYNLAS (SEQ ID NO: 52)
CDR3: HQWSSFPYT (SEQ ID NO: 53)
Where X₁ is Phe or Tyr -continued 7E3 Hu VH version 2-70

(SEQ ID NO: 54)
QVTLRESGPALVKPTQTLTLTCTFSGFSLX₁TYNIGVGWIRQPPGKALEWLAHIWWNDNIYYNTVLKSRL

TX₂SKDTSDNQVVLTMTNMDPVDTATYYCX₃RMAEGRYDAMDYWGQGTLVTVSS

CDR1: TYNIGVG (SEQ ID NO: 55)
CDR2: HIWWNDNIYYNTVLKS (SEQ ID NO: 56)
CDR3: MAEGRYDAMDY (SEQ ID NO: 57)
Where X₁ is Ser or Thr
Where X₂ is Ile or Phe
Where X₃ is Ile or Ala 7E3 Hu VH version 3-66

(SEQ ID NO: 58)
EVQLVESGGGLVQPGGSLRLSCAX₁SGFSLTTYNIGVGWVRQAPGKGLEWX₂SHIWWNDNIYYNTVLKSRL

TX₃SX₄DNSKNTX₅YLQMNSLRAEDTAVYYCX₆RMAEGRYDAMDYWGQGTLVTVSS

CDR1: TYNIGVG (SEQ ID NO: 59)
CDR2: HIWWNDNIYYNTVLKS (SEQ ID NO: 60)
CDR3: MAEGRYDAMDY (SEQ ID NO: 61)
Where X₁ is Phe or Ala
Where X₂ is Val or Leu
Where X₃ is Ile or Phe
Where X₄ is Lys or Arg
Where X₅ is Leu or Val
Where X₆ is Ile or Ala 7E3 Hu VL version L19

(SEQ ID NO: 62)
DIQMTQSPSSVSASVGDRVTITCRASQDITNYLNWYQQKPGKAPKLLIYYTSKLHSGVPSRFSGSGSGTD

X₁TLTISSLQPEDFATYX₂CQQGNTFPWTFGGGTKVEIK

CDR1: RASQDITNYLN (SEQ ID NO: 63)
CDR2: YTSKLHS (SEQ ID NO: 64)
CDR3: QQGNTFPWT (SEQ ID NO: 65)
Where X₁ is Phe or Tyr
Where X₂ is Tyr or Phe Anti-TLR4 antibodies include the antibodies described in PCT/IB2008/003978, filed May 14, 2008 (PCT Publication No. WO 2009/101479), the contents of which are hereby incorporated by reference in their entirety. These anti-TLR4 antibodies are modified to include one or more mutations in the CDR3 portion. The sequences of several exemplary antibodies are shown below.

15C1 humanized VH mutant 1 amino acid sequence:
(SEQ ID NO: 7)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

PSDAFPYWGQGTLVTVSS

15C1 humanized VH mutant 1 nucleic acid sequence:
(SEQ ID NO: 66)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

CCGTCCGACGCCTTTCCTTACTGGGGCCAAGGGACTCTGGTCACTGTCTC

TTCC

15C1 humanized VH mutant 2 amino acid sequence:
(SEQ ID NO: 67)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

PSEGFPYWGQGTLVTVSS

15C1 humanized VH mutant 2 nucleic acid sequence:
(SEQ ID NO: 68)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

```
GCTCTGTGACCGCTGTGGACACTGCAGTGTATTACTGTGCGAGAAAAGAT

CCGTCCGAGGGATTTCCTTACTGGGGCCAAGGGACTCTGGTCACTGTCTC

TTCC

15C1 humanized VL mutant 1 amino acid sequence:
                                      (SEQ ID NO: 69)
EIVLTQSPDFQSVTPKEKVTITCRASQSISDHLHWYQQKPDQSPKLLIKY

ASHAISGVPSRFSGSGSGTDFTLTINSLEAEDAATYYCQNSHSFPLTFGG

GTKVEIK

15C1 humanized VL mutant 1 nucleic acid sequence:
                                      (SEQ ID NO: 70)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGAATAGTCACAGTTTTCCGCTCACTTTCGGCGGA

GGGACCAAGGTGGAGATCAAA

15C1 humanized VL mutant 2 amino acid sequence:
                                      (SEQ ID NO: 8)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

15C1 humanized VL mutant 2 nucleic acid sequence:
                                      (SEQ ID NO: 71)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

15C1 humanized VL mutant 3 amino acid sequence:
                                      (SEQ ID NO: 72)
EIVLTQSPDFQSVTPKEKVTITCRASQSISDHLHWYQQKPDQSPKLLIKY

ASHAISGVPSRFSGSGSGTDFTLTINSLEAEDAATYYCQNSSSFPLTFGG

GTKVEIK

15C1 humanized VL mutant 3 nucleic acid sequence:
                                      (SEQ ID NO: 73)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGAATAGTAGTAGTTTTCCGCTCACTTTCGGCGGA

GGGACCAAGGTGGAGATCAAA

15C1 humanized VL mutant 4 amino acid sequence:
                                      (SEQ ID NO: 74)
EIVLTQSPDFQSVTPKEKVTITCRASQSISDHLHWYQQKPDQSPKLLIKY

ASHAISGVPSRFSGSGSGTDFTLTINSLEAEDAATYYCQQSHSFPLTFGG

GTKVEIK

15C1 humanized VL mutant 4 nucleic acid sequence:
                                      (SEQ ID NO: 75)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGAGTCACAGTTTTCCGCTCACTTTCGGCGGA

GGGACCAAGGTGGAGATCAAA
```

Antibodies of the invention interfere with or otherwise antagonize signaling via human and/or cynomolgus monkey TLR4 and/or human and/or cynomolgus monkey TLR4/MD-2 complexes. In some embodiments, the antibody binds to an epitope that includes one or more amino acid residues on human and/or cynomolgus monkey TLR4 having the following sequences:

```
>Human TLR4 amino acid sequence
                                      (SEQ ID NO: 76)
MMSASRLAGTLIPAMAFLSCVRPESWEPCVEVVPNITYQCMELNFYKIPD

NLPFSTKNLDLSFNPLRHLGSYSFFSFPELQVLDLSRCEIQTIEDGAYQS

LSHLSTLILTGNPIQSLALGAFSGLSSLQKLVAVETNLASLENFPIGHLK

TLKELNVAHNLIQSFKLPEYFSNLTNLEHLDLSSNKIQSIYCTDLRVLHQ

MPLLNLSLDLSLNPMNFIQPGAFKEIRLHKLTLRNNFDSLNVMKTCIQGL

AGLEVHRLVLGEFRNEGNLEKFDKSALEGLCNLTIEEFRLAYLDYYLDDI

IDLFNCLTNVSSFSLVSVTIERVKDFSYNFGWQHLELVNCKFGQFPTLKL

KSLKRLTFTSNKGGNAFSEVDLPSLEFLDLSRNGLSFKGCCSQSDFGTTS

LKYLDLSFNGVITMSSNFLGLEQLEHLDFQHSNLKQMSEFSVFLSLRNLI

YLDISHTHTRVAFNGIFNGLSSLEVLKMAGNSFQENFLPDIFTELRNLTF

LDLSQCQLEQLSPTAFNSLSSLQVLNMSHNNFFSLDTFPYKCLNSLQVLD

YSLNHIMTSKKQELQHFPSSLAFLNLTQNDFACTCEHQSFLQWIKDQRQL

LVEVERMECATPSDKQGMPVLSLNITCQMNKTIIGVSVLSVLVVSVVAVL

VYKFYFHLMLLAGCIKYGRGENIYDAFVIYSSQDEDWVRNELVKNLEEGV

PPFQLCLHYRDFIPGVAIAANIIHEGFHKSRKVIVVVSQHFIQSRWCIFE

YEIAQTWQFLSSRAGIIFIVLQKVEKTLLRQQVELYRLLSRNTYLEWEDS

VLGRHIFWRRLRKALLDGKSWNPEGTVGTGCNWQEATSI

>Cynomolgus monkey TLR4 amino acid sequence 1
                                      (SEQ ID NO: 77)
MTSALRLAGTLIPAMAFLSCVRPESWEPCVEVVPNITYQCMELKFYKIPD

NIPFSTKNLDLSFNPLRHLGSYSFLRFPELQVLDLSRCEIQTIEDGAYQS

LSHLSTLILTGNPIQSLALGAFSGLSSLQKLVAVETNLASLENFPIGHLK

TLKELNVAHNLIQSFKLPEYFSNLTNLEHLDLSSNKIQNIYCKDLQVLHQ
```

-continued
```
MPLSNLSLDLSLNPINFIQPGAFKEIRLHKLTLRSNFDDLNVMKTCIQGL

AGLEVHRLVLGEFRNERNLEEFDKSSLEGLCNLTIEEFRLTYLDCYLDNI

IDLFNCLANVSSFSLVSVNIKRVEDFSYNFRWQHLELVNCKFEQFPTLEL

KSLKRLTFTANKGGNAFSEVDLPSLEFLDLSRNGLSFKGCCSQSDFGTTS

LKYLDLSFNDVITMSSNFLGLEQLEHLDFQHSNLKQMSQFSVFLSLRNLI

YLDISHTHTRVAFNGIFDGLLSLKVLKMAGNSFQENFLPDIFTDLKNLTF

LDLSQCQLEQLSPTAFDTLNKLQVLNMSHNNFFSLDTFPYKCLPSLQVLD

YSLNHIMTSNNQELQHFPSSLAFLNLTQNDFACTCEHQSFLQWIKDQRQL

LVEAERMECATPSDKQGMPVLSLNITCQMNKTIIGVSVFSVLVVSVVAVL

VYKFYPHLMLLAGCIKYGRGENIYDAFVIYSSQDEDWVRNELVKNLEEGV

PPFQLCLHYRDFIPGVAIAANIIHEGFHKSRKVIVVVSQHFIQSRWCIFE

YEIAQTWQFLSSRAGIIFIVLQKVEKTLLRQQVELYRLLSRNTYLEWEDS

VLGQHIFWRRLRKALLDGKSWNPEEQ
```

Antibodies of the invention interfere with or otherwise antagonize signaling via human and/or cynomolgus monkey TLR4 and/or human and/or cynomolgus monkey TLR4/MD-2 complexes. In some embodiments, the antibody binds to an epitope that includes one or more amino acid residues on human and/or cynomolgus monkey TLR4 between residues 289 and 375 of SEQ ID NO: 76 (human TLR4) and/or SEQ ID NO: 77 (cynomolgus TLR4). For example, TLR4 antibodies specifically bind to an epitope that includes residue 349 of SEQ ID NO: 76 (human) and/or SEQ ID NO: 77 (cynomolgus). In some embodiments, the epitope also includes additional residues, for example, residues selected from the group consisting of at least residues 328 and 329 of SEQ ID NO: 76 (human) and/or SEQ ID NO: 77 (cynomolgus); at least residue 351 of SEQ ID NO: 76 (human) and/or SEQ ID NO: 77 (cynomolgus); and at least residues 369 through 371 of SEQ ID NO: 76 (human) and/or SEQ ID NO: 77 (cynomolgus), and any combination thereof.

In some embodiments, the invention provides an isolated antibody that specifically binds Toll-like receptor 4 (TLR4), wherein the antibody binds to an epitope that includes at least residue 349 of SEQ ID NO: 76 and an epitope that includes at least residue 349 of SEQ ID NO; 76. In some embodiments, the antibody includes a heavy chain with three complementarity determining regions (CDRs) including a variable heavy chain complementarity determining region 1 (CDRH1) amino acid sequence of GYSITGGYS (SEQ ID NO: 15); a variable heavy chain complementarity determining region 2 (CDRH2) amino acid sequence of IHYSGYT (SEQ ID NO: 22); and a variable heavy chain complementarity determining region 3 (CDRH3) amino acid sequence of ARKDSG($X_1$)($X_2$)($X_3$)PY (SEQ ID NO: 14), where $X_1$ is N, Q, D or E, $X_2$ is any hydrophobic amino acid, and $X_3$ is any hydrophobic amino acid; and a light chain with three CDRs including a variable light chain complementarity determining region 1 (CDRL1) amino acid sequence of QSISDH (SEQ ID NO: 34); a variable light chain complementarity determining region 2 (CDRL2) amino acid sequence of YAS (SEQ ID NO: 35); and a variable light chain complementarity determining region 3 (CDRL3) amino acid sequence of QQGHSFPLT (SEQ ID NO: 6). In some embodiments, the epitope further includes at least residues 328 and 329 of SEQ ID NO: 76 and SEQ ID NO: 76. In some embodiments, the epitope further includes at least residue 351 of SEQ ID NO: 76 and SEQ ID NO: 76.

In some embodiments, the epitope further includes one or more residues between residues 369 through 371 of SEQ ID NO: 76 and SEQ ID NO: 76. In some embodiments, the epitope further includes at least residues 369 through 371 of SEQ ID NO: 76 and SEQ ID NO: 76. In some embodiments, the antibody specifically binds to an epitope that includes at least residues 328, 329, 349, 351 and 369 through 371 of SEQ ID NO:76 and SEQ ID NO: 76. In some embodiments, the antibody further includes an amino acid substitution in the gamma heavy chain constant region at EU amino acid position 325 and an amino acid substitution at EU amino acid position 328. In some embodiments, the amino acid substituted at EU amino acid position 325 is serine, and wherein the amino acid substituted at EU amino acid position 328 is phenylalanine.

An exemplary TLR4 monoclonal antibody is the 1E11 antibody described herein. As shown below, the 1E11 antibody includes a heavy chain variable region (SEQ ID NO: 78) encoded by the nucleic acid sequence shown in SEQ ID NO: 79, and a light chain variable region (SEQ ID NO: 8) encoded by the nucleic acid sequence shown in SEQ ID NO:80.

>1E11 VH nucleic acid sequence
(SEQ ID NO: 79)
```
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC
```

>1E11 VH amino acid sequence
(SEQ ID NO: 78)
```
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGNYFPYWGQGTLVTVSS
```

>1E11 VL nucleic acid sequence
(SEQ ID NO: 80)
```
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA
```

>1E11 VL amino acid sequence
(SEQ ID NO: 8)
```
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK
```

The amino acids encompassing the complementarity determining regions (CDR) are as defined by M. P. Lefranc (See Lefranc, M.-P., Current Protocols in Immunology, J.

Wiley and Sons, New York supplement 40, A1.P.1-A.1P.37 (2000) LIGM:230). The heavy chain CDRs of the 1E11 antibody have the following sequences: GYSITGGYS (SEQ ID NO: 15); IHYSGYT (SEQ ID NO: 22); and ARKDS-GNYFPY (SEQ ID NO: 24). The light chain CDRs of the 1E11 antibody have the following sequences: QSISDH (SEQ ID NO: 34); YAS (SEQ ID NO: 35); and QQGHSFPLT (SEQ ID NO: 6).

An exemplary TLR4 monoclonal antibody is the 1A1 antibody described herein. As shown below, the 1A1 antibody includes a heavy chain variable region (SEQ ID NO: 82) encoded by the nucleic acid sequence shown in SEQ ID NO: 81, and a light chain variable region (SEQ ID NO: 8) encoded by the nucleic acid sequence shown in SEQ ID NO: 80.

>1A1 VH nucleic acid sequence
(SEQ ID NO: 81)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCCGGCCGCCTCCTCCCTTACTGGGGCCAAGGGACTCTGGTCACTGTCTC

TTCC

>1A1 VH amino acid sequence
(SEQ ID NO: 82)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGRLLPYWGQGTLVTSS

>1A1 VL nucleic acid sequence
(SEQ ID NO: 80)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1A1 VL amino acid sequence
(SEQ ID NO: 8)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1A1 antibody have the following sequences: GYSITGGYS (SEQ ID NO: 15); IHYSGYT (SEQ ID NO: 22); and ARKDS-GRLLPY (SEQ ID NO: 25). The light chain CDRs of the 1A1 antibody have the following sequences: QSISDH (SEQ ID NO: 34); YAS (SEQ ID NO: 35); and QQGHSFPLT (SEQ ID NO: 6).

An exemplary TLR4 monoclonal antibody is the 1A6 antibody described herein. As shown below, the 1A6 antibody includes a heavy chain variable region (SEQ ID NO: 84) encoded by the nucleic acid sequence shown in SEQ ID NO: 83, and a light chain variable region (SEQ ID NO: 8) encoded by the nucleic acid sequence shown in SEQ ID NO: 80.

>1A6 VH nucleic acid sequence
(SEQ ID NO: 83)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

AGCGGCAAGTGGTTGCCTTACTGGGGCCAAGGGACTCTGGTCACTGTCTC

TTCC

>1A6 VH amino acid sequence
(SEQ ID NO: 84)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGKWLPYWGQGTLVTSS

>1A6 VL nucleic acid sequence
(SEQ ID NO: 80)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1A6 VL amino acid sequence
(SEQ ID NO: 8)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1A6 antibody have the following sequences: GYSITGGYS (SEQ ID NO: 15); IHYSGYT (SEQ ID NO: 22); and ARKDS-GKWLPY (SEQ ID NO: 26). The light chain CDRs of the 1A6 antibody have the following sequences: QSISDH (SEQ ID NO: 34); YAS (SEQ ID NO: 35); and QQGHSFPLT (SEQ ID NO: 6).

An exemplary TLR4 monoclonal antibody is the 1B12 antibody described herein. As shown below, the 1B12 antibody includes a heavy chain variable region (SEQ ID NO: 86) encoded by the nucleic acid sequence shown in SEQ ID NO: 85, and a light chain variable region (SEQ ID NO: 8) encoded by the nucleic acid sequence shown in SEQ ID NO: 80.

>1B12 VH nucleic acid sequence
(SEQ ID NO: 85)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

AGCGGGCACCTCATGCCTTACTGGGGCCAAGGGACTCTGGTCACTGTCTC

TTCC

>1B12 VH amino acid sequence
(SEQ ID NO: 86)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGHLMPYWGQGTLVTVSS

>1B12 VL nucleic acid sequence
(SEQ ID NO: 80)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1B12 VL amino acid sequence
(SEQ ID NO: 8)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1A6 antibody have the following sequences: GYSITGGYS (SEQ ID NO: 15); IHYSGYT (SEQ ID NO: 22); and ARKDS-GHLMPY (SEQ ID NO: 27). The light chain CDRs of the 1B12 antibody have the following sequences: QSISDH (SEQ ID NO: 34); YAS (SEQ ID NO: 35); and QQGHSF-PLT (SEQ ID NO: 6).

An exemplary TLR4 monoclonal antibody is the 1C7 antibody described herein. As shown below, the 1C7 antibody includes a heavy chain variable region (SEQ ID NO: 88) encoded by the nucleic acid sequence shown in SEQ ID NO: 87, and a light chain variable region (SEQ ID NO: 8) encoded by the nucleic acid sequence shown in SEQ ID NO: 80.

> 1C7 VH nucleic acid sequence
(SEQ ID NO: 87)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCCGGGCACAACTACCCTTACTGGGGCCAAGGGACTCTGGTCACTGTCTC

TTCC

>1 C7 VH amino acid sequence
(SEQ ID NO: 88)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGHNYPYWGQGTLVTVSS

>1 C7 VL nucleic acid sequence
(SEQ ID NO: 80)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1 C7 VL amino acid sequence
(SEQ ID NO: 8)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1C7 antibody have the following sequences: GYSITGGYS (SEQ ID NO: 15); IHYSGYT (SEQ ID NO: 22); and ARKDS-GHNYPY (SEQ ID NO: 28). The light chain CDRs of the 1C7 antibody have the following sequences: QSISDH (SEQ ID NO: 34); YAS (SEQ ID NO: 35); and QQGHSFPLT (SEQ ID NO: 6).

An exemplary TLR4 monoclonal antibody is the 1C10 antibody described herein. As shown below, the 1C10 antibody includes a heavy chain variable region (SEQ ID NO: 90) encoded by the nucleic acid sequence shown in SEQ ID NO: 89, and a light chain variable region (SEQ ID NO: 8) encoded by the nucleic acid sequence shown in SEQ ID NO:80.

>1C10 VH nucleic acid sequence
(SEQ ID NO: 89)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

-continued
GCTCTGTGACCGCTGTGGACACTGCAGTGTATTACTGTGCGAGAAAAGAT

AGCGGCAAGAACTTCCCTTACTGGGGCCAAGGGACTCTGGTCACTGTCTC

TTCC

>1C10 VH amino acid sequence
(SEQ ID NO: 90)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGKNFPYWGQGTLVTVSS

>1C10 VL nucleic acid sequence
(SEQ ID NO: 80)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1C10 VL amino acid sequence
(SEQ ID NO: 8)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1C10 antibody have the following sequences: GYSITGGYS (SEQ ID NO: 15); IHYSGYT (SEQ ID NO: 22); and ARKDSGKNFPY (SEQ ID NO: 29). The light chain CDRs of the 1C10 antibody have the following sequences: QSISDH (SEQ ID NO: 34); YAS (SEQ ID NO: 35); and QQGHSFPLT (SEQ ID NO: 6).

An exemplary TLR4 monoclonal antibody is the 1C12 antibody described herein. As shown below, the 1C12 antibody includes a heavy chain variable region (SEQ ID NO: 92) encoded by the nucleic acid sequence shown in SEQ ID NO: 91, and a light chain variable region (SEQ ID NO: 8) encoded by the nucleic acid sequence shown in SEQ ID NO:80.

>1C12 VH nucleic acid sequence
(SEQ ID NO: 91)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

AGCGGCAAGAACTTCCCTTACTGGGGCCAAGGGACTCTGGTCACTGTCTC

TTCC

>1C12 VH amino acid sequence
(SEQ ID NO: 92)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGQLFPYWGQGTLVTVSS

>1C12 VL nucleic acid sequence
(SEQ ID NO: 80)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1C12 VL amino acid sequence
(SEQ ID NO: 8)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1C12 antibody have the following sequences: GYSITGGYS (SEQ ID NO: 15); IHYSGYT (SEQ ID NO: 22); and ARKDSGQLFPY (SEQ ID NO: 30). The light chain CDRs of the 1C12 antibody have the following sequences: QSISDH (SEQ ID NO: 34); YAS (SEQ ID NO: 35); and QQGHSFPLT (SEQ ID NO: 6).

An exemplary TLR4 monoclonal antibody is the 1D10 antibody described herein. As shown below, the 1D10 antibody includes a heavy chain variable region (SEQ ID NO: 94) encoded by the nucleic acid sequence shown in SEQ ID NO: 93, and a light chain variable region (SEQ ID NO: 8) encoded by the nucleic acid sequence shown in SEQ ID NO:80.

> 1D10 VH nucleic acid sequence
(SEQ ID NO: 93)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

AGCGGCCACAACTTGCCTTACTGGGGCCAAGGGACTCTGGTCACTGTCTC

TTCc

> 1D10 VH amino acid sequence
(SEQ ID NO: 94)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGHNLPYWGQGTLVTVSS

> 1D10 VL nucleic acid sequence
(SEQ ID NO: 80)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

> 1D10 VL amino acid sequence
(SEQ ID NO: 8)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.IP.37 (2000) LIGM:230). The heavy chain CDRs of the 1D10 antibody have the following sequences: GYSITGGYS (SEQ ID NO: 15); IHYSGYT (SEQ ID NO: 22); and ARKDSGHNLPY (SEQ ID NO: 31). The light chain CDRs of the 1D10 antibody have the following sequences: QSISDH (SEQ ID NO: 34); YAS (SEQ ID NO: 35); and QQGHSFPLT (SEQ ID NO: 6).

An exemplary TLR4 monoclonal antibody is the 1E11 N103D antibody described herein. As shown below, the 1E11 N103D antibody includes a heavy chain variable region (SEQ ID NO: 96) encoded by the nucleic acid sequence shown in SEQ ID NO: 95, and a light chain variable region (SEQ ID NO: 8) encoded by the nucleic acid sequence shown in SEQ ID NO: 80.

>1E11 N103D VH nucleic acid sequence
(SEQ ID NO: 95)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCGACTACTTCCCTTACTGGGGCCAAGGGACTCTGGTCACTGTCTC

TTCC

>1E11 N103D VH amino acid sequence
(SEQ ID NO: 96)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGDYFPYWGQGTLVTVSS

>1E11 N103D VL nucleic acid sequence
(SEQ ID NO: 80)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1E11 N103D VL amino acid sequence
(SEQ ID NO: 8)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11 N103D antibody have the following sequences: GYSITGGYS (SEQ ID NO:15); IHYSGYT (SEQ ID NO: 22); and ARKDSGDYFPY (SEQ ID NO: 32). The light chain CDRs of the 1E11 N103D antibody have the following sequences: QSISDH (SEQ ID NO: 34); YAS (SEQ ID NO: 35); and QQGHSFPLT (SEQ ID NO: 6).

An exemplary TLR4 monoclonal antibody is the 1G12 antibody described herein. As shown below, the 1G12 antibody includes a heavy chain variable region (SEQ ID NO: 98) encoded by the nucleic acid sequence shown in SEQ ID NO: 97, and a light chain variable region (SEQ ID NO: 8) encoded by the nucleic acid sequence shown in SEQ ID NO:80.

>1G12 VH nucleic acid sequence
(SEQ ID NO: 97)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCCGGGCGGTACTGGCCTTACTGGGGCCAAGGGACTCTGGTCACTGTCTC

TTCC

>1G12 VH amino acid sequence
(SEQ ID NO: 98)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGRYWPYWGQGTLVTVSS

>1G12 VL nucleic acid sequence
(SEQ ID NO: 80)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1G12 VL amino acid sequence
(SEQ ID NO: 8)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.l-A.1P.37 (2000) LIGM:230). The heavy chain CDRs of the 1012 antibody have the following sequences: GYSITGGYS (SEQ ID NO: 15); IHYSGYT (SEQ ID NO: 22); and ARKDS-GRYWPY (SEQ ID NO: 33). The light chain CDRs of the 1E11 N103D antibody have the following sequences: QSISDH (SEQ ID NO: 34); YAS (SEQ ID NO: 35); and QQGHSFPLT (SEQ ID NO: 6).

An exemplary TLR4 monoclonal antibody is the 1E11.C1 antibody described herein. As shown below, the 1E11.C1 antibody includes a heavy chain variable region (SEQ ID NO: 100) encoded by the nucleic acid sequence shown in SEQ ID NO: 99, and a light chain variable region (SEQ ID NO: 8) encoded by the nucleic acid sequence shown in SEQ ID NO:80.

>1E11.C1 VH nucleic acid sequence
(SEQ ID NO: 99)
CAGGTGCAGCTTCAGGAGTCCGGCCCAGGACTGGTGAAGCCTTCGGACAC

CCTGTCCCTCACCTGCGCTGTCTCTGGTTTCCCGATCCGCTACGGGTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC
>1E11.C1 VH amino acid sequence
(SEQ ID NO: 100)
QVQLQESGPGLVKPSDTLSLTCAVSGFPIRYGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11.C1 VL nucleic acid sequence
(SEQ ID NO: 80)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1E11.C1 VL amino acid sequence
(SEQ ID NO: 8)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.l-A.1P.37 (2000) LIGM:230). The heavy chain CDRs of the 1E11.C1 antibody have the following sequences: GFPIRYGYS (SEQ ID NO: 16); IHYSGYT (SEQ ID NO: 22); and ARKDS-GNYFPY (SEQ ID NO: 24). The light chain CDRs of the 1E11.C1 antibody have the following sequences: QSISDH (SEQ ID NO: 34); YAS (SEQ ID NO: 35); and QQGHSF-PLT (SEQ ID NO: 6).

An exemplary TLR4 monoclonal antibody is the 1E11.C2 antibody described herein. As shown below, the 1E11.C2 antibody includes a heavy chain variable region (SEQ ID NO: 102) encoded by the nucleic acid sequence shown in SEQ ID NO: 101, and a light chain variable region (SEQ ID NO: 80) encoded by the nucleic acid sequence shown in SEQ ID NO: 8.

>1E11.C2 VH nucleic acid sequence
(SEQ ID NO: 101)
CAGGTGCAGCTTCAGGAGTCCGGCCCAGGACTGGTGAAGCCTTCGGACAC

CCTGTCCCTCACCTGCGCTGTCTCTGGTTACCCGATCCGGTTCGGCTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC

>1E11.C2 VH amino acid sequence
(SEQ ID NO: 102)
QVQLQESGPGLVKPSDTLSLTCAVSGYPIRFGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11.C2 VL nucleic acid sequence
(SEQ ID NO: 80)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1E11.C2 VL amino acid sequence
(SEQ ID NO: 8)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.l-A.1P.37 (2000) LIGM:230). The heavy chain CDRs of the 1E11.C2 antibody have the following sequences: GYPIRFGYS (SEQ ID NO: 17); IHYSGYT (SEQ ID NO: 22); and ARKDS-GNYFPY (SEQ ID NO: 24). The light chain CDRs of the 1E11.C1 antibody have the following sequences: QSISDH (SEQ ID NO: 34); YAS (SEQ ID NO: 35); and QQGHSF-PLT (SEQ ID NO: 6).

An exemplary TLR4 monoclonal antibody is the 1E11.C3 antibody described herein. As shown below, the 1E11.C3 antibody includes a heavy chain variable region (SEQ ID NO: 104) encoded by the nucleic acid sequence shown in SEQ ID NO: 103, and a light chain variable region (SEQ ID NO: 8) encoded by the nucleic acid sequence shown in SEQ ID NO:80.

>1E11.C3 VH nucleic acid sequence
(SEQ ID NO: 103)
CAGGTGCAGCTTCAGGAGTCCGGCCCAGGACTGGTGAAGCCTTCGGACAC

CCTGTCCCTCACCTGCGCTGTCTCTGGTTACCCCATCCGGCACGGGTACA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC

> 1E11.C3 VH amino acid sequence
(SEQ ID NO: 104)
QVQLQESGPGLVKPSDTLSLTCAVSGYPIRHGYSWHWIRQPPGKGLEWMG

YIHYSGYTDFNPSLKTRITISRDTSKNQFSLKLSSVTAVDTAVYYCARKD

SGNYFPYWGQGTLVTVSS

> 1E11.C3 VL nucleic acid sequence
(SEQ ID NO: 80)
GAAATTGTGTTGACGCAGTCTCCAGACTTTCAGTCTGTGACTCCAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

> 1E11.C3 VL amino acid sequence
(SEQ ID NO: 8)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, Al.P.l-A.1P.37 (2000) LIGM:230). The heavy chain CDRs of the 1E11.C3 antibody have the following sequences: GYPIRHGYS (SEQ ID NO:18); IHYSGYT (SEQ ID NO: 22); and ARKDS-GNYFPY (SEQ ID NO: 24). The light chain CDRs of the 1E11.C1 antibody have the following sequences: QSISDH (SEQ ID NO: 34); YAS (SEQ ID NO: 35); and QQGHSF-PLT (SEQ ID NO: 6).

An exemplary TLR4 monoclonal antibody is the 1E11.C4 antibody described herein. As shown below, the 1E11.C4 antibody includes a heavy chain variable region (SEQ ID NO: 1 06) encoded by the nucleic acid sequence shown in SEQ ID NO: 105, and a light chain variable region (SEQ ID NO: 8) encoded by the nucleic acid sequence shown in SEQ ID NO: 80.

> 1E11.C4 VH nucleic acid sequence
(SEQ ID NO: 105)
CAGGTGCAGCTTCAGGAGTCCGGCCCAGGACTGGTGAAGCCTTCGGACAC

CCTGTCCCTCACCTGCGCTGTCTCTGGTTTCCCGATCGGCCAGGGGTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC

>1E11.C4 VH amino acid sequence
(SEQ ID NO: 106)
QVQLQESGPGLVKPSDTLSLTCAVSGFPIGQGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11.C4 VL nucleic acid sequence
(SEQ ID NO: 80)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

> 1E11.C4 VL amino acid sequence
(SEQ ID NO: 8)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, Al.P.l-A.1P.37 (2000) LIGM:230). The heavy chain CDRs of the 1E11.C4 antibody have the following sequences: GFPIGQGYS (SEQ ID NO: 19); IHYSGYT (SEQ ID NO: 22); and ARKDSGNYFPY (SEQ ID NO: 24). The light chain CDRs of the 1E11.C1 antibody have the following sequences: QSISDH (SEQ ID NO: 34); YAS (SEQ ID NO: 35); and QQGHSFPLT (SEQ ID NO: 6).

An exemplary TLR4 monoclonal antibody is the 1E11.C5 antibody described herein. As shown below, the 1E11.C5 antibody includes a heavy chain variable region (SEQ ID NO: 108) encoded by the nucleic acid sequence shown in SEQ ID NO: 107, and a light chain variable region (SEQ ID NO: 8) encoded by the nucleic acid sequence shown in SEQ ID NO:80.

>1E11.C5 VH nucleic acid sequence
(SEQ ID NO: 107)
CAGGTGCAGCTTCAGGAGTCCGGCCCAGGACTGGTGAAGCCTTCGGACAC

CCTGTCCCTCACCTGCGCTGTCTCTGGTTACCCGATCTGGGGGGGCTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCCGCCTCCACC

>1E11.C5 VH amino acid sequence
(SEQ ID NO: 108)
QVQLQESGPGLVKPSDTLSLTCAVSGYPIWGGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11.C5 VL nucleic acid sequence
(SEQ ID NO: 80)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1E11.C5 VL amino acid sequence
(SEQ ID NO: 8)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, Al.P.l-A.1P.37 (2000) LIGM:230). The heavy chain CDRs of the 1E11.C5 antibody have the following sequences: GYPIWGGYS (SEQ ID NO:20); IHYSGYT (SEQ ID NO: 22); and ARKDSGNYFPY (SEQ ID NO: 24). The light chain CDRs of the 1E11.C1 antibody have the following sequences: QSISDH (SEQ ID NO: 34); YAS (SEQ ID NO: 35); and QQGHSFPLT (SEQ ID NO: 6).

An exemplary TLR4 monoclonal antibody is the 1E11.C6 antibody described herein. As shown below, the 1E11.C6 antibody includes a heavy chain variable region (SEQ ID NO: 110) encoded by the nucleic acid sequence shown in SEQ ID NO: 109, and a light chain variable region (SEQ ID NO: 8) encoded by the nucleic acid sequence shown in SEQ ID NO:80.

>1E11.C6 VH nucleic acid sequence
(SEQ ID NO: 109)
CAGGTGCAGCTTCAGGAGTCCGGCCCAGGACTGGTGAAGCCTTCGGACAC

CCTGTCCCTCACCTGCGCTGTCTCTGGTTACCCCATCGGCGGCGGCTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC

>1E11.C6 VH amino acid sequence
(SEQ ID NO: 110)
QVQLQESGPGLVKPSDTLSLTCAVSGYPIGGGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11.C6 VL nucleic acid sequence
(SEQ ID NO: 80)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1E11.C6 VL amino acid sequence
(SEQ ID NO: 8)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, Al.P.l-A.1P.37 (2000) LIGM:230). The heavy chain CDRs of the 1E11.C6 antibody have the following sequences: GYPIGGGYS (SEQ ID NO:21); IHYSGYT (SEQ ID NO: 22); and ARKDSGNYFPY (SEQ ID NO: 24). The light chain CDRs of the 1E11.C1 antibody have the following sequences: QSISDH (SEQ ID NO: 34); YAS (SEQ ID NO: 35); and QQGHSFPLT (SEQ ID NO: 6).

An exemplary TLR4 monoclonal antibody is the 1E11.E1 antibody described herein. As shown below, the 1E11.E1 antibody includes a heavy chain variable region (SEQ ID NO: 78) encoded by the nucleic acid sequence shown in SEQ ID NO:77, and a light chain variable region (SEQ ID NO: 112) encoded by the nucleic acid sequence shown in SEQ ID NO: 111.

>1E11.E1 VH nucleic acid sequence
(SEQ ID NO: 79)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC

>1E11.E1 VH amino acid sequence
(SEQ ID NO: 78)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11.E1 VL nucleic acid sequence
(SEQ ID NO: 111)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGGAACGACTTCCCGGTGACTTTCGGCGGA

GGGACCAAGGTGGAGATCAAA

>1E11.E1 VL amino acid sequence
(SEQ ID NO: 112)
EIVLTQSPDFQSVTPKEKVTITCRASQSISDHLHWYQQKPDQSPKLLIKY

ASHAISGVPSRFSGSGSGTDFTLTINSLEAEDAATYYCQQGNDFPVTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, Al.P.l-A.1P.37 (2000) LIGM:230). The heavy chain CDRs of the 1E11.E1 antibody have the following sequences: GYSITGGYS (SEQ ID NO: 15); IHYSGYT (SEQ ID NO: 22); and ARKDSGNYFPY (SEQ ID NO: 24). The light chain CDRs of the 1E11 antibody have the following sequences: QSISDH (SEQ ID NO: 34); YAS (SEQ ID NO: 35); and QQGNDFPVT (SEQ ID NO: 37).

An exemplary TLR4 monoclonal antibody is the 1E11.E2 antibody described herein. As shown below, the 1E11.E2 antibody includes a heavy chain variable region (SEQ ID NO: 78) encoded by the nucleic acid sequence shown in SEQ ID NO:79, and a light chain variable region (SEQ ID NO: 114) encoded by the nucleic acid sequence shown in SEQ ID NO: 113.

>1E11.E2 VH nucleic acid sequence
(SEQ ID NO: 79)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC

>1E11.E2 VH amino acid sequence
(SEQ ID NO: 78)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11.E2 VL nucleic acid sequence
(SEQ ID NO: 113)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGGTACGACGAGCCGTTCACTTTCGGCGGA

GGGACCAAGGTGGAGATCAAA

>1E11.E2 VL amino acid sequence
(SEQ ID NO: 114)
EIVLTQSPDFQSVTPKEKVTITCRASQSISDHLHWYQQKPDQSPKLLIKY

ASHAISGVPSRFSGSGSGTDFTLTINSLEAEDAATYYCQQGYDEPFTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.E2 antibody have the following sequences: GYSITGGYS (SEQ ID NO: 15); IHYSGYT (SEQ ID NO: 22); and ARKDS-GNYFPY (SEQ ID NO: 24). The light chain CDRs of the 1E11 antibody have the following sequences: QSISDH (SEQ ID NO: 34); YAS (SEQ ID NO: 35); and QQGYDEPFT (SEQ ID NO: 38).

An exemplary TLR4 monoclonal antibody is the 1E11.E3 antibody described herein. As shown below, the 1E11.E3 antibody includes a heavy chain variable region (SEQ ID NO: 78) encoded by the nucleic acid sequence shown in SEQ ID NO:79, and a light chain variable region (SEQ ID NO: 116) encoded by the nucleic acid sequence shown in SEQ ID NO: 115.

>1E11.E3 VH nucleic acid sequence
(SEQ ID NO: 79)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC

>1E11.E3 VH amino acid sequence
(SEQ ID NO: 78)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11.E3 VL nucleic acid sequence
(SEQ ID NO: 115)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGCTACGACTTCCCGTTGACTTTCGGCGGA

GGGACCAAGGTGGAGATCAAA

>1E11.E3 VL amino acid sequence
(SEQ ID NO: 116)
EIVLTQSPDFQSVTPKEKVTITCRASQSISDHLHWYQQKPDQSPKLLIKY

ASHAISGVPSRFSGSGSGTDFTLTINSLEAEDAATYYCQQGYDFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.E3 antibody have the following sequences: GYSITGGYS (SEQ ID NO: 15); IHYSGYT (SEQ ID NO: 22); and ARKDS-GNYFPY (SEQ ID NO: 24). The light chain CDRs of the 1E11 antibody have the following sequences: QSISDH (SEQ ID NO: 34); YAS (SEQ ID NO: 35); and QQGYD-FPLT (SEQ ID NO: 39).

An exemplary TLR4 monoclonal antibody is the 1E11.E4 antibody described herein. As shown below, the 1E11.E4 antibody includes a heavy chain variable region (SEQ ID NO: 79) encoded by the nucleic acid sequence shown in SEQ ID NO:79, and a light chain variable region (SEQ ID NO: 118) encoded by the nucleic acid sequence shown in SEQ ID NO: 117.

>1E11.E4 VH nucleic acid sequence
(SEQ ID NO: 79)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC

>1E11.E4 VH amino acid sequence
(SEQ ID NO: 78)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11.E4 VL nucleic acid sequence
(SEQ ID NO: 117)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGCTACGACTACCCGCTCACTTTCGGCGGA

GGGACCAAGGTGGAGATCAAA

>1E11.E4 VL amino acid sequence
(SEQ ID NO: 118)
EIVLTQSPDFQSVTPKEKVTITCRASQSISDHLHWYQQKPDQSPKLLIKY

ASHAISGVPSRFSGSGSGTDFTLTINSLEAEDAATYYCQQGYDYPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37

(2000) LIGM:230). The heavy chain CDRs of the 1E11.E4 antibody have the following sequences: GYSITGGYS (SEQ ID NO: 15); IHYSGYT (SEQ ID NO: 22); and ARKDSGNYFPY (SEQ ID NO: 24). The light chain CDRs of the 1E11 antibody have the following sequences: QSISDH (SEQ ID NO: 34); YAS (SEQ ID NO: 35); and QQGYDYPLT (SEQ ID NO: 40).

An exemplary TLR4 monoclonal antibody is the 1E11.E5 antibody described herein. As shown below, the 1E11.E5 antibody includes a heavy chain variable region (SEQ ID NO: 78) encoded by the nucleic acid sequence shown in SEQ ID NO:79, and a light chain variable region (SEQ ID NO: 120) encoded by the nucleic acid sequence shown in SEQ ID NO: 119.

>1E11.E5 VH nucleic acid sequence
(SEQ ID NO: 79)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC

>1E11.E5 VH amino acid sequence
(SEQ ID NO: 78)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11.E5 VL nucleic acid sequence
(SEQ ID NO: 119)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGCTACGAGTTCCCGTTGACTTTCGGCGGA

GGGACCAAGGTGGAGATCAAA

>1E11.E5 VL amino acid sequence
(SEQ ID NO: 120)
EIVLTQSPDFQSVTPKEKVTITCRASQSISDHLHWYQQKPDQSPKLLIKY

ASHAISGVPSRFSGSGSGTDFTLTINSLEAEDAATYYCQQGYEFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.l-A.1P.37 (2000) LIGM:230). The heavy chain CDRs of the 1E11.E5 antibody have the following sequences: GYSITGGYS (SEQ ID NO: 15); IHYSGYT (SEQ ID NO: 22); and ARKDSGNYFPY (SEQ ID NO: 24). The light chain CDRs of the 1E11 antibody have the following sequences: QSISDH (SEQ ID NO: 34); YAS (SEQ ID NO: 35); and QQGYEFPLT (SEQ ID NO: 41).

An exemplary TLR4 monoclonal antibody is the 1E11.C2E1 antibody described herein. As shown below, the 1E11.C2E1 antibody includes a heavy chain variable region (SEQ ID NO: 102) encoded by the nucleic acid sequence shown in SEQ ID NO: 101, and a light chain variable region (SEQ ID NO: 122) encoded by the nucleic acid sequence shown in SEQ ID NO: 121.

>1E11.C2E1 VH nucleic acid sequence
(SEQ ID NO: 101)
CAGGTGCAGCTTCAGGAGTCCGGCCCAGGACTGGTGAAGCCTTCGGACAC

CCTGTCCCTCACCTGCGCTGTCTCTGGTTACCCGATCCGGTTCGGCTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC

>1E11.C2E1 VH amino acid sequence
(SEQ ID NO: 102)
QVQLQESGPGLVKPSDTLSLTCAVSGYPIRFGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11.C2E1 VL nucleic acid sequence
(SEQ ID NO: 121)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGGAACGACTTCCCGGTGACTTTCGGCGGA

GGGACCAAGGTGGAGATCAAA

>1E11.C2E1 VL amino acid sequence
(SEQ ID NO: 122)
EIVLTQSPDFQSVTPKEKVTITCRASQSISDHLHWYQQKPDQSPKLLIKY

ASHAISGVPSRFSGSGSGTDFTLTINSLEAEDAATYYCQQGNDFPVTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.l-A.1P.37 (2000) LIGM:230). The heavy chain CDRs of the 1E11.C2E1 antibody have the following sequences: GYPIRFGYS (SEQ ID NO:17); IHYSGYT (SEQ ID NO: 22); and ARKDSGNYFPY (SEQ ID NO: 24). The light chain CDRs of the 1E11 antibody have the following sequences: QSISDH (SEQ ID NO: 34); YAS (SEQ ID NO: 35); and QQGNDFPVT (SEQ ID NO: 37).

An exemplary TLR4 monoclonal antibody is the 1E11.C2E3 antibody described herein. As shown below, the 1E11.C2E3 antibody includes a heavy chain variable region (SEQ ID NO: 102) encoded by the nucleic acid sequence shown in SEQ ID NO: 101, and a light chain variable region (SEQ ID NO: 124) encoded by the nucleic acid sequence shown in SEQ ID NO: 123.

>1E11.C2E3 VH nucleic acid sequence
(SEQ ID NO: 101)
CAGGTGCAGCTTCAGGAGTCCGGCCCAGGACTGGTGAAGCCTTCGGACAC

CCTGTCCCTCACCTGCGCTGTCTCTGGTTACCCGATCCGGTTCGGCTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC

>1E11.C2E3 VH amino acid sequence
(SEQ ID NO: 102)
QVQLQESGPGLVKPSDTLSLTCAVSGYPIRFGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11.C2E3 VL nucleic acid sequence
(SEQ ID NO: 123)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGCTACGACTTCCCGTTGACTTTCGGCGGA

GGGACCAAGGTGGAGATCAAA

>1E11.C2E3 VL amino acid sequence
(SEQ ID NO: 124)
EIVLTQSPDFQSVTPKEKVTITCRASQSISDHLHWYQQKPDQSPKLLIKY

ASHAISGVPSRFSGSGSGTDFTLTINSLEAEDAATYYCQQGYDFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.C2E3 antibody have the following sequences: GYPIR-FGYS (SEQ ID NO:17); IHYSGYT (SEQ ID NO: 22); and ARKDSGNYFPY (SEQ ID NO: 24). The light chain CDRs of the 1E11 antibody have the following sequences: QSISDH (SEQ ID NO: 34); YAS (SEQ ID NO: 35); and QQGYDFPLT (SEQ ID NO: 39).

An exemplary TLR4 monoclonal antibody is the 1E11.C2E4 antibody described herein. As shown below, the 1E11.C2E4 antibody includes a heavy chain variable region (SEQ ID NO: 102) encoded by the nucleic acid sequence shown in SEQ ID NO: 101, and a light chain variable region (SEQ ID NO: 126) encoded by the nucleic acid sequence shown in SEQ ID NO: 125.

>1E11.C2E4 VH nucleic acid sequence
(SEQ ID NO: 101)
CAGGTGCAGCTTCAGGAGTCCGGCCCAGGACTGGTGAAGCCTTCGGACAC

CCTGTCCCTCACCTGCGCTGTCTCTGGTTACCCGATCCGGTTCGGCTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC

>1E11.C2E4 VH amino acid sequence
(SEQ ID NO: 102)
QVQLQESGPGLVKPSDTLSLTCAVSGYPIRFGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11.C2E4 VL nucleic acid sequence
(SEQ ID NO: 125)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGCTACGACTACCCGCTCACTTTCGGCGGA

GGGACCAAGGTGGAGATCAAA

>1E11.C2E4 VL amino acid sequence
(SEQ ID NO: 126)
EIVLTQSPDFQSVTPKEKVTITCRASQSISDHLHWYQQKPDQSPKLLIKY

ASHAISGVPSRFSGSGSGTDFTLTINSLEAEDAATYYCQQGYDYPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1 P.37 (2000) LIGM:230). The heavy chain CDRs of the 1E11.C2E4 antibody have the following sequences: GYPIR-FGYS (SEQ ID NO: 17); IHYSGYT (SEQ ID NO: 22); and ARKDSGNYFPY (SEQ ID NO: 24). The light chain CDRs of the 1E11 antibody have the following sequences: QSISDH (SEQ ID NO: 34); YAS (SEQ ID NO: 35); and QQGYDYPLT (SEQ ID NO: 40).

An exemplary TLR4 monoclonal antibody is the 1E11.C2E5 antibody described herein. As shown below, the 1E11.C2E5 antibody includes a heavy chain variable region (SEQ ID NO: 102) encoded by the nucleic acid sequence shown in SEQ ID NO: 101, and a light chain variable region (SEQ ID NO: 128) encoded by the nucleic acid sequence shown in SEQ ID NO: 127.

> 1E11.C2E5 VH nucleic acid sequence
(SEQ ID NO: 101)
CAGGTGCAGCTTCAGGAGTCCGGCCCAGGACTGGTGAAGCCTTCGGACAC

CCTGTCCCTCACCTGCGCTGTCTCTGGTTACCCGATCCGGTTCGGCTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

```
GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC
```

> 1E11.C2E5 VH amino acid sequence
(SEQ ID NO: 102)
```
QVQLQESGPGLVKPSDTLSLTCAVSGYPIRFGYSWHWIRQPPGKGLEWMG

YIHYSGYTDFNPSLKTRITISRDTSKNQFSLKLSSVTAVDTAVYYCARKD

SGNYFPYWGQGTLVTVSS
```

> 1E11.C2E5 VL nucleic acid sequence
(SEQ ID NO: 127)
```
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGCTACGAGTTCCCGTTGACTTTCGGCGGA

GGGACCAAGGTGGAGATCAAA
```

>1E11.C2E5 VL amino acid sequence
(SEQ ID NO: 128)
```
EIVLTQSPDFQSVTPKEKVTITCRASQSISDHLHWYQQKPDQSPKLLIKY

ASHAISGVPSRFSGSGSGTDFTLTINSLEAEDAATYYCQQGYEFPLTFGG

GTKVEIK
```

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.IP.37 (2000) LIGM:230). The heavy chain CDRs of the 1E11.C2E5 antibody have the following sequences: GYPIRFGYS (SEQ ID NO:17); IHYSGYT (SEQ ID NO: 22); and ARKDSGNYFPY (SEQ ID NO: 24). The light chain CDRs of the 1E11 antibody have the following sequences: QSISDH (SEQ ID NO: 34); YAS (SEQ ID NO: 35); and QQGYEFPLT (SEQ ID NO: 41).

In some embodiments, the TLR4 antibodies are formatted in an IgG isotype. In some embodiments, the TLR4 antibodies are formatted in an IgG1 isotype.

An exemplary IgG1-formatted antibody is the IgG1-formatted 1E11 antibody comprising the heavy chain sequence of SEQ ID NO: 130 and the light chain sequence of SEQ ID NO: 132, as shown below:

>1E11 Heavy Chain Amino Acid Sequence
(SEQ ID NO: 130)
```
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGNYFPYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPG
```

>1E11 Light Chain Amino Acid Sequence
(SEQ ID NO: 132)
```
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

>1E11 Light Chain Nucleic Acid Sequence
(SEQ ID NO: 131)
```
ATGAGTGTGCCCACTCAGGTCCTGGGGTTGCTGCTGCTGTGGCTTACAGA

TGCCAGATGTGAAATTGTGTTGACGCAGTCTCCAGACTTTCAGTCTGTGA

CTCCAAAGGAAAAAGTCACCATCACCTGCAGGGCCAGTCAGAGTATCAGC

GACCACTTACACTGGTACCAACAGAAACCTGATCAGTCTCCCAAGCTCCT

CATCAAATATGCTTCCCATGCCATTTCTGGGGTCCCATCGAGGTTCAGTG

GCAGTGGGTCTGGGACAGACTTCACTCTCACCATCAATAGCCTAGAGGCT

GAAGATGCTGCAACGTATTACTGTCAGCAGGGTCACAGTTTTCCGCTCAC

TTTCGGCGGAGGGACCAAGGTGGAGATCAAACGTACGGTGGCTGCACCAT

CTGTCTTCATCTTCCCGCCATCTGATGAGCAGTTGAAATCTGGAACTGCC

TCTGTTGTGTGCCTGCTGAATAACTTCTATCCCAGAGAGGCCAAAGTACA

GTGGAAGGTGGATAACGCCCTCCAATCGGGTAACTCCCAGGAGAGTGTCA

CAGAGCAGGACAGCAAGGACAGCACCTACAGCCTCAGCAGCACCCTGACG

CTGAGCAAAGCAGACTACGAGAAACACAAAGTCTACGCCTGCGAAGTCAC

CCATCAGGGCCTGAGCTCGCCCGTCACAAAGAGCTTCAACAGGGGAGAGT

GTTAA
```

> 1E11 Heavy Chain Nucleic Acid Sequence
(SEQ ID NO: 129)
```
ATGGAATGGAGCTGGGTCTTTCTCTTCTTCCTGTCAGTAACTACAGGTGT

CCACCAGGTGCAGCTTCAGGAGTCCGGCCCAGGACTGGTGAAGCCTTCGG

ACACCCTGTCCCTCACCTGCGCTGTCTCTGGTTACTCCATCACCGGTGGT

TATAGCTGGCACTGGATACGGCAGCCCCCAGGGAAGGGACTGGAGTGGAT

GGGGTATATCCACTACAGTGGTTACACTGACTTCAACCCCTCCCTCAAGA

CTCGAATCACCATATCACGTGACACGTCCAAGAACCAGTTCTCCCTGAAG

CTGAGCTCTGTGACCGCTGTGGACACTGCAGTGTATTACTGTGCGAGAAA

AGATCCGTCCGACGCCTTTCCTTACTGGGGCCAAGGGACTCTGGTCACTG

TCTCTTCCGCCTCCACCAAGGGCCCATCGGTCTTCCCCCTGGCACCCTCC

TCCAAGAGCACCTCTGGGGGCACAGCGGCCCTGGGCTGCCTGGTCAAGGA

CTACTTCCCCGAACCGGTGACAGTCTCGTGGAACTCAGGAGCCCTGACCA

GCGGCGTGCACACCTTCCCGGCTGTCCTACAGTCCTCAGGACTCTACTCC

CTCAGCAGCGTGGTGACTGTGCCCTCCAGCAGCTTGGGCACCCAGACCTA

CATCTGCAACGTGAATCACAAGCCCAGCAACACCAAGGTGGACAAGAGAG

TTGAGCCCAAATCTTGTGACAAAACTCACACATGCCCACCGTGCCCAGCA

CCTGAACTCCTGGGGGGACCGTCAGTCTTCCTCTTCCCCCCAAAACCCAA

GGACACCCTCATGATCTCCCGGACCCCTGAGGTCACATGCGTGGTGGTGG
```

```
ACGTGAGCCACGAAGACCCTGAGGTCAAGTTCAACTGGTACGTGGACGGC

GTGGAGGTGCATAATGCCAAGACAAAGCCGCGGGAGGAGCAGTACAACAG

CACGTACCGTGTGGTCAGCGTCCTCACCGTCCTGCACCAGGACTGGCTGA

ATGGCAAGGAGTACAAGTGCAAGGTCTCCAACAAAGCCCTCCCAGCCCCC

ATCGAGAAAACCATCTCCAAAGCCAAAGGGCAGCCCCGAGAACCACAGGT

GTATACCCTGCCCCCATCTCGGGAGGAGATGACCAAGAACCAGGTCAGCC

TGACTTGCCTGGTCAAAGGCTTCTATCCCAGCGACATCGCCGTGGAGTGG

GAGAGCAACGGGCAGCCGGAGAACAACTACAAGACCACGCCTCCCGTGCT

GGACTCCGACGGCTCCTTCTTCCTCTATAGCAAGCTCACCGTGGACAAGT

CCAGGTGGCAGCAGGGGAACGTCTTCTCATGCTCCGTGATGCATGAGGCT

CTGCACAACCACTACACGCAGAAGAGCCTCTCCCTGTCTCCGGGTTAA
```

An exemplary IgG1-formatted antibody is the IgG1-formatted 1E11.C11 antibody comprising the heavy chain sequence of SEQ ID NO: 134 and the light chain sequence of SEQ ID NO: 136, as shown below:

```
>1E11.C1 Light Chain Amino Acid Sequence
                                    (SEQ ID NO: 136)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

> 1E11.C1 Heavy Chain Amino Acid Sequence
                                    (SEQ ID NO: 134)
QVQLQESGPGLVKPSDTLSLTCAVSGFPIRYGYSWHWIRQPPGKGLEWMG

YIHYSGYTDFNPLKTRITISRDTSKNQFSLKLSSVTAVDTAVYYCARKDS

GNYFPYWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKRVEPKSCDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPG

> 1E11.C1 Light Chain Nucleic Acid Sequence
                                    (SEQ ID NO: 135)
ATGAGTGTGCCCACTCAGGTCCTGGGGTTGCTGCTGCTGTGGCTTACAGA

TGCCAGATGTGAAATTGTGTTGACGCAGTCTCCAGACTTTCAGTCTGTGA

CTCCAAAGGAAAAAGTCACCATCACCTGCAGGGCCAGTCAGAGTATCAGC

GACCACTTACACTGGTACCAACAGAAACCTGATCAGTCTCCCAAGCTCCT

CATCAAATATGCTTCCCATGCCATTTCTGGGGTCCCATCGAGGTTCAGTG

GCAGTGGGTCTGGGACAGACTTCACTCTCACCATCAATAGCCTAGAGGCT

GAAGATGCTGCAACGTATTACTGTCAGCAGGGTCACAGTTTTCCGCTCAC

TTTCGGCGGAGGGACCAAGGTGGAGATCAAACGTACGGTGGCTGCACCAT

CTGTCTTCATCTTCCCGCCATCTGATGAGCAGTTGAAATCTGGAACTGCC

TCTGTTGTGTGCCTGCTGAATAACTTCTATCCCAGAGAGGCCAAAGTACA

GTGGAAGGTGGATAACGCCCTCCAATCGGGTAACTCCCAGGAGAGTGTCA

CAGAGCAGGACAGCAAGGACAGCACCTACAGCCTCAGCAGCACCCTGACG

CTGAGCAAAGCAGACTACGAGAAACACAAAGTCTACGCCTGCGAAGTCAC

CCATCAGGGCCTGAGCTCGCCCGTCACAAAGAGCTTCAACAGGGGAGAGT

GTTAA

> 1E11.C1 Heavy Chain Nucleic Acid Sequence
                                    (SEQ ID NO: 133)
ATGGAATGGAGCTGGGTCTTTCTCTTCTTCCTGTCAGTAACTACAGGTGT

CCACCAGGTGCAGCTTCAGGAGTCCGGCCCAGGACTGGTGAAGCCTTCGG

ACACCCTGTCCCTCACCTGCGCTGTCTCTGGTTTCCCGATCCGCTACGGG

TATAGCTGGCACTGGATACGGCAGCCCCCAGGGAAGGGACTGGAGTGGAT

GGGGTATATCCACTACAGTGGTTACACTGACTTCAACCCCTCCCTCAAGA

CTCGAATCACCATATCACGTGACACGTCCAAGAACCAGTTCTCCCTGAAG

CTGAGCTCTGTGACCGCTGTGGACACTGCAGTGTATTACTGTGCGAGAAA

AGATTCGGGCAACTACTTCCCTTACTGGGGCCAAGGGACTCTGGTCACTG

TCTCTTCCGCCTCCACCAAGGGCCCATCGGTCTTCCCCCTGGCACCCTCC

TCCAAGAGCACCTCTGGGGGCACAGCGGCCCTGGGCTGCCTGGTCAAGGA

CTACTTCCCCGAACCGGTGACAGTCTCGTGGAACTCAGGAGCCCTGACCA

GCGGCGTGCACACCTTCCCGGCTGTCCTACAGTCCTCAGGACTCTACTCC

CTCAGCAGCGTGGTGACTGTGCCCTCCAGCAGCTTGGGCACCCAGACCTA

CATCTGCAACGTGAATCACAAGCCCAGCAACACCAAGGTGGACAAGAGAG

TTGAGCCCAAATCTTGTGACAAAACTCACACATGCCCACCGTGCCCAGCA

CCTGAACTCCTGGGGGGACCGTCAGTCTTCCTCTTCCCCCCAAAACCCAA

GGACACCCTCATGATCTCCCGGACCCCTGAGGTCACATGCGTGGTGGTGG

ACGTGAGCCACGAAGACCCTGAGGTCAAGTTCAACTGGTACGTGGACGGC

GTGGAGGTGCATAATGCCAAGACAAAGCCGCGGGAGGAGCAGTACAACAG

CACGTACCGTGTGGTCAGCGTCCTCACCGTCCTGCACCAGGACTGGCTGA

ATGGCAAGGAGTACAAGTGCAAGGTCTCCAACAAAGCCCTCCCAGCCCCC

ATCGAGAAAACCATCTCCAAAGCCAAAGGGCAGCCCCGAGAACCACAGGT

GTATACCCTGCCCCCATCTCGGGAGGAGATGACCAAGAACCAGGTCAGCC

TGACTTGCCTGGTCAAAGGCTTCTATCCCAGCGACATCGCCGTGGAGTGG

GAGAGCAACGGGCAGCCGGAGAACAACTACAAGACCACGCCTCCCGTGCT

GGACTCCGACGGCTCCTTCTTCCTCTATAGCAAGCTCACCGTGGACAAGT

CCAGGTGGCAGCAGGGGAACGTCTTCTCATGCTCCGTGATGCATGAGGCT

CTGCACAACCACTACACGCAGAAGAGCCTCTCCCTGTCTCCGGGTTAA
```

In some embodiments, TLR4 antibodies of the invention specifically bind human and/or cynomolgus TLR4/MD-2 complex, wherein the antibody binds to an epitope that includes one or more amino acid residues on human and/or cynomolgus TLR4 between residues 325 and 374 of SEQ ID NO: 76 (human) and SEQ ID NO: 77 (cynomolgus). Alternatively, the monoclonal antibody is an antibody that binds to the same epitope as 1A1, 1A6, 1B12, 1C7, 1C10, 1C12, 1D10, 1E11, 1E11 N103D, 1G12, 1E11.C1, 1E11.C2, 1E11.C3, 1E11.C4, 1E11.C5, 1E11.C6, 1E11.E1, 1E11.E2, 1E11.E3, 1E11.E4, 1E11.E5, 1E11.C2E1, 1E11.C2E3, 1E11.C2E4 and 1E11.C2E5.

The anti-TLR4 antibodies of the invention include an altered antibody in which at least the amino acid residue at EU position 325 and at least the amino acid residue at EU position 328 in the CH2 domain of the Fc portion of the antibody has been modified. For example, at least the amino acid residue at EU position 325 has been substituted with serine, and at least the amino acid residue at EU position 328 has been substituted with phenylalanine.

These anti-TLR4 antibodies with a modified Fc portion elicit modified effector functions e.g., a modified Fc receptor activity, as compared to an unaltered antibody. For example, the human Fc receptor is CD32A. In some embodiments, these anti-TLR4 antibodies elicit a prevention of proinflammatory mediators release following ligation to CD32A as compared to an unaltered antibody. Thus, these anti-TLR4 antibodies elicit a modified Fc receptor activity, such as the prevention of proinflammatory mediators release while retaining the ability to bind a target antigen. In some embodiments, these anti-TLR4 antibodies are neutralizing antibodies, wherein the anti-TLR4 antibody elicits a modified Fc receptor activity, while retaining the ability to neutralize one or more biological activities of a target antigen.

For example, anti-TLR4 antibodies of the invention include monoclonal antibodies that bind the human TLR4/MD-2 receptor complex. This receptor complex is activated by lipopolysaccharide (LPS), the major component of the outer membrane of gram-negative bacteria. The anti-TLR4 antibodies of the invention inhibit receptor activation and subsequent intracellular signaling via LPS. Thus, the anti-TLR4 antibodies neutralize the activation of the TLR4/MD-2 receptor complex. In particular, the invention provides anti-TLR4 antibodies that recognize the TLR4/MD-2 receptor complex expressed on the cell surface. These anti-TLR4 antibodies block LPS-induced and other TLR4 ligand-induced pro-inflammatory cytokine (e.g., IL-6, IL-8, TNFα) production. In addition, some anti-TLR4 antibodies of the invention also recognize TLR4 when not complexed with MD-2. The altered antibody is, e.g., a humanized antibody.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of; cell and tissue culture, molecular biology, and protein and oligo-or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of; analytical chemistry, synthetic 'organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

Use of Anti-TLR4 Antibodies

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed., Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery—some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include an anti-TLR4 antibody of the invention, are used to treat or alleviate a symptom associated with an immune-related disorder. The present invention also provides methods of treating or alleviating a symptom associated with an immune-related disorder. A therapeutic regimen is carried out by identifying a subject, e.g., a human patient suffering from (or at risk of developing) an immune-related disorder, using standard methods. For example, anti-TLR4 antibodies of the invention are useful therapeutic tools in the treatment of autoimmune diseases and/or inflammatory disorders. In certain embodiments, the use of anti-TLR4 antibodies that modulate, e.g., inhibit, neutralize, or interfere with, TLR signaling is contemplated for treating autoimmune diseases and/or inflammatory disorders.

Autoimmune diseases include, for example, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/ giant cell arteritis, ulcerative colitis, uveitis, vitiligo and Wegener's granulomatosis.

Inflammatory disorders include, for example, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

For example, anti-TLR4 antibodies are useful in the treatment of acute inflammation and sepsis induced by microbial products (e.g., LPS) and exacerbations arising from this acute inflammation, such as, for example, chronic obstructive pulmonary disease and asthma (see O'Neill, Curr. Opin. Pharmacol. 3: 396-403 (2003), hereby incorporated by reference in its entirety). Such antibodies are also useful in treating neurodegenerative autoimmune diseases. (Lehnardt et al., Proc. Natl. Acad. Sci. USA 100: 8514-8519 (2003), hereby incorporated by reference in its entirety).

In addition, the antibodies of the invention are also useful as therapeutic reagents in the treatment of diseases, such as, for example, osteoarthritis, which are caused by stress, for example, cellular stress, which, in turn, induces endogenous soluble "stress" factors that trigger TLR4. Endogenous soluble stress factor include e.g., Hsp60 (see Ohashi et al., J. Immunol. 164: 558 561 (2000)) and fibronectin (see Okamura etal., J. Biol. Chem. 276:10229 10233 (2001) and heparin sulphate, hyaluronan, gp96, [3 Defensin-2 or surfactant protein A (see e.g., Johnson et al., Crit. Rev. Immunol., 23(1-2):15-44 (2003), each of which is hereby incorporated by reference in its entirety). The antibodies of the invention are also useful in the treatment of a variety of disorders associated with stress, such as for example, cellular stress that is associated with subjects and patients placed on respirators, ventilators and other respiratory assist devices. For example, the antibodies of the invention are useful in the treatment of ventilator-induced lung injury ("VILI"), also referred to as ventilation-associated lung injury ("VALI").

Other disease areas in which inhibiting TLR4 function could be beneficial include, for example, chronic inflammation (e.g., chronic inflammation associated with allergic conditions and asthma), autoimmune diseases (e.g., inflammatory bowel disorder) and atherosclerosis (see O'Neill, Curr. Opin. Pharmacol. 3: 396-403 (2003), hereby incorporated by reference in its entirety).

Symptoms associated with these immune-related disorders include, for example, inflammation, fever, general malaise, fever, pain, often localized to the inflamed area, rapid pulse rate, joint pain or aches (arthralgia), rapid breathing or other abnormal breathing patterns, chills, confusion, disorientation, agitation, dizziness, cough, dyspnea, pulmonary infections, cardiac failure, respiratory failure, edema, weight gain, mucopurulent relapses, cachexia, wheezing, headache, and abdominal symptoms such as, for example, abdominal pain, diarrhea or constipation.

Efficaciousness of treatment is determined in association with any known method for diagnosing or treating the particular immune-related disorder. Alleviation of one or more symptoms of the immune-related disorder indicates that the antibody confers a clinical benefit.

Antibodies of the invention, including polyclonal, monoclonal, humanized and fully human antibodies, may be used as therapeutic agents. Such agents will generally be employed to treat or prevent a disease or pathology associated with aberrant expression or activation of a given target in a subject. An antibody preparation, preferably one having high specificity and high affinity for its target antigen, is administered to the subject and will generally have an effect due to its binding with the target. Administration of the antibody may abrogate or inhibit or interfere with the signaling function of the target. Administration of the antibody may abrogate or inhibit or interfere with the binding of the target with an endogenous ligand to which it naturally binds. For example, the antibody binds to the target and neutralizes TLR4 ligand-induced proinflammatory cytokine production.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Antibodies or a fragment thereof of the invention can be administered for the treatment of a variety of diseases and disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

The pharmaceutical compositions can be included in a container, pack, or dispenser together with instructions for administration.

The formulation can also contain more than one active compound, e.g., anti-TLR4 antagonist as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

In one embodiment, the active compound, e.g., an anti-TLR4 antagonist, is administered in combination therapy, i.e., combined with one or more additional agents that are useful for treating pathological conditions or disorders, such as various forms of cancer, autoimmune disorders and inflammatory diseases. The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

For example, the combination therapy can include one or more neutralizing anti-TLR4 antibodies of the invention coformulated with, and/or coadministered with, one or more additional therapeutic agents, e.g., one or more cytokine and growth factor inhibitors, immunosuppressants, anti-inflammatory agents, metabolic inhibitors, enzyme inhibitors, and/or cytotoxic or cytostatic agents, as described in more detail below. Such combination therapies may advantageously utilize lower dosages of the administered therapeutic agents, thus avoiding possible toxicities or complications associated with the various monotherapies.

Preferred therapeutic agents used in combination with a neutralizing anti-TLR4 antibody of the invention are those agents that interfere at different stages in an inflammatory response. In one embodiment, one or more neutralizing anti-TLR4 antibodies described herein may be coformulated with, and/or coadministered with, one or more additional agents such as other cytokine or growth factor antagonists (e.g., soluble receptors, peptide inhibitors, small molecules, ligand fusions); or antibodies or antigen binding fragments thereof that bind to other targets (e.g., antibodies that bind to other cytokines or growth factors, their receptors, or other cell surface molecules); and anti-inflammatory cytokines or agonists thereof.

Where antibody fragments are used, the smallest inhibitory fragment that specifically binds to the binding domain of the target protein and/or the smallest inhibitory fragment that interferes with or otherwise antagonizes TLR4 signaling is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

Levels of TLR4 ligands and other biomarkers are detecting using any of a variety of standard detection techniques. Detection agents can be used for detecting the presence of a given target (or a protein fragment thereof) in a sample. In some embodiments, the detection agent contains a detectable label. In some embodiments, the detection agent is an antibody (or fragment thereof) or a probe. In some embodiments, the agent or probe is labeled. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin.

The term "biological sample" is intended to include tissues, cells and biological fluids isolated from a subject, as well as tissues, cells and fluids present within a subject.

Included within the usage of the term "biological sample", therefore, is blood and a fraction or component of blood including blood serum, blood plasma, or lymph. The bodily fluids can be fluids isolated from anywhere in the body of the subject, preferably a peripheral location, including but not limited to, for example, blood, plasma, serum, synovial fluid, urine, sputum, spinal fluid, cerebrospinal fluid, pleural fluid, fluid of the respiratory, intestinal, and genitourinary tracts, saliva, intra-organ system fluid, ascitic fluid, tumor cyst fluid, amniotic fluid and combinations thereof. The biological sample also includes experimentally separated fractions of all of the preceding fluids. Biological samples also include solutions or mixtures containing homogenized solid material, such as feces, tissues, and biopsy samples. The detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Pharmaceutical Compositions

The antibodies or soluble chimeric polypeptides of the invention (also referred to herein as "active compounds"), and derivatives, fragments, analogs and homologs thereof, can be incorporated into pharmaceutical compositions suitable for administration. Such compositions typically comprise the antibody or soluble chimeric polypeptide and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin.

Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention will be further described in the following examples, which do not limit the scope of the invention described in the claims.

EXAMPLES

Example 1. Materials and Methods

Blockade of TLR4 Activation Stimulated by Immune Complex Containing Citrullinated Fibrinogen (cFb-IC):

Two methods were used to prepare the immune complex. In the first method, rabbit polyclonal antibody was used to prepare the immune complex. Briefly, in vitro citrullinated antigen (Fibrinogen) was plated and incubated overnight, then washed and blocked before being incubated with 50 ug/ml polyclonal rabbit anti-fibrinogen antibody (Dako) for 2 hours at 37° C., followed by washing. Then, 50,000 human monocyte derived macrophages that had been pretreated with either an anti-TLR4 antagonist, e.g., the NI-0101 antibody, or an anti-FcγRII antibody, or a relevant isotype control antibody, were added to the plates. Finally, after incubation for 16 hours, the supernatants were harvested, and a pro-inflammatory cytokine, e.g., TNFα was measured by ELISA.

In the second method, IgG isolated from a rheumatoid arthritis (RA) patient was used to prepare the immune complex. Briefly, in vitro citrullinated antigen (Fibrinogen) was plated and incubated overnight, then washed and blocked before being incubated with human RA-IgG (1 mg/ml) for 2 hours at 37° C., followed by washing. Then, 50,000 human monocyte derived macrophages that had been pretreated with either an anti-TLR4 antagonist, e.g., the NI-0101 antibody, an anti-FcγRII antibody, or a relevant isotype control antibody, were added to the plates. Finally, after incubation for 16 hours, the supernatants were harvested, and a pro-inflammatory cytokine, e.g., TNFα was measured by ELISA.

Measuring Levels of Immune Complex Containing Citrullinated Fibrinogen (IC-cFb):

Standard ELISA techniques were used to determine the levels of immune complex containing citrullinated fibrinogen (IC-cFb) in synovial fluid samples from patients with rheumatoid arthritis (RA). Briefly, the mouse anti-human citrullinated fibrinogen (cFb) antibody, 3D1, (anti-cFb, clone 3D1, #AM32004PU-N from Acris) was plated, incubated overnight, washed and blocked prior to incubation with a synovial fluid sample from RA patients in triplicate wells. An anti-human-IgG-Fc-HRP (SIGMA, #A0170) was used to detect the immune complex.

Stimulation of Synovial Fibroblasts from RA Patients with Synovial Fluid from RA Patients:

RA fibroblasts were plated, incubated for two days before supernatants were removed and fresh media was added. NI-0101 or isotype control (60 µg/mL in Medium, 40 µL/well) was added for the treatment wells, and an equal volume of medium was added to the untreated control wells. After incubation for 30 minutes, synovial fluid from RA patients was added to each well to a concentration of 2.5% in the final assay mix (40 µL/well of 7.5% synovial fluid). As positive control, LPS was added to 10 ng/mL (40 µL/well of 30 ng/mL LPS). After incubation for 24 hours, the supernatants were collected and a pro-inflammatory cytokine, e.g., interleukin-6 (IL-6) was detected by ELISA.

Stimulation of monocytes from peripheral blood of RA patients with synovial fluid from RA patients: CD14$^+$ monocytes were purified from peripheral blood of RA patients using MACS beads and adjusted to $1.25 \times 10^6$ cells/mL with fresh medium. The monocytes were then plated, and to the treatment wells, NI-0101 or isotype control (60 µg/mL in Medium, 40 was added for the treatment wells, and an equal volume of medium was added to the untreated control wells. After incubation for 30 minutes, diluted synovial fluid from RA patients was added to a concentration of 20%, 10%, 5% or 2.5% in the final assay mix. As positive control, LPS was added to 10 ng/mL in triplicate wells (40 µL/well of 30 ng/mL LPS). After incubation for 24 hours, the supernatants were collected and a pro-inflammatory cytokine, e.g., interleukin-6 (IL-6), TNFα, GM-CSF and/or IL-8, was detected by Luminex assay.

Example 2. Elevated Levels of TLR4 Ligands in Patient Samples Stimulate Cells to Produce Pro-Inflammatory Cytokines The levels of anti-citrullinated protein antibodies (ACPA) and different TLR4 ligands (cFb-IC, HMGB1, S100A8/A9 and Tenascin C) contained in synovial fluid of healthy subjects (N Syn.Fluid) or patients with rheumatoid arthritis (RA Syn.Fluid) were detected (FIGS. 2A-2E). Elevated levels of ACPA and the TLR4 ligands were detected in the samples from patients with RA.

Figure 3A:
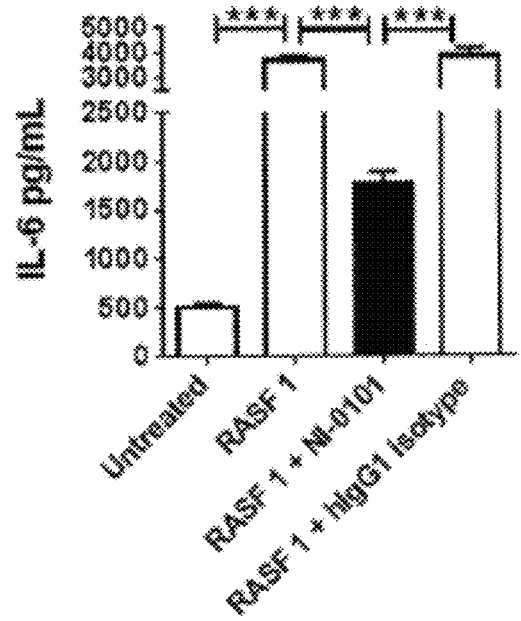
FIGS. 3A and 3B are a series of graphs that depict examples of the activation profiles of different rheumatoid arthritis synovial fluids (RASF) on synovial fibroblasts isolated from patients with RA and the dependence of the stimulation on TLR4.
Figure 3B:
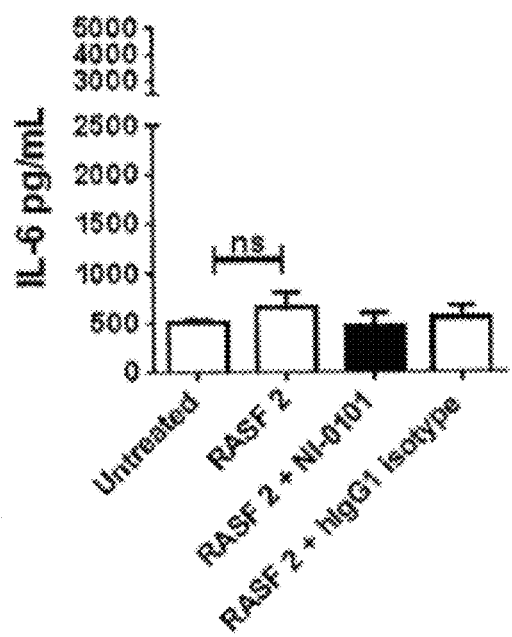
Figure 4A:
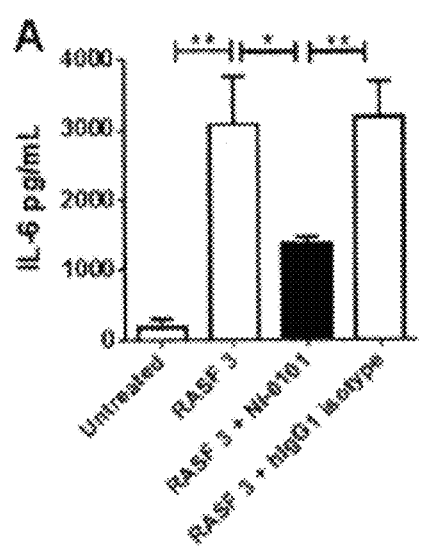
FIGS. 4A-4F are a series of graphs that depict examples of the activation profiles of different rheumatoid arthritis synovial fluids (RASF) on human monocytes isolated from patients with RA and the dependence of the stimulation on TLR4.
Figure 4B:
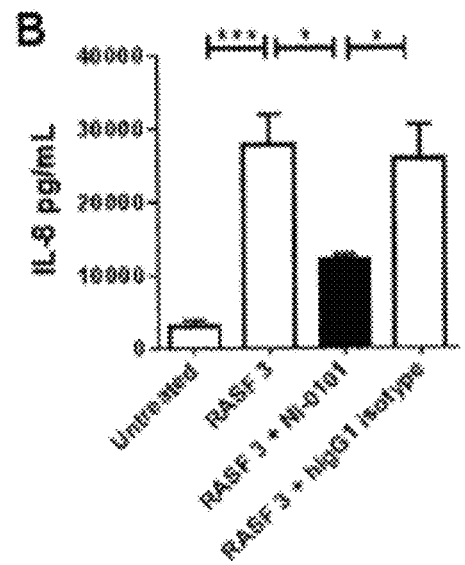
Figure 4C:
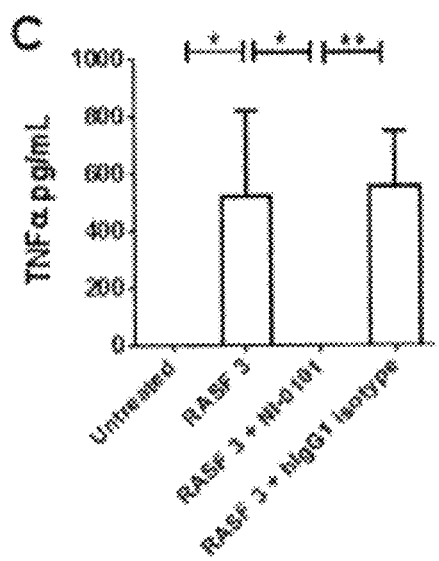
Figure 4D:
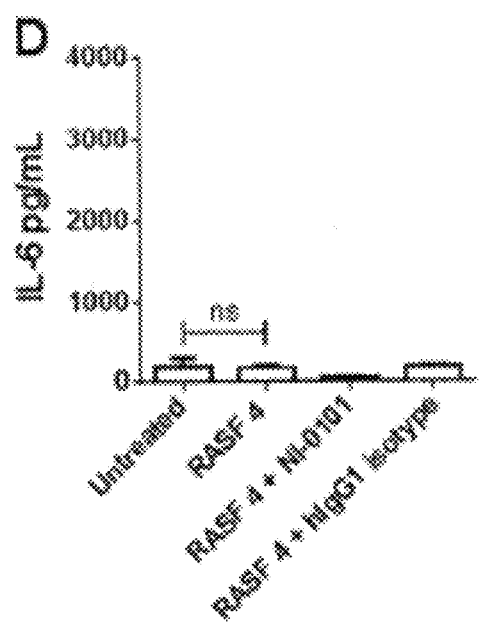
Figure 4E:
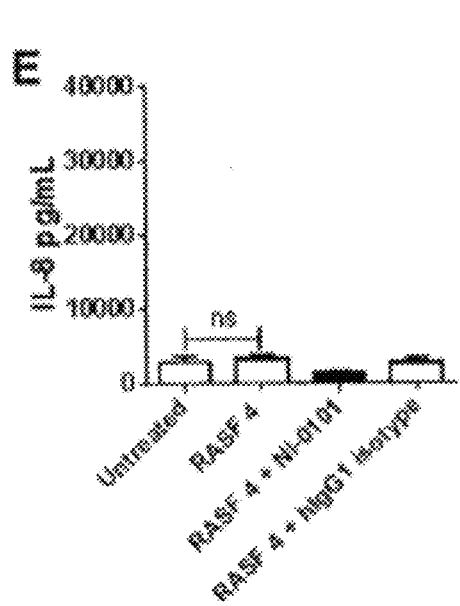
Figure 4F:
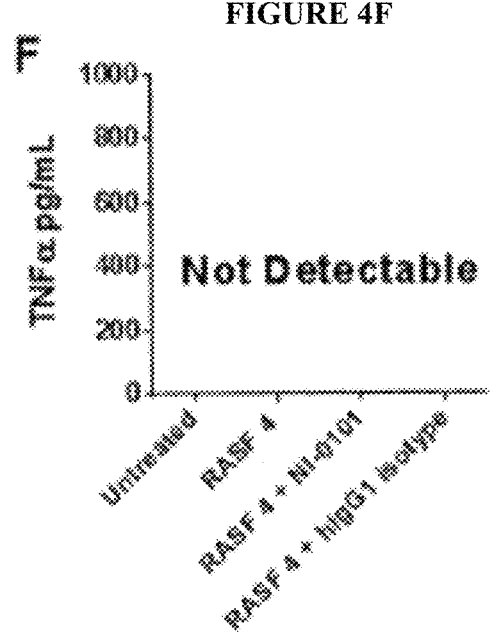

Example 3. Use of an Anti-TLR4 Antagonist Inhibits Production of Pro-Inflammatory Cytokines The activation profiles of different rheumatoid arthritis synovial fluids (RASF) on synovial fibroblasts isolated from patients with RA and the dependence of the stimulation on TLR4 in these samples were measured and analyzed. As shown in FIG. 3A, RASF from patient #1 (RASF 1) was found to stimulate RA synovial fibroblasts to produce the pro-inflammatory cytokine, IL-6. This stimulation was significantly blocked by the presence of an anti-human TLR4 mAb (e.g., NI-0101). In contrast, FIG. 3B demonstrates that a RASF sample from patient #2 (RASF 2) was unable to stimulate IL-6 production from RA synovial fibroblasts, and the anti-TLR4 mAb had no effect in this circumstance. Thus, the ability of a patient sample to stimulate the production of a pro-inflammatory cytokine can be used as indicator that that particular patient is likely to be suitable for treatment with an anti-TLR4 antagonist, such as a neutralizing anti-TLR4 antibody, e.g., NI-0101.

Similar studies were run to detect and analyze the activation profiles of different rheumatoid arthritis synovial fluids (RASF) on human monocytes isolated from patients with RA and the dependence of the stimulation on TLR4 (FIG. 4). FIGS. 4A, 4B and 4C depict the ability of a RASF sample from patient #3 (RASF 3) to stimulate production of the pro-inflammatory cytokines, IL-6, IL8 and TNFα, respectively, from human monocytes isolated from RA patients. This stimulation was significantly blocked by the presence of an anti-human TLR4 mAb (e.g., NI-0101). In contrast, FIGS. 4D, 4E and 4F depict a RASF sample from patient #4 (RASF 4) that was unable to stimulate the production of IL-6, IL8 and TNFα from human monocytes isolated from RA patients, and the anti-TLR4 mAb had no effect in this circumstance. Again, these studies demonstrate the ability of a patient sample to stimulate the production of a pro-inflammatory cytokine can be used as indicator that that particular patient is likely to be suitable for treatment with an anti-TLR4 antagonist, such as a neutralizing anti-TLR4 antibody, e.g., NI-0101.

Figure 5A:
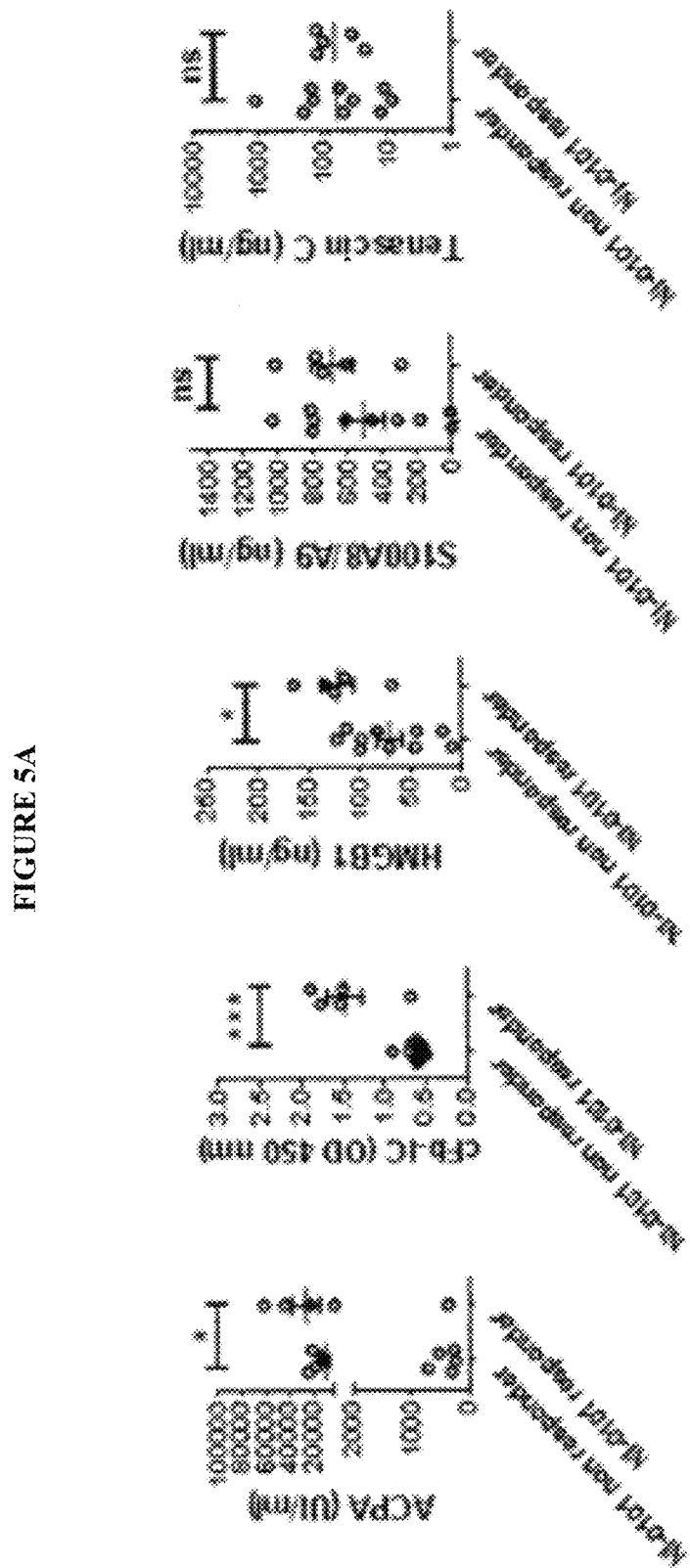
FIGS. 5A and 5B are a series of graphs that depict the correlation between the expression levels of anti-citrullinated protein antibodies (ACPA) or TLR4 ligands in rheumatoid arthritis synovial fluids (RASF) and the capacity of cell stimulation to be inhibited by an anti-human TLR4 mAb. The TLR4 ligands include immune complex containing citrullinated fibrinogen (cFb-IC), high-mobility group protein B1 (HMGB1), S100A8/A9 and Tenascin C. The cell types include RA patient synovial fibroblasts (FIG. 5A) and RA patient monocytes (FIG. 5B). Student's t tests were performed. *p<0.05, p<0.01, *p<0.001, ns: not significant.
Figure 5B:
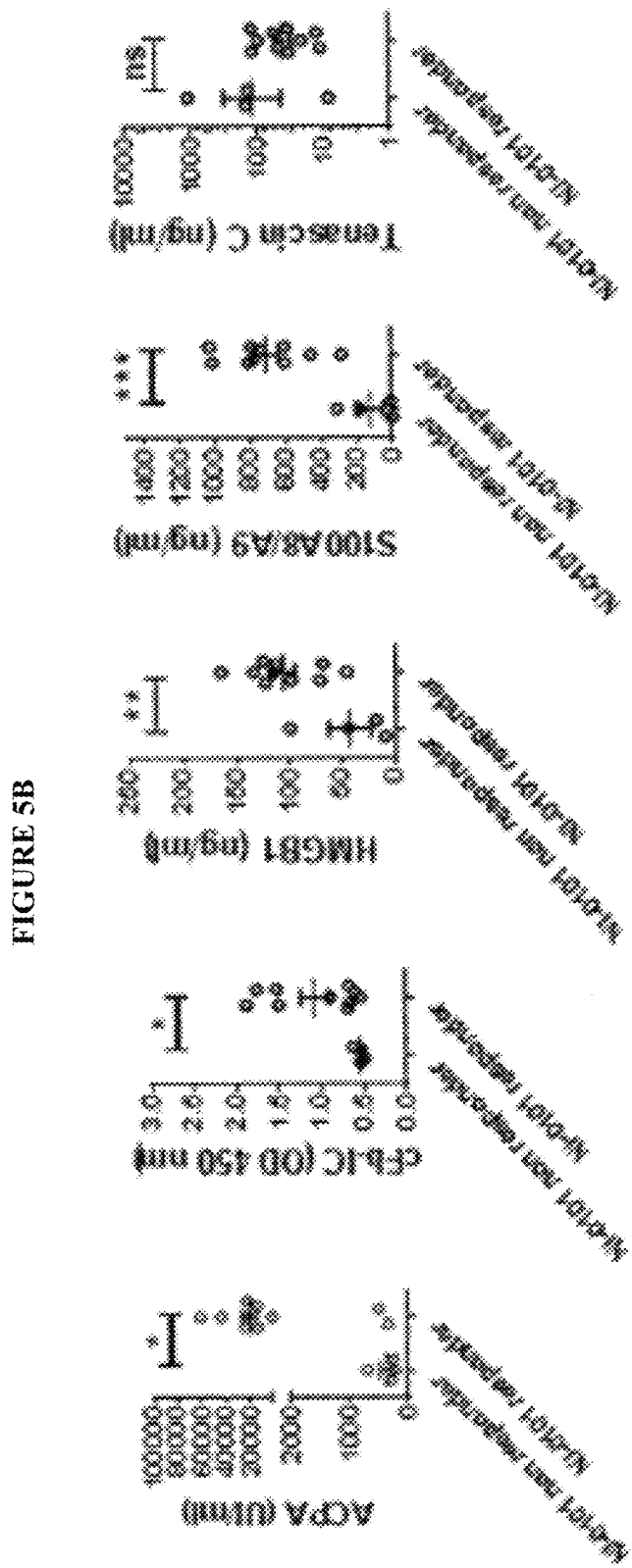

Example 4. Correlation Between Expression Levels of TLR4 Ligands and Other Markers and the Capacity of Cell Stimulation to be Inhibited by an Anti-TLR4 Antagonist FIGS. 5A and 5B are a series of graphs that depict the correlation between the expression levels of anti-citrullinated protein antibodies (ACPA) or TLR4 ligands in rheumatoid arthritis synovial fluids (RASF) and the capacity of cell stimulation to be inhibited by an anti-human TLR4 mAb. The TLR4 ligands include immune complex containing citrullinated fibrinogen (cFb-IC), high-mobility group protein B1 (HMGB1), S100A8/A9 and Tenascin C. The cell types include RA patient synovial fibroblasts (A) and RA patient monocytes (B).

Table 1 summarizes and correlates the levels of anti-citrullinated protein antibodies (ACPA), immune complex containing citrullinated fibrinogen (cFb-IC), high-mobility group protein B1 (HMGB1), S100A8/A9 and Tenascin C in rheumatoid arthritis synovial fluids (RASF) of 14 patients and the capacity of the RASF to induce cytokine production with an ability to be blocked by an anti-human TLR4 mAb, e.g., NI-0101) treatment with either RA blood monocytes and RA synovial fibroblasts.

antibody NI-0101 were analyzed. For monocytes, several markers including ACPA, cFb-IC, HMGB1 and S100A8/A9, were found to be good predictors of monocyte response score, with S100A8/A9 being the best individual classifier. If the level of S100A8/A9 detected in synovial fluid was set to 387 ng/ml, this marker predicted 100% of non-responders to NI-0101 treatment with 80% accuracy and 100% of responders with 89% accuracy. In the samples tested, 36% (4 out of 5) of the subjects identified did not have a level of S100A8/A9 detected in monocytes greater than or equal to 387, and 64% (8/9) of the subjects did have a level of S100A8/A9 detected in synovial fluid greater than or equal to 387.

For fibroblasts, cFb-IC was fond to be the best individual predictor of fibroblast response. If the level of cFb-IC detected in synovial fluid (OD 450 nm reading) was set to 1.2, this marker predicts 100% of non-responders to NI-0101 treatment with 90% accuracy and 80% of responders with 100% accuracy. In the samples tested, 73% (10 out of 11) of the subjects identified did not have a level of cFb-IC detected in fibroblasts greater than or equal to 1.2, and 27% (4/4) of the subjects did have a level of cFb-IC detected in synovial fluid greater than or equal to 1.2.

Figure 7:
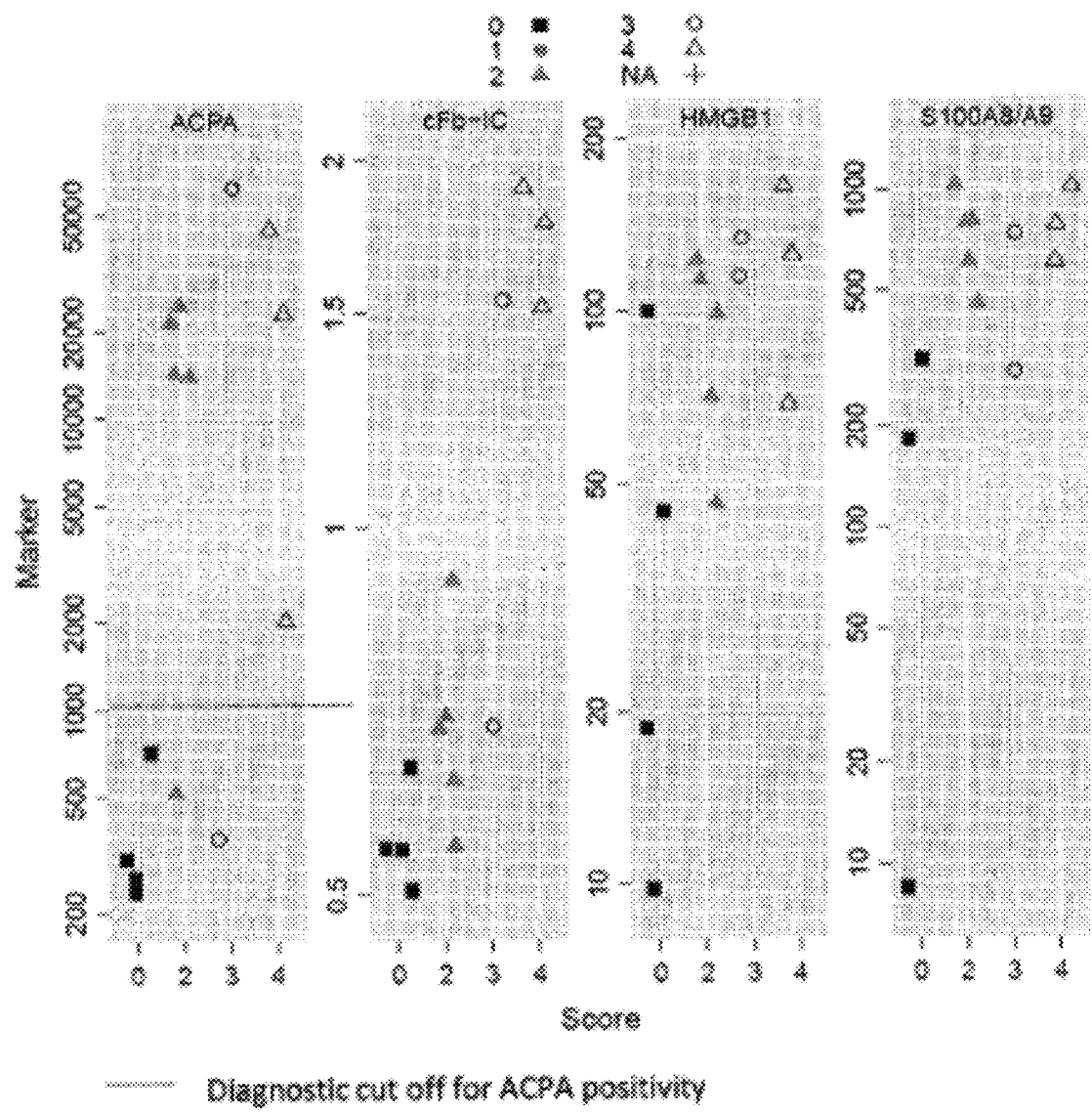
FIG. 7 is a graph illustrating the marker level by combined monocytes and fibroblasts response score (cMFRS) to treatment with the anti-human TLR mAb, NI-0101. Biological response scores: 0, 1, 2, 3, or 4 cell donor(s) responded to rheumatoid arthritis synovial fluids (RASF) stimulation and was/were inhibited by treatment with NI-0101.

The marker levels by combined monocytes and fibroblasts response score (cMFRS) in response to treatment with NI-0101 was evaluated as shown in FIG. 7.

Figure 8:
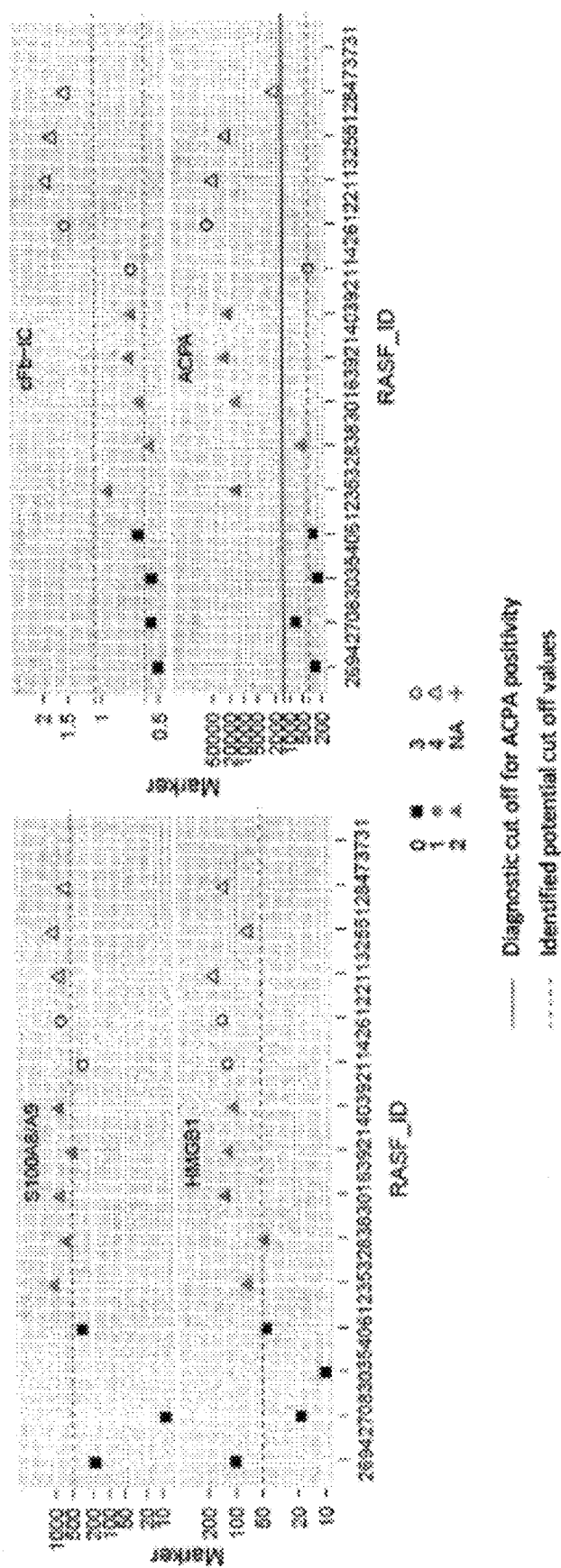
FIG. 8 is a graph illustrating that ACPA/cFb-IC and S100A8/A9/HMGB1 form independent tandems that show a trend of correlation in RASF samples tested.

Further evaluation identified that the markers ACPA and cFb-IC show a trend of correlation in the RASF samples, and similarly, the markers S100A8/A9 and HMGB1 demonstrate a trend of correlation in the RASF samples (FIG. 8). These two tandems were found to be independent of each other.

It was also found that the markers ACPA, cFb-IC, HMGB1 and S100A8/A9 are each individually good predictors for combined monocytes and fibroblasts response score (cMFRS) to treatment with the anti-human TLR mAb, NI-0101. Each of ACPA, cFb-IC and HMGB1 were found to exhibit identical predictive power, where each marker was found to predict 75% of non-responders to NI-0101 treatment with 100% accuracy and 100% of responders with 91% accuracy. In particular, in the samples tested, 21% (3 out of 3) of the subjects identified did not have a level of

TABLE 1

| | RA synovium fibroblast | | RA blood-derived monocytes | | TLR4 endogenous ligands and ACPA levels in RA synovial fluids | | | | |
|---|---|---|---|---|---|---|---|---|---|
| RASF Sample ID# | IL6 Induction | Blockade observed with anti-TLR4 | IL6 Induction | Blockade observed with anti-TLR4 | ACPA (UI/ml) | cFb-IC OD 450 nm | HMGB1 (ng/ml) | S100 (ng/ml) | Tenascin C (ng/mL) |
| 1 | ✓ | ✓ | ✓ | ✓ | <u>44374.3</u> | <u>1.90</u> | <u>165.15</u> | 784 | 35.7 |
| 2 | ✓ | ✓ | ✓ | ✓ | 356.6 | 0.69 | <u>115.17</u> | 288.1 | 22.1 |
| 3 | ✓ | | ✓ | ✓ | <u>13891.9</u> | 0.91 | 71.07 | <u>1034.1</u> | 11.5 |
| 4 | ✓ | ✓ | ✓ | ✓ | <u>22692.6</u> | <u>1.78</u> | 68.58 | <u>1018.5</u> | <u>126.2</u> |
| 5 | ✓ | ✓ | ✓ | ✓ | <u>61638.9</u> | <u>1.54</u> | <u>134.24</u> | <u>743.1</u> | 99.2 |
| 6 | ✓ | | | | 264 | 0.5 | 99.81 | 182.9 | 8.7 |
| 7 | | | | | 710.4 | 0.55 | 18.73 | 8.5 | <u>153.2</u> |
| 8 | ✓ | | ✓ | ✓ | 515.8 | 0.55 | 46.23 | <u>612.6</u> | 12.9 |
| 9 | ✓ | ✓ | ✓ | ✓ | <u>2002.7</u> | <u>1.51</u> | <u>125.08</u> | <u>609.2</u> | <u>124.9</u> |
| 10 | | | ✓ | ✓ | <u>14269.5</u> | 0.62 | <u>122.85</u> | <u>798.1</u> | 34.5 |
| 11 | ✓ | | | | 236 | 0.54 | 9.79 | 0 | <u>142.6</u> |
| 12 | ✓ | | ✓ | ✓ | <u>24406.5</u> | 0.7 | <u>113.51</u> | 459.3 | 49.3 |
| 13 | ✓ | | ✓ | ✓ | <u>21300.7</u> | 0.68 | 98.64 | <u>813.3</u> | 56.6 |
| 14 | | | | | 303.2 | 0.64 | 44.76 | 313.8 | <u>1134.3</u> |

The underlining used in Table 1 represents RASF samples positive for ACPA and TLR4 ligands using the following arbitrary thresholds: ACPA (>2000 UI/ml), cFb-Ic (>1.5 OD), HMGB1 (>100 ng/ml), S100 (>500 nmg/ml), and Tenascin C (>100 ng/ml)

Example 5. Statistical Analysis of TLR4 Ligands and Other Biomarkers

Recursive partitioning and regression trees (rpart) algorithms were used to find the optimal thresholds to classify the data according to their score. The performance of each tree was evaluated by the inspection of its confusion matrix. The trees with the lowest complexity were chosen when multiple solutions were available, i.e., those with minimal number of nodes and splits. The mean of the three replicates was used as a biomarker value.

The best individual classifiers for monocytes or fibroblasts response scores to treatment with the anti-TLR4

ACPA detected in synovial fluid greater than or equal to 330 Ul/ml, and 79% (10111) of the subjects did have a level of ACPA detected in synovial fluid greater than or equal to 330 Ul/ml. In the samples tested, 21% (3 out of3) of the subjects identified did not have a level of cFb-IC detected in synovial fluid greater than or equal to 0.55, and 79% (10111) of the subjects did have a level of cFb-IC detected in synovial fluid greater than or equal to 0.55 (OD 450 nm reading). In the samples tested, 21% (3 out of 3) of the subjects identified did not have a level of HMGB1 detected in synovial fluid greater than or equal to 45 ng/ml, and 79% (10/11) of the subjects did have a level of HMGB1 detected in synovial fluid greater than or equal to 45.

Figure 9:
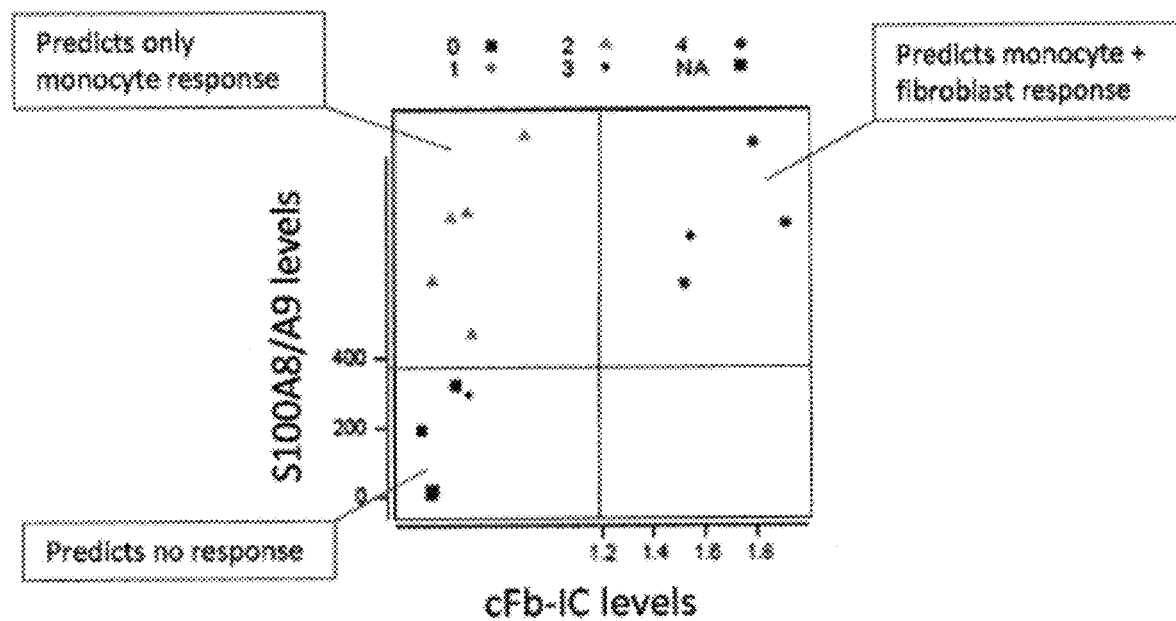
FIG. 9 is a graph that illustrates that the combination of S100A8/A9 and cFb-IC are predictors for the combined monocytes and fibroblasts response score (cMFRS) to treatment with the anti-human TLR mAb, NI-0101.

The combination of S100A8/A9 and cFb-IC provided the best classifier for the prediction of combined monocytes and fibroblasts response score (cMFRS) to treatment with the anti-human TLR mAb, NI-0101. If the level of S100A8/A9 detected in synovial fluid were found to be greater than or equal to 387 ng/ml and the level of cFb-IC detected in synovial fluid were found to be greater than or equal to 1.2 (OD 450 nm reading), this combination of markers was found to predict 100% of non-responders to NI-0101 treatment with 80% accuracy and 90% of responders with 100% accuracy (FIG. 9). While each individual marker, S100A8/A9 and cFb-IC, is a good predictor of cMFRS, the combination of the two is the best predictor.

Other combinations of markers are suitable predictors of monocyte and fibroblast response. For example, the predictor of monocyte and fibroblast response is a combination selected from the group consisting of (i) S100A8/A9 and HMGB1; (ii) S100A8/A9 and cFb-IC; (iii) S100A8/A9 and ACPA; (iv) ACPA and cFb-IC; (v) ACPA and HMGB1; (vi) HMGB1 and cFb-IC; (vii) S100A8/A9, ACPA and HMGB1; (viii) S100A8/A9, ACPA and cFb-IC; (ix) S100A8/A9, cFb-IC and HMGB1; (x) ACPA, HMGB1 and cFb-IC; and (xi) S100A8/A9, cFb-IC, ACPA and HMGB1.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of alleviating a symptom in a subject having a disorder associated with excessive aberrant TLR4 signaling or elevated TLR4 ligand expression or activity, the method comprising:
   a) identifying a subject having an elevated level of expression of citrullinated fibrinogen and citrullinated histone 2b compared to a control level of expression; and
   b) administering an anti-TLR4 antibody or an immunologically active fragment thereof that binds and neutralizes TLR4, in an amount sufficient to alleviate the symptom of the disorder.

2. The method of claim 1, further comprising detecting the level of an anti-citrullinated protein antibody (ACPA), a citrullinated fibrin, a citrullinated vimentin, a citrullinated enolase, a citrullinated chemokine, HMGB1, S100A8/A9, Tenascin C, or combinations thereof.

3. The method of claim 2, wherein the citrullinated chemokine is citrullinated CXCL10.

4. The method of claim 1, wherein the citrullinated fibrinogen and/or the citrullinated histone 2b is in an immune complex.

5. The method of claim 4, wherein the citrullinated fibrinogen and/or the citrullinated histone 2b is in an immune complex with an IgG protein.

6. The method of claim 1, wherein the biological sample is or is derived from blood.

7. The method of claim 1, wherein the biological sample is or is derived from urine.

8. The method of claim 1, wherein the biological sample is or is derived from synovial fluid.

9. The method of claim 1, wherein the anti-TLR4 antibody or immunologically active fragment thereof comprises a variable heavy chain complementarity determining region 1 (VH CDR1) the amino acid sequence of GGYSWH (SEQ ID NO: 1); a VH CDR2 region comprising the amino acid sequence of YIHYSGYTDFNPSLKT (SEQ ID NO: 2); a VH CDR3 region comprising the amino acid sequence of KDPSDAFPY (SEQ ID NO: 3); a variable light chain complementarity determining region 1 (VL CDR1) region comprising the amino acid sequence of RASQSISDHLH (SEQ ID NO: 4); a VL CDR2 region comprising the amino acid sequence of YASHAIS (SEQ ID NO: 5); and a VL CDR3 region comprising the amino acid sequence of QQGHSFPLT (SEQ ID NO: 6).

10. The method of claim 9, wherein the anti-TLR4 antibody or immunologically active fragment thereof comprises the heavy chain variable amino acid sequence QVQLQESGPGLVKPSDTLSLTCAVSGYSITGGYSWH-WIRQPPGKGLEWMGYIHYSGYT DFNPSLK-TRITISRDTSKNQFSLKLSSVTAVDTAVYYCARKDPS-DAFPYWGQGTLVTVSS (SEQ ID NO: 7) and the light chain variable amino acid sequence EIVLTQSPDFQSVTP-KEKVTITCRASQSISDHLHWYQQKPDQSPKL-LIKYASHAISGVPSR FSGSGSGTDFTLTINSLEAE-DAATYYCQQGHSFPLTFGGGTKVEIK (SEQ ID NO: 8).

11. The method of claim 10, wherein the anti-TLR4 antibody or immunologically active fragment thereof comprises the heavy chain amino acid sequence MGWSWIFLFLLSGTAGVHCQVQLQESGPGLVKPSDTLSLTCAVSGYSITGGYSWHWIRQPPGKGLEWMGYIHYSGYTDFNPSLKTRITISRDTSKNQFSLKLSSVTAVDTAVYYCAR KDPSDAFPYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVE PKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSSKAFPAPIE KTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 9) and the light chain amino acid sequence MEWSWVFLFFLSVTTGVHSEIVLTQSPDFQSVTPKEKVTITCRASQSISDHLHWYQQKPD QSPKLLIKYASHAISGVPSRFSGSGSGTDFTLTINSLEAEDAATYYCQQGHSFPLTFGGGTKVEIKRTVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC (SEQ ID NO: 10).

12. The method of claim 1, wherein the subject is human.

13. The method of claim 1, wherein the disorder is an autoimmune or inflammatory disorder.

14. The method of claim 1, wherein the disorder is rheumatoid arthritis (RA).

15. The method of claim 1, wherein the disorder is atherosclerosis.

16. The method of claim 1, wherein the disorder is associated with organ or tissue transplantation.

17. The method of claim 1, wherein the disorder is associated with acute lung injury.

18. The method of claim 1, wherein the disorder is associated with ischemia/reperfusion injury.

* * * * *

SEQUENCE LISTING

```
<160> NUMBER OF SEQ ID NOS: 139

<210> SEQ ID NO 1
<211> LENGTH: 6
<212> TYPE: PRT
<213> ORGANISM: Artificial Sequence
<220> FEATURE:
<223> OTHER INFORMATION: Anti-TLR4 VH CDR1 region

<400> SEQUENCE: 1

Gly Gly Tyr Ser Trp His
1               5

<210> SEQ ID NO 2
<211> LENGTH: 16
<212> TYPE: PRT
<213> ORGANISM: Artificial Sequence
<220> FEATURE:
<223> OTHER INFORMATION: Anti-TLR4 VH CDR2 region

<400> SEQUENCE: 2

Tyr Ile His Tyr Ser Gly Tyr Thr Asp Phe Asn Pro Ser Leu Lys Thr
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: Anti-TLR4 VH CDR3 region

<400> SEQUENCE: 3

Lys Asp Pro Ser Asp Ala Phe Pro Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: Anti-TLR4 VL CDR1 region

<400> SEQUENCE: 4
```

Arg Ala Ser Gln Ser Ile Ser Asp His Leu His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Anti-TLR4 VL CDR2 region

<400> SEQUENCE: 5

Tyr Ala Ser His Ala Ile Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Anti-TLR4 VL CDR3 region

<400> SEQUENCE: 6

Gln Gln Gly His Ser Phe Pro Leu Thr
1               5

<210> SEQ ID NO 7
<211> LENGTH: 118
<212> TYPE: PRT
<213> ORGANISM: Artificial Sequence
<220> FEATURE:
<223> OTHER INFORMATION: Anti-TLR4 VH seqeunce

<400> SEQUENCE: 7

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
                20                  25                  30

Tyr Ser Trp His Trp Ile Arg Gln Pro Pro Gly Lys Gly Leu Glu Trp
            35                  40                  45

Met Gly Tyr Ile His Tyr Ser Gly Tyr Thr Asp Phe Asn Pro Ser Leu
        50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Pro Ser Asp Ala Phe Pro Tyr Trp Gly Gln Gly Thr
            100                 105                 110

Leu Val Thr Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: Anti-TLR4 VL sequence

<400> SEQUENCE: 8

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
                20                  25                  30

```
Leu His Trp Tyr Gln Gln Lys Pro Asp Gln Ser Pro Lys Leu Leu Ile
            35                  40                  45

Lys Tyr Ala Ser His Ala Ile Ser Gly Val Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys
                100                 105

<210> SEQ ID NO 9
<211> LENGTH: 467
<212> TYPE: PRT
<213> ORGANISM: Artificial Sequence
<220> FEATURE:
<223> OTHER INFORMATION: Anti-TLR4 heavy chain

<400> SEQUENCE: 9

Met Gly Trp Ser Trp Ile Phe Leu Phe Leu Leu Ser Gly Thr Ala Gly
1               5                   10                  15

Val His Cys Gln Val Gln Leu Gln Glu Ser Gly Pro Gly Leu Val Lys
            20                  25                  30

Pro Ser Asp Thr Leu Ser Leu Thr Cys Ala Val Ser Gly Tyr Ser Ile
        35                  40                  45

Thr Gly Gly Tyr Ser Trp His Trp Ile Arg Gln Pro Pro Gly Lys Gly
    50                  55                  60

Leu Glu Trp Met Gly Tyr Ile His Tyr Ser Gly Tyr Thr Asp Phe Asn
65                  70                  75                  80

Pro Ser Leu Lys Thr Arg Ile Thr Ile Ser Arg Asp Thr Ser Lys Asn
                85                  90                  95

Gln Phe Ser Leu Lys Leu Ser Ser Val Thr Ala Val Asp Thr Ala Val
            100                 105                 110

Tyr Tyr Cys Ala Arg Lys Asp Pro Ser Asp Ala Phe Pro Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285
```

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Ser Lys Ala Phe Pro Ala Pro Ile
        340                 345                 350

Glu Lys Thr Ile Ser Lys Ala Lys Gly Gln Pro Arg Glu Pro Gln Val
    355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
        420                 425                 430

Asp Lys Ser Arg Trp Gln Gln Gly Asn Val Phe Ser Cys Ser Val Met
    435                 440                 445

His Glu Ala Leu His Asn His Tyr Thr Gln Lys Ser Leu Ser Leu Ser
450                 455                 460

Pro Gly Lys
465

<210> SEQ ID NO 10
<211> LENGTH: 233
<212> TYPE: PRT
<213> ORGANISM: Artificial Sequence
<220> FEATURE:
<223> OTHER INFORMATION: Anti-TLR4 light chain

<400> SEQUENCE: 10

Met Glu Trp Ser Trp Val Phe Leu Phe Phe Leu Ser Val Thr Thr Gly
1               5                   10                  15

Val His Ser Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Ser Asp His Leu His Trp Tyr Gln Gln Lys Pro Asp Gln Ser Pro Lys
    50                  55                  60

Leu Leu Ile Lys Tyr Ala Ser His Ala Ile Ser Gly Val Pro Ser Arg
65                  70                  75                  80

Phe Ser Gly Ser Gly Ser Gly Thr Asp Phe Thr Leu Thr Ile Asn Ser
            85                  90                  95

Leu Glu Ala Glu Asp Ala Ala Thr Tyr Tyr Cys Gln Gln Gly His Ser
        100                 105                 110

Phe Pro Leu Thr Phe Gly Gly Gly Thr Lys Val Glu Ile Lys Arg Thr
    115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
            165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 11
<211> LENGTH: 1404
<212> TYPE: DNA
<213> ORGANISM: Artificial Sequence
<220> FEATURE:
<223> OTHER INFORMATION: Anti-TLR4 heavy chain

<400> SEQUENCE: 11

| | | | | | |
|---|---|---|---|---|---|
| atgggatgga | gctggatctt | tctcttcctc | ctgtcaggaa | ctgcaggtgt | acattgccag | 60 |
| gtgcagcttc | aggagtccgg | cccaggactg | gtgaagcctt | cggacaccct | gtccctcacc | 120 |
| tgcgctgtct | ctggttactc | catcaccggt | ggttatagct | ggcactggat | acggcagccc | 180 |
| ccagggaagg | gactggagtg | gatggggtat | atccactaca | gtggttacac | tgacttcaac | 240 |
| ccctccctca | agactcgaat | caccatatca | cgtgacacgt | ccaagaacca | gttctccctg | 300 |
| aagctgagct | ctgtgaccgc | tgtggacact | gcagtgtatt | actgtgcgag | aaaagatccg | 360 |
| tccgacgcct | tccttactg | gggccaaggg | actctggtca | ctgtctcttc | cgcctccacc | 420 |
| aagggcccat | cggtcttccc | cctggcaccc | tcctccaaga | gcacctctgg | gggcacagcg | 480 |
| gccctgggct | gcctggtcaa | ggactacttc | cccgaaccgg | tgacggtgtc | gtggaactca | 540 |
| ggcgccctga | ccagcggcgt | gcacaccttc | ccggctgtcc | tacagtcctc | aggactctac | 600 |
| tccctcagca | gcgtggtgac | cgtgccctcc | agcagcttgg | gcacccagac | ctacatctgc | 660 |
| aacgtgaatc | acaagcccag | caacaccaag | gtggacaaga | gagttgagcc | caaatcttgt | 720 |
| gacaaaactc | acacatgccc | accgtgccca | gcacctgaac | tcctgggggg | accgtcagtc | 780 |
| ttcctcttcc | ccccaaaacc | caaggacacc | ctcatgatct | cccggacccc | tgaggtcaca | 840 |
| tgcgtggtgg | tggacgtgag | ccacgaagac | cctgaggtca | agttcaactg | gtacgtggac | 900 |
| ggcgtggagg | tgcataatgc | caagacaaag | ccgcgggagg | agcagtacaa | cagcacgtac | 960 |
| cgtgtggtca | gcgtcctcac | cgtcctgcac | caggactggc | tgaatggcaa | ggagtacaaa | 1020 |
| tgcaaggtct | ccaacaaagc | cctcccagcc | cccatcgaga | aaaccatctc | caaagccaaa | 1080 |
| gggcagcccc | gagaaccaca | ggtgtacacc | ctgcccccat | cccgggagga | gatgaccaag | 1140 |
| aaccaggtca | gcctgacctg | cctggtcaaa | ggcttctatc | ccagcgacat | cgccgtggag | 1200 |
| tgggagagca | atgggcagcc | ggagaacaac | tacaagacca | cgcctcccgt | gctggactcc | 1260 |
| gacggctcct | tcttcctcta | tagcaagctc | accgtggaca | agagcaggtg | gcagcagggg | 1320 |
| aacgtcttct | catgctccgt | gatgcatgag | gctctgcaca | accactacac | gcagaagagc | 1380 |
| ctctccctgt | ctccgggtaa | atag | | | | 1404 |

<210> SEQ ID NO 12
<211> LENGTH: 702
<212> TYPE: DNA
<213> ORGANISM: Artificial Sequence
<220> FEATURE:
<223> OTHER INFORMATION: Anti-TLR4 light chain

<400> SEQUENCE: 12

```
atggaatgga gctgggtctt tctcttcttc ctgtcagtaa ctacaggtgt ccactccgaa      60
attgtgttga cgcagtctcc agactttcag tctgtgactc caaaggaaaa agtcaccatc     120
acctgcaggg ccagtcagag tatcagcgac cacttacact ggtaccaaca gaaacctgat     180
cagtctccca agctcctcat caaatatgct tcccatgcca tttctggggt cccatcgagg     240
ttcagtggca gtgggtctgg gacagacttc actctcacca tcaatagcct agaggctgaa     300
gatgctgcaa cgtattactg tcagcagggt cacagttttc cgctcacttt cggcggaggg     360
accaaggtgg agatcaaacg tacggtggct gcaccatctg tcttcatctt cccgccatct     420
gatgagcagt tgaaatctgg aactgcctct gttgtgtgcc tgctgaataa cttctatccc     480
agagaggcca agtacagtg gaaggtggat aacgccctcc aatcgggtaa ctcccaggag     540
agtgtcacag agcaggacag caaggacagc acctacagcc tcagcagcac cctgacgctg     600
agcaaagcag actacgagaa acacaaagtc tacgcctgcg aagtcaccca tcagggcctg     660
agctcgcccg tcacaaagag cttcaacagg ggagagtgtt ag                        702
```

<210> SEQ ID NO 13

<400> SEQUENCE: 13

000

<210> SEQ ID NO 14
<211> LENGTH: 9
<212> TYPE: PRT
<213> ORGANISM: Artificial Sequence
<220> FEATURE:
<223> OTHER INFORMATION: Anti-TLR4 VH CDR1 region
<220> FEATURE:
<221> NAME/KEY: misc_feature
<222> LOCATION: (2)..(2)
<223> OTHER INFORMATION: Xaa may be Phe or Tyr
<220> FEATURE:
<221> NAME/KEY: misc_feature
<222> LOCATION: (5)..(5)
<223> OTHER INFORMATION: Xaa may be Arg, Gly or Trp
<220> FEATURE:
<221> NAME/KEY: misc_feature
<222> LOCATION: (6)..(6)
<223> OTHER INFORMATION: Xaa may be Tyr, Phe or Gly

<400> SEQUENCE: 14

Gly Xaa Pro Ile Xaa Xaa Gly Tyr Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Anti-TLR4 VH CDR1 region

<400> SEQUENCE: 15

Gly Tyr Ser Ile Thr Gly Gly Tyr Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Anti-TLR4 VH CDR1 region

```
<400> SEQUENCE: 16

Gly Phe Pro Ile Arg Tyr Gly Tyr Ser
1               5

<210> SEQ ID NO 17
<211> LENGTH: 9
<212> TYPE: PRT
<213> ORGANISM: Artificial Sequence
<220> FEATURE:
<223> OTHER INFORMATION: Anti-TLR4 VH CDR1 region

<400> SEQUENCE: 17

Gly Tyr Pro Ile Arg Phe Gly Tyr Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Anti-TLR4 VH CDR1 region

<400> SEQUENCE: 18

Gly Tyr Pro Ile Arg His Gly Tyr Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Anti-TLR4 VH CDR1 region

<400> SEQUENCE: 19

Gly Phe Pro Ile Gly Gln Gly Tyr Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Anti-TLR4 VH CDR1 region

<400> SEQUENCE: 20

Gly Tyr Pro Ile Trp Gly Gly Tyr Ser
1               5

<210> SEQ ID NO 21
<211> LENGTH: 9
<212> TYPE: PRT
<213> ORGANISM: Artificial Sequence
<220> FEATURE:
<223> OTHER INFORMATION: Anti-TLR4 VH CDR1 region

<400> SEQUENCE: 21

Gly Tyr Pro Ile Gly Gly Gly Tyr Ser
1               5

<210> SEQ ID NO 22
<211> LENGTH: 7
<212> TYPE: PRT
<213> ORGANISM: Artificial Sequence
<220> FEATURE:
<223> OTHER INFORMATION: Anti-TLR4 VH CDR2 region

<400> SEQUENCE: 22
```

```
Ile His Tyr Ser Gly Tyr Thr
1               5

<210> SEQ ID NO 23
<211> LENGTH: 11
<212> TYPE: PRT
<213> ORGANISM: Artificial Sequence
<220> FEATURE:
<223> OTHER INFORMATION: Anti-TLR4 VH CDR3 region
<220> FEATURE:
<221> NAME/KEY: misc_feature
<222> LOCATION: (7)..(7)
<223> OTHER INFORMATION: Xaa may be Asn, Gln, Asp or Glu
<220> FEATURE:
<221> NAME/KEY: misc_feature
<222> LOCATION: (8)..(9)
<223> OTHER INFORMATION: Xaa may be any hydrophobic amino acid

<400> SEQUENCE: 23

Ala Arg Lys Asp Ser Gly Xaa Xaa Xaa Pro Tyr
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Anti-TLR4 VH CDR3 region

<400> SEQUENCE: 24

Ala Arg Lys Asp Ser Gly Asn Tyr Phe Pro Tyr
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Anti-TLR4 VH CDR3 region

<400> SEQUENCE: 25

Ala Arg Lys Asp Ser Gly Arg Leu Leu Pro Tyr
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Anti-TLR4 VH CDR3 region

<400> SEQUENCE: 26

Ala Arg Lys Asp Ser Gly Lys Trp Leu Pro Tyr
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Anti-TLR4 VH CDR3 region

<400> SEQUENCE: 27

Ala Arg Lys Asp Ser Gly His Leu Met Pro Tyr
1               5                   10

<210> SEQ ID NO 28
```

-continued

```
<211> LENGTH: 11
<212> TYPE: PRT
<213> ORGANISM: Artificial Sequence
<220> FEATURE:
<223> OTHER INFORMATION: Anti-TLR4 VH CDR3 region

<400> SEQUENCE: 28

Ala Arg Lys Asp Ser Gly His Asn Tyr Pro Tyr
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Anti-TLR4 VH CDR3 region

<400> SEQUENCE: 29

Ala Arg Lys Asp Ser Gly Lys Asn Phe Pro Tyr
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Anti-TLR4 VH CDR3 region

<400> SEQUENCE: 30

Ala Arg Lys Asp Ser Gly Gln Leu Phe Pro Tyr
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Anti-TLR4 VH CDR3 region

<400> SEQUENCE: 31

Ala Arg Lys Asp Ser Gly His Asn Leu Pro Tyr
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Anti-TLR4 VH CDR3 region

<400> SEQUENCE: 32

Ala Arg Lys Asp Ser Gly Asp Tyr Phe Pro Tyr
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Anti-TLR4 VH CDR3 region

<400> SEQUENCE: 33

Ala Arg Lys Asp Ser Gly Arg Tyr Trp Pro Tyr
1               5                   10

<210> SEQ ID NO 34
<211> LENGTH: 6
```

```
<212> TYPE: PRT
<213> ORGANISM: Artificial Sequence
<220> FEATURE:
<223> OTHER INFORMATION: Anti-TLR4 VL CDR1 region

<400> SEQUENCE: 34

Gln Ser Ile Ser Asp His
1               5

<210> SEQ ID NO 35
<211> LENGTH: 3
<212> TYPE: PRT
<213> ORGANISM: Artificial Sequence
<220> FEATURE:
<223> OTHER INFORMATION: Anti-TLR4 VL CDR2 region

<400> SEQUENCE: 35

Tyr Ala Ser
1

<210> SEQ ID NO 36
<211> LENGTH: 9
<212> TYPE: PRT
<213> ORGANISM: Artificial Sequence
<220> FEATURE:
<223> OTHER INFORMATION: Anti-TLR4 VL CDR3 region
<220> FEATURE:
<221> NAME/KEY: misc_feature
<222> LOCATION: (4)..(4)
<223> OTHER INFORMATION: Xaa may be Tyr or Asn
<220> FEATURE:
<221> NAME/KEY: misc_feature
<222> LOCATION: (5)..(5)
<223> OTHER INFORMATION: Xaa may be Asp or Glu
<220> FEATURE:
<221> NAME/KEY: misc_feature
<222> LOCATION: (6)..(6)
<223> OTHER INFORMATION: Xaa may be Phe or Tyr
<220> FEATURE:
<221> NAME/KEY: misc_feature
<222> LOCATION: (8)..(8)
<223> OTHER INFORMATION: Xaa may be any hydrophobic amino acid

<400> SEQUENCE: 36

Gln Gln Gly Xaa Xaa Xaa Pro Xaa Thr
1               5

<210> SEQ ID NO 37
<211> LENGTH: 9
<212> TYPE: PRT
<213> ORGANISM: Artificial Sequence
<220> FEATURE:
<223> OTHER INFORMATION: Anti-TLR4 VL CDR3 region

<400> SEQUENCE: 37

Gln Gln Gly Asn Asp Phe Pro Val Thr
1               5

<210> SEQ ID NO 38
<211> LENGTH: 9
<212> TYPE: PRT
<213> ORGANISM: Artificial Sequence
<220> FEATURE:
<223> OTHER INFORMATION: Anti-TLR4 VL CDR3 region

<400> SEQUENCE: 38

Gln Gln Gly Tyr Asp Glu Pro Phe Thr
1               5
```

```
<210> SEQ ID NO 39
<211> LENGTH: 9
<212> TYPE: PRT
<213> ORGANISM: Artificial Sequence
<220> FEATURE:
<223> OTHER INFORMATION: Anti-TLR4 VL CDR3 region

<400> SEQUENCE: 39

Gln Gln Gly Tyr Asp Phe Pro Phe Thr
1               5

<210> SEQ ID NO 40
<211> LENGTH: 9
<212> TYPE: PRT
<213> ORGANISM: Artificial Sequence
<220> FEATURE:
<223> OTHER INFORMATION: Anti-TLR4 VL CDR3 region

<400> SEQUENCE: 40

Gln Gln Gly Tyr Asp Tyr Pro Phe Thr
1               5

<210> SEQ ID NO 41
<211> LENGTH: 9
<212> TYPE: PRT
<213> ORGANISM: Artificial Sequence
<220> FEATURE:
<223> OTHER INFORMATION: Anti-TLR4 VL CDR3 region

<400> SEQUENCE: 41

Gln Gln Gly Tyr Glu Phe Pro Phe Thr
1               5

<210> SEQ ID NO 42
<211> LENGTH: 118
<212> TYPE: PRT
<213> ORGANISM: Artificial Sequence
<220> FEATURE:
<223> OTHER INFORMATION: Anti-TLR4 variable heavy chain
<220> FEATURE:
<221> NAME/KEY: misc_feature
<222> LOCATION: (30)..(30)
<223> OTHER INFORMATION: Xaa may be Thr or Ser
<220> FEATURE:
<221> NAME/KEY: misc_feature
<222> LOCATION: (49)..(49)
<223> OTHER INFORMATION: Xaa may be Ile or Met
<220> FEATURE:
<221> NAME/KEY: misc_feature
<222> LOCATION: (68)..(68)
<223> OTHER INFORMATION: Xaa may be Val or Ile
<220> FEATURE:
<221> NAME/KEY: misc_feature
<222> LOCATION: (70)..(70)
<223> OTHER INFORMATION: Xaa may be Met or Ile

<400> SEQUENCE: 42

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Xaa Gly Gly
            20                  25                  30

Tyr Ser Trp His Trp Ile Arg Gln Pro Pro Gly Lys Gly Leu Glu Trp
        35                  40                  45

Xaa Gly Tyr Ile His Tyr Ser Gly Tyr Thr Asp Phe Asn Pro Ser Leu
    50                  55                  60

Lys Thr Arg Xaa Thr Xaa Ser Arg Asp Thr Ser Lys Asn Gln Phe Ser
65                  70                  75                  80
```

```
Leu Lys Leu Ser Ser Val Thr Ala Val Asp Thr Ala Val Tyr Tyr Cys
                85                  90                  95
Ala Arg Lys Asp Pro Ser Asp Gly Phe Pro Tyr Trp Gly Gln Gly Thr
            100                 105                 110
Leu Val Thr Val Ser Ser
        115

<210> SEQ ID NO 43
<211> LENGTH: 118
<212> TYPE: PRT
<213> ORGANISM: Artificial Sequence
<220> FEATURE:
<223> OTHER INFORMATION: Anti-TLR4 variable heavy chain
<220> FEATURE:
<221> NAME/KEY: misc_feature
<222> LOCATION: (24)..(24)
<223> OTHER INFORMATION: Xaa may be Ala or Val
<220> FEATURE:
<221> NAME/KEY: misc_feature
<222> LOCATION: (49)..(49)
<223> OTHER INFORMATION: Xaa may be Val or Met
<220> FEATURE:
<221> NAME/KEY: misc_feature
<222> LOCATION: (79)..(79)
<223> OTHER INFORMATION: Xaa may be Leu or Phe

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Xaa Ser Gly Tyr Ser Ile Thr Gly Gly
            20                  25                  30

Tyr Ser Trp His Trp Val Arg Gln Ala Pro Gly Lys Gly Leu Glu Trp
        35                  40                  45

Xaa Ser Tyr Ile His Tyr Ser Gly Tyr Thr Asp Phe Asn Pro Ser Leu
50                  55                  60

Lys Thr Arg Phe Thr Ile Ser Arg Asp Asn Ser Lys Asn Thr Xaa Tyr
65                  70                  75                  80

Leu Gln Met Asn Ser Leu Arg Ala Glu Asp Thr Ala Val Tyr Tyr Cys
                85                  90                  95

Ala Arg Lys Asp Pro Ser Asp Gly Phe Pro Tyr Trp Gly Gln Gly Thr
            100                 105                 110

Leu Val Thr Val Ser Ser
        115

<210> SEQ ID NO 44
<211> LENGTH: 107
<212> TYPE: PRT
<213> ORGANISM: Artificial Sequence
<220> FEATURE:
<223> OTHER INFORMATION: Anti-TLR4 variable light chain
<220> FEATURE:
<221> NAME/KEY: misc_feature
<222> LOCATION: (49)..(49)
<223> OTHER INFORMATION: Xaa may be Lys or Tyr

<400> SEQUENCE: 44

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asp His
            20                  25                  30

Leu His Trp Tyr Gln Gln Lys Pro Gly Gln Ala Pro Arg Leu Leu Ile
        35                  40                  45

Xaa Tyr Ala Ser His Ala Ile Ser Gly Ile Pro Ala Arg Phe Ser Gly
```

```
                    50                  55                  60
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Asn Gly His Ser Phe Pro Leu
                 85                  90                  95

Thr Phe Gly Gly Gly Thr Lys Val Glu Ile Lys
            100                 105

<210> SEQ ID NO 45
<211> LENGTH: 107
<212> TYPE: PRT
<213> ORGANISM: Artificial Sequence
<220> FEATURE:
<223> OTHER INFORMATION: Anti-TLR4 variable light chain

<400> SEQUENCE: 45

Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Ser Ile Ser Asp His
                 20                  25                  30

Leu His Trp Tyr Gln Gln Lys Pro Asp Gln Ser Pro Lys Leu Leu Ile
             35                  40                  45

Lys Tyr Ala Ser His Ala Ile Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Asn Gly His Ser Phe Pro Leu
                 85                  90                  95

Thr Phe Gly Gly Gly Thr Lys Val Glu Ile Lys
            100                 105

<210> SEQ ID NO 46
<211> LENGTH: 120
<212> TYPE: PRT
<213> ORGANISM: Artificial Sequence
<220> FEATURE:
<223> OTHER INFORMATION: Anti-TLR4 variable heavy chain
<220> FEATURE:
<221> NAME/KEY: misc_feature
<222> LOCATION: (48)..(48)
<223> OTHER INFORMATION: Xaa may be Met or Ile
<220> FEATURE:
<221> NAME/KEY: misc_feature
<222> LOCATION: (74)..(74)
<223> OTHER INFORMATION: Xaa may be Lys or Thr
<220> FEATURE:
<221> NAME/KEY: misc_feature
<222> LOCATION: (81)..(81)
<223> OTHER INFORMATION: Xaa may be Met or Leu

<400> SEQUENCE: 46

Gln Val Gln Leu Val Gln Ser Gly Ala Glu Val Lys Lys Pro Gly Ser
 1               5                  10                  15

Ser Val Lys Val Ser Cys Lys Ala Ser Gly Phe Asn Ile Lys Asp Ser
                 20                  25                  30

Tyr Ile His Trp Val Arg Gln Ala Pro Gly Gln Gly Leu Glu Trp Xaa
             35                  40                  45

Gly Trp Thr Asp Pro Glu Asn Val Asn Ser Ile Tyr Asp Pro Arg Phe
 50                  55                  60

Gln Gly Arg Val Thr Ile Thr Ala Asp Xaa Ser Thr Ser Thr Ala Tyr
 65                  70                  75                  80
```

```
Xaa Glu Leu Ser Ser Leu Arg Ser Glu Asp Thr Ala Val Tyr Tyr Cys
                85                  90                  95

Ala Arg Gly Tyr Asn Gly Val Tyr Tyr Ala Met Asp Tyr Trp Gly Gln
            100                 105                 110

Gly Thr Thr Val Thr Val Ser Ser
        115                 120

<210> SEQ ID NO 47
<211> LENGTH: 5
<212> TYPE: PRT
<213> ORGANISM: Artificial Sequence
<220> FEATURE:
<223> OTHER INFORMATION: Anti-TLR4 VH CDR1 region

<400> SEQUENCE: 47

Asp Ser Tyr Ile His
1               5

<210> SEQ ID NO 48
<211> LENGTH: 17
<212> TYPE: PRT
<213> ORGANISM: Artificial Sequence
<220> FEATURE:
<223> OTHER INFORMATION: Anti-TLR4 VH CDR2 region

<400> SEQUENCE: 48

Trp Thr Asp Pro Glu Asn Val Asn Ser Ile Tyr Asp Pro Arg Phe Gln
1               5                   10                  15

Gly

<210> SEQ ID NO 49
<211> LENGTH: 11
<212> TYPE: PRT
<213> ORGANISM: Artificial Sequence
<220> FEATURE:
<223> OTHER INFORMATION: Anti-TLR4 VH CDR3 region

<400> SEQUENCE: 49

Gly Tyr Asn Gly Val Tyr Tyr Ala Met Asp Tyr
1               5                   10

<210> SEQ ID NO 50
<211> LENGTH: 106
<212> TYPE: PRT
<213> ORGANISM: Artificial Sequence
<220> FEATURE:
<223> OTHER INFORMATION: Anti-TLR4 variable light chain
<220> FEATURE:
<221> NAME/KEY: misc_feature
<222> LOCATION: (70)..(70)
<223> OTHER INFORMATION: Xaa may be Phe or Tyr

<400> SEQUENCE: 50

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ile Tyr Met
            20                  25                  30

His Trp Tyr Gln Gln Lys Pro Gly Gln Ala Pro Arg Leu Leu Ile Tyr
        35                  40                  45

Arg Thr Tyr Asn Leu Ala Ser Gly Ile Pro Ala Arg Phe Ser Gly Ser
    50                  55                  60

Gly Ser Gly Thr Asp Xaa Thr Leu Thr Ile Ser Ser Leu Glu Pro Glu
65                  70                  75                  80
```

```
Asp Phe Ala Val Tyr Tyr Cys His Gln Trp Ser Ser Phe Pro Tyr Thr
            85                  90                  95

Phe Gly Gln Gly Thr Lys Val Glu Ile Lys
            100                 105

<210> SEQ ID NO 51
<211> LENGTH: 10
<212> TYPE: PRT
<213> ORGANISM: Artificial Sequence
<220> FEATURE:
<223> OTHER INFORMATION: Anti-TLR4 VL CDR1 region

<400> SEQUENCE: 51

Ser Ala Ser Ser Ser Val Ile Tyr Met His
1               5                   10

<210> SEQ ID NO 52
<211> LENGTH: 7
<212> TYPE: PRT
<213> ORGANISM: Artificial Sequence
<220> FEATURE:
<223> OTHER INFORMATION: Anti-TLR4 VL CDR2 region

<400> SEQUENCE: 52

Arg Thr Tyr Asn Leu Ala Ser
1               5

<210> SEQ ID NO 53
<211> LENGTH: 9
<212> TYPE: PRT
<213> ORGANISM: Artificial Sequence
<220> FEATURE:
<223> OTHER INFORMATION: Anti-TLR4 VL CDR3 region

<400> SEQUENCE: 53

His Gln Trp Ser Ser Phe Pro Tyr Thr
1               5

<210> SEQ ID NO 54
<211> LENGTH: 121
<212> TYPE: PRT
<213> ORGANISM: Artificial Sequence
<220> FEATURE:
<223> OTHER INFORMATION: Anti-TLR4 variable heavy chain
<220> FEATURE:
<221> NAME/KEY: misc_feature
<222> LOCATION: (30)..(30)
<223> OTHER INFORMATION: Xaa may be Ser or Thr
<220> FEATURE:
<221> NAME/KEY: misc_feature
<222> LOCATION: (71)..(71)
<223> OTHER INFORMATION: Xaa may be Ile or Phe
<220> FEATURE:
<221> NAME/KEY: misc_feature
<222> LOCATION: (98)..(98)
<223> OTHER INFORMATION: Xaa may be Ile or Ala

<400> SEQUENCE: 54

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Xaa Thr Tyr
            20                  25                  30

Asn Ile Gly Val Gly Trp Ile Arg Gln Pro Pro Gly Lys Ala Leu Glu
        35                  40                  45

Trp Leu Ala His Ile Trp Trp Asn Asp Asn Ile Tyr Tyr Asn Thr Val
    50                  55                  60
```

```
Leu Lys Ser Arg Leu Thr Xaa Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Xaa Arg Met Ala Glu Gly Arg Tyr Asp Ala Met Asp Tyr Trp Gly
        100                 105                 110

Gln Gly Thr Leu Val Thr Val Ser Ser
        115                 120

<210> SEQ ID NO 55
<211> LENGTH: 7
<212> TYPE: PRT
<213> ORGANISM: Artificial Sequence
<220> FEATURE:
<223> OTHER INFORMATION: Anti-TLR4 VH CDR1 region

<400> SEQUENCE: 55

Thr Tyr Asn Ile Gly Val Gly
1               5

<210> SEQ ID NO 56
<211> LENGTH: 16
<212> TYPE: PRT
<213> ORGANISM: Artificial Sequence
<220> FEATURE:
<223> OTHER INFORMATION: Anti-TLR4 VH CDR2 region

<400> SEQUENCE: 56

His Ile Trp Trp Asn Asp Asn Ile Tyr Tyr Asn Thr Val Leu Lys Ser
1               5                   10                  15

<210> SEQ ID NO 57
<211> LENGTH: 11
<212> TYPE: PRT
<213> ORGANISM: Artificial Sequence
<220> FEATURE:
<223> OTHER INFORMATION: Anti-TLR4 VH CDR3 region

<400> SEQUENCE: 57

Met Ala Glu Gly Arg Tyr Asp Ala Met Asp Tyr
1               5                   10

<210> SEQ ID NO 58
<211> LENGTH: 121
<212> TYPE: PRT
<213> ORGANISM: Artificial Sequence
<220> FEATURE:
<223> OTHER INFORMATION: Anti-TLR4 variable heavy chain
<220> FEATURE:
<221> NAME/KEY: misc_feature
<222> LOCATION: (24)..(24)
<223> OTHER INFORMATION: Xaa may be Phe or Ala
<220> FEATURE:
<221> NAME/KEY: misc_feature
<222> LOCATION: (50)..(50)
<223> OTHER INFORMATION: Xaa may be Val or Leu
<220> FEATURE:
<221> NAME/KEY: misc_feature
<222> LOCATION: (71)..(71)
<223> OTHER INFORMATION: Xaa may be Ile or Phe
<220> FEATURE:
<221> NAME/KEY: misc_feature
<222> LOCATION: (73)..(73)
<223> OTHER INFORMATION: Xaa may be Lys or Arg
<220> FEATURE:
<221> NAME/KEY: misc_feature
<222> LOCATION: (80)..(80)
<223> OTHER INFORMATION: Xaa may be Leu or Val
<220> FEATURE:
```

<221> NAME/KEY: misc_feature
<222> LOCATION: (98)..(98)
<223> OTHER INFORMATION: Xaa may be Ile or Ala

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Xaa Ser Gly Phe Ser Leu Thr Thr Tyr
            20                  25                  30

Asn Ile Gly Val Gly Trp Val Arg Gln Ala Pro Gly Lys Gly Leu Glu
        35                  40                  45

Trp Xaa Ser His Ile Trp Trp Asn Asp Asn Ile Tyr Tyr Asn Thr Val
    50                  55                  60

Leu Lys Ser Arg Leu Thr Xaa Ser Xaa Asp Asn Ser Lys Asn Thr Xaa
65                  70                  75                  80

Tyr Leu Gln Met Asn Ser Leu Arg Ala Glu Asp Thr Ala Val Tyr Tyr
                85                  90                  95

Cys Xaa Arg Met Ala Glu Gly Arg Tyr Asp Ala Met Asp Tyr Trp Gly
        100                 105                 110

Gln Gly Thr Leu Val Thr Val Ser Ser
        115                 120

<210> SEQ ID NO 59
<211> LENGTH: 7
<212> TYPE: PRT
<213> ORGANISM: Artificial Sequence
<220> FEATURE:
<223> OTHER INFORMATION: Anti-TLR4 VH CDR1 region

<400> SEQUENCE: 59

Thr Tyr Asn Ile Gly Val Gly
1               5

<210> SEQ ID NO 60
<211> LENGTH: 16
<212> TYPE: PRT
<213> ORGANISM: Artificial Sequence
<220> FEATURE:
<223> OTHER INFORMATION: Anti-TLR4 VH CDR2 region

<400> SEQUENCE: 60

His Ile Trp Trp Asn Asp Asn Ile Tyr Tyr Asn Thr Val Leu Lys Ser
1               5                   10                  15

<210> SEQ ID NO 61
<211> LENGTH: 11
<212> TYPE: PRT
<213> ORGANISM: Artificial Sequence
<220> FEATURE:
<223> OTHER INFORMATION: Anti-TLR4 VH CDR3 region

<400> SEQUENCE: 61

Met Ala Glu Gly Arg Tyr Asp Ala Met Asp Tyr
1               5                   10

<210> SEQ ID NO 62
<211> LENGTH: 107
<212> TYPE: PRT
<213> ORGANISM: Artificial Sequence
<220> FEATURE:
<223> OTHER INFORMATION: Anti-TLR4 variable light chain
<220> FEATURE:
<221> NAME/KEY: misc_feature
<222> LOCATION: (71)..(71)

<223> OTHER INFORMATION: Xaa may be Phe or Tyr
<220> FEATURE:
<221> NAME/KEY: misc_feature
<222> LOCATION: (87)..(87)
<223> OTHER INFORMATION: Xaa may be Tyr or Phe

<400> SEQUENCE: 62

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Thr Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
50                  55                  60

Ser Gly Ser Gly Thr Asp Xaa Thr Leu Thr Ile Ser Ser Leu Gln Pro
65                  70                  75                  80

Glu Asp Phe Ala Thr Tyr Xaa Cys Gln Gln Gly Asn Thr Phe Pro Trp
                85                  90                  95

Thr Phe Gly Gly Gly Thr Lys Val Glu Ile Lys
            100                 105

<210> SEQ ID NO 63
<211> LENGTH: 11
<212> TYPE: PRT
<213> ORGANISM: Artificial Sequence
<220> FEATURE:
<223> OTHER INFORMATION: Anti-TLR4 VL CDR1 region

<400> SEQUENCE: 63

Arg Ala Ser Gln Asp Ile Thr Asn Tyr Leu Asn
1               5                   10

<210> SEQ ID NO 64
<211> LENGTH: 7
<212> TYPE: PRT
<213> ORGANISM: Artificial Sequence
<220> FEATURE:
<223> OTHER INFORMATION: Anti-TLR4 VL CDR2 region

<400> SEQUENCE: 64

Tyr Thr Ser Lys Leu His Ser
1               5

<210> SEQ ID NO 65
<211> LENGTH: 9
<212> TYPE: PRT
<213> ORGANISM: Artificial Sequence
<220> FEATURE:
<223> OTHER INFORMATION: Anti-TLR4 VL CDR3 region

<400> SEQUENCE: 65

Gln Gln Gly Asn Thr Phe Pro Trp Thr
1               5

<210> SEQ ID NO 66
<211> LENGTH: 354
<212> TYPE: DNA
<213> ORGANISM: Artificial Sequence
<220> FEATURE:
<223> OTHER INFORMATION: Anti-TLR4 variable heavy chain

<400> SEQUENCE: 66
caggtgcagc ttcaggagtc cggcccagga ctggtgaagc cttcggacac cctgtccctc    60

```
acctgcgctg tctctggtta ctccatcacc ggtggttata gctggcactg gatacggcag    120
cccccaggga agggactgga gtggatgggg tatatcccact acagtggtta cactgacttc    180 aaccccctccc tcaagactcg aatcaccata tcacgtgaca cgtccaagaa ccagttctcc    240
ctgaagctga gctctgtgac cgctgtggac actgcagtgt attactgtgc gagaaaagat    300
ccgtccgacg cctttcctta ctggggccaa gggactctgg tcactgtctc ttcc          354
```

<210> SEQ ID NO 67
<211> LENGTH: 118
<212> TYPE: PRT
<213> ORGANISM: Artificial Sequence
<220> FEATURE:
<223> OTHER INFORMATION: Anti-TLR4 variable heavy chain

<400> SEQUENCE: 67

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Pro Ser Glu Gly Phe Pro Tyr Trp Gly Gln Gly Thr
            100                 105                 110

Leu Val Thr Val Ser Ser
        115
```

<210> SEQ ID NO 68
<211> LENGTH: 354
<212> TYPE: DNA
<213> ORGANISM: Artificial Sequence
<220> FEATURE:
<223> OTHER INFORMATION: Anti-TLR4 variable heavy chain

<400> SEQUENCE: 68

```
caggtgcagc ttcaggagtc cggcccagga ctggtgaagc cttcggacac cctgtccctc     60
acctgcgctg tctctggtta ctccatcacc ggtggttata gctggcactg gatacggcag    120
cccccaggga agggactgga gtggatgggg tatatccact acagtggtta cactgacttc    180 aaccccctccc tcaagactcg aatcaccata tcacgtgaca cgtccaagaa ccagttctcc    240
ctgaagctga gctctgtgac cgctgtggac actgcagtgt attactgtgc gagaaaagat    300
ccgtccgagg gatttcctta ctggggccaa gggactctgg tcactgtctc ttcc          354
```

<210> SEQ ID NO 69
<211> LENGTH: 107
<212> TYPE: PRT
<213> ORGANISM: Artificial Sequence
<220> FEATURE:
<223> OTHER INFORMATION: Anti-TLR4 variable light chain

<400> SEQUENCE: 69

```
Glu Ile Val Leu Thr Gln Ser Pro Asp Phe Gln Ser Val Thr Pro Lys
1               5                   10                  15
```

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Asn Ser His Ser Phe Pro Leu
                85                  90                  95

Thr Phe Gly Gly Gly Thr Lys Val Glu Ile Lys
            100                 105

<210> SEQ ID NO 70
<211> LENGTH: 321
<212> TYPE: DNA
<213> ORGANISM: Artificial Sequence
<220> FEATURE:
<223> OTHER INFORMATION: Anti-TLR4 variable light chain

<400> SEQUENCE: 70
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagaat agtcacagtt ttccgctcac tttcggcgga    300
gggaccaagg tggagatcaa a                                               321

<210> SEQ ID NO 71
<211> LENGTH: 321
<212> TYPE: DNA
<213> ORGANISM: Artificial Sequence
<220> FEATURE:
<223> OTHER INFORMATION: Anti-TLR4 variable light chain

<400> SEQUENCE: 71
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag ggtcacagtt ttccgctcac tttcggcgga    300
gggaccaagg tggagatcaa a                                               321

<210> SEQ ID NO 72
<211> LENGTH: 107
<212> TYPE: PRT
<213> ORGANISM: Artificial Sequence
<220> FEATURE:
<223> OTHER INFORMATION: Anti-TLR4 variable light chain

<400> SEQUENCE: 72

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
            35                  40                  45

Lys Tyr Ala Ser His Ala Ile Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Asn Ser Ser Ser Phe Pro Leu
                 85                  90                  95

Thr Phe Gly Gly Gly Thr Lys Val Glu Ile Lys
            100                 105

<210> SEQ ID NO 73
<211> LENGTH: 321
<212> TYPE: DNA
<213> ORGANISM: Artificial Sequence
<220> FEATURE:
<223> OTHER INFORMATION: Anti-TLR4 variable light chain

<400> SEQUENCE: 73
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagaat agtagtagtt ttccgctcac tttcggcgga     300
gggaccaagg tggagatcaa a                                               321

<210> SEQ ID NO 74
<211> LENGTH: 107
<212> TYPE: PRT
<213> ORGANISM: Artificial Sequence
<220> FEATURE:
<223> OTHER INFORMATION: Anti-TLR4 variable light chain

<400> SEQUENCE: 74

Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Ser Ile Ser Asp His
                 20                  25                  30

Leu His Trp Tyr Gln Gln Lys Pro Asp Gln Ser Pro Lys Leu Leu Ile
            35                  40                  45

Lys Tyr Ala Ser His Ala Ile Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Ser His Ser Phe Pro Leu
                 85                  90                  95

Thr Phe Gly Gly Gly Thr Lys Val Glu Ile Lys
            100                 105

<210> SEQ ID NO 75
<211> LENGTH: 321
<212> TYPE: DNA
<213> ORGANISM: Artificial Sequence
<220> FEATURE:
<223> OTHER INFORMATION: Anti-TLR4 variable light chain

<400> SEQUENCE: 75
gaaattgtgt tgacgcagtc tccagacttt cagtctgtga ctccaaagga aaaagtcacc      60

-continued

```
atcacctgca gggccagtca gagtatcagc gaccacttac actggtacca acagaaacct    120
gatcagtctc ccaagctcct catcaaatat gcttcccatg ccatttctgg ggtcccatcg    180
aggttcagtg gcagtgggtc tgggacagac ttcactctca ccatcaatag cctagaggct    240
gaagatgctg caacgtatta ctgtcagcag agtcacagtt ttccgctcac tttcggcgga    300
gggaccaagg tggagatcaa a                                              321
```

<210> SEQ ID NO 76
<211> LENGTH: 839
<212> TYPE: PRT
<213> ORGANISM: Homo sapiens

<400> SEQUENCE: 76

| Met | Met | Ser | Ala | Ser | Arg | Leu | Ala | Gly | Thr | Leu | Ile | Pro | Ala | Met | Ala |
|---|---|---|---|---|---|---|---|---|---|---|---|---|---|---|---|
| 1 | | | | 5 | | | | | 10 | | | | | 15 | |

| Phe | Leu | Ser | Cys | Val | Arg | Pro | Glu | Ser | Trp | Glu | Pro | Cys | Val | Glu | Val |
|---|---|---|---|---|---|---|---|---|---|---|---|---|---|---|---|
| | | | 20 | | | | | 25 | | | | | 30 | | |

| Val | Pro | Asn | Ile | Thr | Tyr | Gln | Cys | Met | Glu | Leu | Asn | Phe | Tyr | Lys | Ile |
|---|---|---|---|---|---|---|---|---|---|---|---|---|---|---|---|
| | | 35 | | | | | 40 | | | | | 45 | | | |

| Pro | Asp | Asn | Leu | Pro | Phe | Ser | Thr | Lys | Asn | Leu | Asp | Leu | Ser | Phe | Asn |
|---|---|---|---|---|---|---|---|---|---|---|---|---|---|---|---|
| | 50 | | | | | 55 | | | | | 60 | | | | |

| Pro | Leu | Arg | His | Leu | Gly | Ser | Tyr | Ser | Phe | Phe | Ser | Phe | Pro | Glu | Leu |
|---|---|---|---|---|---|---|---|---|---|---|---|---|---|---|---|
| 65 | | | | | 70 | | | | | 75 | | | | | 80 |

| Gln | Val | Leu | Asp | Leu | Ser | Arg | Cys | Glu | Ile | Gln | Thr | Ile | Glu | Asp | Gly |
|---|---|---|---|---|---|---|---|---|---|---|---|---|---|---|---|
| | | | | 85 | | | | | 90 | | | | | 95 | |

| Ala | Tyr | Gln | Ser | Leu | Ser | His | Leu | Ser | Thr | Leu | Ile | Leu | Thr | Gly | Asn |
|---|---|---|---|---|---|---|---|---|---|---|---|---|---|---|---|
| | | | 100 | | | | | 105 | | | | | 110 | | |

| Pro | Ile | Gln | Ser | Leu | Ala | Leu | Gly | Ala | Phe | Ser | Gly | Leu | Ser | Ser | Leu |
|---|---|---|---|---|---|---|---|---|---|---|---|---|---|---|---|
| | | 115 | | | | | 120 | | | | | 125 | | | |

| Gln | Lys | Leu | Val | Ala | Val | Glu | Thr | Asn | Leu | Ala | Ser | Leu | Glu | Asn | Phe |
|---|---|---|---|---|---|---|---|---|---|---|---|---|---|---|---|
| | 130 | | | | | 135 | | | | | 140 | | | | |

| Pro | Ile | Gly | His | Leu | Lys | Thr | Leu | Lys | Glu | Leu | Asn | Val | Ala | His | Asn |
|---|---|---|---|---|---|---|---|---|---|---|---|---|---|---|---|
| 145 | | | | | 150 | | | | | 155 | | | | | 160 |

| Leu | Ile | Gln | Ser | Phe | Lys | Leu | Pro | Glu | Tyr | Phe | Ser | Asn | Leu | Thr | Asn |
|---|---|---|---|---|---|---|---|---|---|---|---|---|---|---|---|
| | | | | 165 | | | | | 170 | | | | | 175 | |

| Leu | Glu | His | Leu | Asp | Leu | Ser | Ser | Asn | Lys | Ile | Gln | Ser | Ile | Tyr | Cys |
|---|---|---|---|---|---|---|---|---|---|---|---|---|---|---|---|
| | | | 180 | | | | | 185 | | | | | 190 | | |

| Thr | Asp | Leu | Arg | Val | Leu | His | Gln | Met | Pro | Leu | Leu | Asn | Leu | Ser | Leu |
|---|---|---|---|---|---|---|---|---|---|---|---|---|---|---|---|
| | | 195 | | | | | 200 | | | | | 205 | | | |

| Asp | Leu | Ser | Leu | Asn | Pro | Met | Asn | Phe | Ile | Gln | Pro | Gly | Ala | Phe | Lys |
|---|---|---|---|---|---|---|---|---|---|---|---|---|---|---|---|
| | 210 | | | | | 215 | | | | | 220 | | | | |

| Glu | Ile | Arg | Leu | His | Lys | Leu | Thr | Leu | Arg | Asn | Asn | Phe | Asp | Ser | Leu |
|---|---|---|---|---|---|---|---|---|---|---|---|---|---|---|---|
| 225 | | | | | 230 | | | | | 235 | | | | | 240 |

| Asn | Val | Met | Lys | Thr | Cys | Ile | Gln | Gly | Leu | Ala | Gly | Leu | Glu | Val | His |
|---|---|---|---|---|---|---|---|---|---|---|---|---|---|---|---|
| | | | | 245 | | | | | 250 | | | | | 255 | |

| Arg | Leu | Val | Leu | Gly | Glu | Phe | Arg | Asn | Glu | Gly | Asn | Leu | Glu | Lys | Phe |
|---|---|---|---|---|---|---|---|---|---|---|---|---|---|---|---|
| | | | 260 | | | | | 265 | | | | | 270 | | |

| Asp | Lys | Ser | Ala | Leu | Glu | Gly | Leu | Cys | Asn | Leu | Thr | Ile | Glu | Glu | Phe |
|---|---|---|---|---|---|---|---|---|---|---|---|---|---|---|---|
| | | 275 | | | | | 280 | | | | | 285 | | | |

| Arg | Leu | Ala | Tyr | Leu | Asp | Tyr | Tyr | Leu | Asp | Asp | Ile | Ile | Asp | Leu | Phe |
|---|---|---|---|---|---|---|---|---|---|---|---|---|---|---|---|
| | 290 | | | | | 295 | | | | | 300 | | | | |

| Asn | Cys | Leu | Thr | Asn | Val | Ser | Ser | Phe | Ser | Leu | Val | Ser | Val | Thr | Ile |
|---|---|---|---|---|---|---|---|---|---|---|---|---|---|---|---|
| 305 | | | | | 310 | | | | | 315 | | | | | 320 |

```
Glu Arg Val Lys Asp Phe Ser Tyr Asn Phe Gly Trp Gln His Leu Glu
            325                 330                 335

Leu Val Asn Cys Lys Phe Gly Gln Phe Pro Thr Leu Lys Leu Lys Ser
            340                 345                 350

Leu Lys Arg Leu Thr Phe Thr Ser Asn Lys Gly Gly Asn Ala Phe Ser
            355                 360                 365

Glu Val Asp Leu Pro Ser Leu Glu Phe Leu Asp Leu Ser Arg Asn Gly
            370                 375                 380

Leu Ser Phe Lys Gly Cys Cys Ser Gln Ser Asp Phe Gly Thr Thr Ser
385                 390                 395                 400

Leu Lys Tyr Leu Asp Leu Ser Phe Asn Gly Val Ile Thr Met Ser Ser
            405                 410                 415

Asn Phe Leu Gly Leu Glu Gln Leu Glu His Leu Asp Phe Gln His Ser
            420                 425                 430

Asn Leu Lys Gln Met Ser Glu Phe Ser Val Phe Leu Ser Leu Arg Asn
            435                 440                 445

Leu Ile Tyr Leu Asp Ile Ser His Thr His Thr Arg Val Ala Phe Asn
            450                 455                 460

Gly Ile Phe Asn Gly Leu Ser Ser Leu Glu Val Leu Lys Met Ala Gly
465                 470                 475                 480

Asn Ser Phe Gln Glu Asn Phe Leu Pro Asp Ile Phe Thr Glu Leu Arg
            485                 490                 495

Asn Leu Thr Phe Leu Asp Leu Ser Gln Cys Gln Leu Glu Gln Leu Ser
            500                 505                 510

Pro Thr Ala Phe Asn Ser Leu Ser Ser Leu Gln Val Leu Asn Met Ser
            515                 520                 525

His Asn Asn Phe Phe Ser Leu Asp Thr Phe Pro Tyr Lys Cys Leu Asn
            530                 535                 540

Ser Leu Gln Val Leu Asp Tyr Ser Leu Asn His Ile Met Thr Ser Lys
545                 550                 555                 560

Lys Gln Glu Leu Gln His Phe Pro Ser Ser Leu Ala Phe Leu Asn Leu
            565                 570                 575

Thr Gln Asn Asp Phe Ala Cys Thr Cys Glu His Gln Ser Phe Leu Gln
            580                 585                 590

Trp Ile Lys Asp Gln Arg Gln Leu Leu Val Glu Val Glu Arg Met Glu
            595                 600                 605

Cys Ala Thr Pro Ser Asp Lys Gln Gly Met Pro Val Leu Ser Leu Asn
            610                 615                 620

Ile Thr Cys Gln Met Asn Lys Thr Ile Ile Gly Val Ser Val Leu Ser
625                 630                 635                 640

Val Leu Val Val Ser Val Val Ala Val Leu Val Tyr Lys Phe Tyr Phe
            645                 650                 655

His Leu Met Leu Leu Ala Gly Cys Ile Lys Tyr Gly Arg Gly Glu Asn
            660                 665                 670

Ile Tyr Asp Ala Phe Val Ile Tyr Ser Ser Gln Asp Glu Asp Trp Val
            675                 680                 685

Arg Asn Glu Leu Val Lys Asn Leu Glu Glu Gly Val Pro Pro Phe Gln
            690                 695                 700

Leu Cys Leu His Tyr Arg Asp Phe Ile Pro Gly Val Ala Ile Ala Ala
705                 710                 715                 720

Asn Ile Ile His Glu Gly Phe His Lys Ser Arg Lys Val Ile Val Val
            725                 730                 735

Val Ser Gln His Phe Ile Gln Ser Arg Trp Cys Ile Phe Glu Tyr Glu
```

```
            740                 745                 750
Ile Ala Gln Thr Trp Gln Phe Leu Ser Ser Arg Ala Gly Ile Ile Phe
            755                 760                 765

Ile Val Leu Gln Lys Val Glu Lys Thr Leu Leu Arg Gln Gln Val Glu
        770                 775                 780

Leu Tyr Arg Leu Leu Ser Arg Asn Thr Tyr Leu Glu Trp Glu Asp Ser
785                 790                 795                 800

Val Leu Gly Arg His Ile Phe Trp Arg Leu Arg Lys Ala Leu Leu
                805                 810                 815

Asp Gly Lys Ser Trp Asn Pro Glu Gly Thr Val Gly Thr Gly Cys Asn
                820                 825                 830

Trp Gln Glu Ala Thr Ser Ile
            835

<210> SEQ ID NO 77
<211> LENGTH: 826
<212> TYPE: PRT
<213> ORGANISM: Cynomolgus sp.

<400> SEQUENCE: 77

Met Thr Ser Ala Leu Arg Leu Ala Gly Thr Leu Ile Pro Ala Met Ala
1               5                   10                  15

Phe Leu Ser Cys Val Arg Pro Glu Ser Trp Glu Pro Cys Val Glu Val
            20                  25                  30

Val Pro Asn Ile Thr Tyr Gln Cys Met Glu Leu Lys Phe Tyr Lys Ile
        35                  40                  45

Pro Asp Asn Ile Pro Phe Ser Thr Lys Asn Leu Asp Leu Ser Phe Asn
    50                  55                  60

Pro Leu Arg His Leu Gly Ser Tyr Ser Phe Leu Arg Phe Pro Glu Leu
65                  70                  75                  80

Gln Val Leu Asp Leu Ser Arg Cys Glu Ile Gln Thr Ile Glu Asp Gly
                85                  90                  95

Ala Tyr Gln Ser Leu Ser His Leu Ser Thr Leu Ile Leu Thr Gly Asn
            100                 105                 110

Pro Ile Gln Ser Leu Ala Leu Gly Ala Phe Ser Gly Leu Ser Ser Leu
        115                 120                 125

Gln Lys Leu Val Ala Val Glu Thr Asn Leu Ala Ser Leu Glu Asn Phe
    130                 135                 140

Pro Ile Gly His Leu Lys Thr Leu Lys Glu Leu Asn Val Ala His Asn
145                 150                 155                 160

Leu Ile Gln Ser Phe Lys Leu Pro Glu Tyr Phe Ser Asn Leu Thr Asn
                165                 170                 175

Leu Glu His Leu Asp Leu Ser Ser Asn Lys Ile Gln Asn Ile Tyr Cys
            180                 185                 190

Lys Asp Leu Gln Val Leu His Gln Met Pro Leu Ser Asn Leu Ser Leu
        195                 200                 205

Asp Leu Ser Leu Asn Pro Ile Asn Phe Ile Gln Pro Gly Ala Phe Lys
    210                 215                 220

Glu Ile Arg Leu His Lys Leu Thr Leu Arg Ser Asn Phe Asp Asp Leu
225                 230                 235                 240

Asn Val Met Lys Thr Cys Ile Gln Gly Leu Ala Gly Leu Glu Val His
                245                 250                 255

Arg Leu Val Leu Gly Glu Phe Arg Asn Glu Arg Asn Leu Glu Glu Phe
            260                 265                 270
```

```
Asp Lys Ser Ser Leu Glu Gly Leu Cys Asn Leu Thr Ile Glu Glu Phe
            275                 280                 285

Arg Leu Thr Tyr Leu Asp Cys Tyr Leu Asp Asn Ile Ile Asp Leu Phe
        290                 295                 300

Asn Cys Leu Ala Asn Val Ser Ser Phe Ser Leu Val Ser Val Asn Ile
305                 310                 315                 320

Lys Arg Val Glu Asp Phe Ser Tyr Asn Phe Arg Trp Gln His Leu Glu
                325                 330                 335

Leu Val Asn Cys Lys Phe Glu Gln Phe Pro Thr Leu Glu Leu Lys Ser
            340                 345                 350

Leu Lys Arg Leu Thr Phe Thr Ala Asn Lys Gly Gly Asn Ala Phe Ser
        355                 360                 365

Glu Val Asp Leu Pro Ser Leu Glu Phe Leu Asp Leu Ser Arg Asn Gly
    370                 375                 380

Leu Ser Phe Lys Gly Cys Cys Ser Gln Ser Asp Phe Gly Thr Thr Ser
385                 390                 395                 400

Leu Lys Tyr Leu Asp Leu Ser Phe Asn Asp Val Ile Thr Met Ser Ser
                405                 410                 415

Asn Phe Leu Gly Leu Glu Gln Leu Glu His Leu Asp Phe Gln His Ser
            420                 425                 430

Asn Leu Lys Gln Met Ser Gln Phe Ser Val Phe Leu Ser Leu Arg Asn
        435                 440                 445

Leu Ile Tyr Leu Asp Ile Ser His Thr His Thr Arg Val Ala Phe Asn
    450                 455                 460

Gly Ile Phe Asp Gly Leu Leu Ser Leu Lys Val Leu Lys Met Ala Gly
465                 470                 475                 480

Asn Ser Phe Gln Glu Asn Phe Leu Pro Asp Ile Phe Thr Asp Leu Lys
                485                 490                 495

Asn Leu Thr Phe Leu Asp Leu Ser Gln Cys Gln Leu Glu Gln Leu Ser
            500                 505                 510

Pro Thr Ala Phe Asp Thr Leu Asn Lys Leu Gln Val Leu Asn Met Ser
        515                 520                 525

His Asn Asn Phe Phe Ser Leu Asp Thr Phe Pro Tyr Lys Cys Leu Pro
    530                 535                 540

Ser Leu Gln Val Leu Asp Tyr Ser Leu Asn His Ile Met Thr Ser Asn
545                 550                 555                 560

Asn Gln Glu Leu Gln His Phe Pro Ser Ser Leu Ala Phe Leu Asn Leu
                565                 570                 575

Thr Gln Asn Asp Phe Ala Cys Thr Cys Glu His Gln Ser Phe Leu Gln
            580                 585                 590

Trp Ile Lys Asp Gln Arg Gln Leu Leu Val Glu Ala Glu Arg Met Glu
        595                 600                 605

Cys Ala Thr Pro Ser Asp Lys Gln Gly Met Pro Val Leu Ser Leu Asn
    610                 615                 620

Ile Thr Cys Gln Met Asn Lys Thr Ile Ile Gly Val Ser Val Phe Ser
625                 630                 635                 640

Val Leu Val Val Ser Val Val Ala Val Leu Val Tyr Lys Phe Tyr Phe
                645                 650                 655

His Leu Met Leu Leu Ala Gly Cys Ile Lys Tyr Gly Arg Gly Glu Asn
            660                 665                 670

Ile Tyr Asp Ala Phe Val Ile Tyr Ser Ser Gln Asp Glu Asp Trp Val
        675                 680                 685

Arg Asn Glu Leu Val Lys Asn Leu Glu Glu Gly Val Pro Pro Phe Gln
```

```
Leu Cys Leu His Tyr Arg Asp Phe Ile Pro Gly Val Ala Ile Ala Ala
705                 710                 715                 720

Asn Ile Ile His Glu Gly Phe His Lys Ser Arg Lys Val Ile Val Val
            725                 730                 735

Val Ser Gln His Phe Ile Gln Ser Arg Trp Cys Ile Phe Glu Tyr Glu
            740                 745                 750

Ile Ala Gln Thr Trp Gln Phe Leu Ser Ser Arg Ala Gly Ile Ile Phe
            755                 760                 765

Ile Val Leu Gln Lys Val Glu Lys Thr Leu Leu Arg Gln Gln Val Glu
            770                 775                 780

Leu Tyr Arg Leu Leu Ser Arg Asn Thr Tyr Leu Glu Trp Glu Asp Ser
785                 790                 795                 800

Val Leu Gly Gln His Ile Phe Trp Arg Arg Leu Arg Lys Ala Leu Leu
                805                 810                 815

Asp Gly Lys Ser Trp Asn Pro Glu Glu Gln
            820                 825
```

<210> SEQ ID NO 78
<211> LENGTH: 118
<212> TYPE: PRT
<213> ORGANISM: Artificial Sequence
<220> FEATURE:
<223> OTHER INFORMATION: Anti-TLR4 variable heavy chain

<400> SEQUENCE: 78

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser
        115
```

<210> SEQ ID NO 79
<211> LENGTH: 354
<212> TYPE: DNA
<213> ORGANISM: Artificial Sequence
<220> FEATURE:
<223> OTHER INFORMATION: Anti-TLR4 variable heavy chain

<400> SEQUENCE: 79

```
caggtgcagc tccaggagtc cggcccagga ctggtgaagc cttcggacac cctgtccctc      60
acctgcgctg tctctggtta ctccatcacc ggtggttata gctggcactg gatacggcag     120
cccccaggga agggactgga gtggatgggg tatatccact acagtggtta cactgacttc     180 aaccctccc tcaagactcg aatcaccata tcacgtgaca cgtccaagaa ccagttctcc     240
ctgaagctga gctctgtgac cgctgtggac actgcagtgt attactgtgc gagaaaagat     300
```

```
tcgggcaact acttcccttta ctggggccaa gggactctgg tcactgtctc ttcc        354
```

<210> SEQ ID NO 80
<211> LENGTH: 321
<212> TYPE: DNA
<213> ORGANISM: Artificial Sequence
<220> FEATURE:
<223> OTHER INFORMATION: Anti-TLR4 variable light chain

<400> SEQUENCE: 80

```
gaaattgtgt tgacgcagtc tccagacttt cagtctgtga ctccaaagga aaaagtcacc    60
atcacctgca gggccagtca gagtatcagc gaccacttac actggtacca acagaaacct   120
gatcagtctc ccaagctcct catcaaatat gcttcccatg ccatttctgg ggtcccatcg   180
aggttcagtg gcagtgggtc tgggacagac ttcactctca ccatcaatag cctagaggct   240
gaagatgctg caacgtatta ctgtcagcag ggtcacagtt ttccgctcac tttcggcgga   300
gggaccaagg tggagatcaa a                                              321
```

<210> SEQ ID NO 81
<211> LENGTH: 354
<212> TYPE: DNA
<213> ORGANISM: Artificial Sequence
<220> FEATURE:
<223> OTHER INFORMATION: Anti-TLR4 variable heavy chain

<400> SEQUENCE: 81

```
caggtgcagc ttcaggagtc cggcccagga ctggtgaagc cttcggacac cctgtccctc    60
acctgcgctg tctctggtta ctccatcacc ggtggttata gctggcactg gatacggcag   120
cccccaggga agggactgga gtggatgggg tatatccact acagtggtta cactgacttc   180
aaccccctcc tcaagactcg aatcaccata tcacgtgaca cgtccaagaa ccagttctcc   240
ctgaagctga gctctgtgac cgctgtggac actgcagtgt attactgtgc gagaaaagat   300
tccggccgcc tcctccctta ctggggccaa gggactctgg tcactgtctc ttcc          354
```

<210> SEQ ID NO 82
<211> LENGTH: 118
<212> TYPE: PRT
<213> ORGANISM: Artificial Sequence
<220> FEATURE:
<223> OTHER INFORMATION: Anti-TLR4 variable heavy chain

<400> SEQUENCE: 82

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Arg Leu Leu Pro Tyr Trp Gly Gln Gly Thr
            100                 105                 110

Leu Val Thr Val Ser Ser

<210> SEQ ID NO 83
<211> LENGTH: 354
<212> TYPE: DNA
<213> ORGANISM: Artificial Sequence
<220> FEATURE:
<223> OTHER INFORMATION: Anti-TLR4 variable heavy chain

<400> SEQUENCE: 83

```
caggtgcagc ttcaggagtc cggcccagga ctggtgaagc cttcggacac cctgtccctc    60
acctgcgctg tctctggtta ctccatcacc ggtggttata ctggcactg gatacggcag    120
cccccaggga agggactgga gtggatgggg tatatccact acagtggtta cactgacttc    180
aaccccctccc tcaagactcg aatcaccata tcacgtgaca cgtccaagaa ccagttctcc    240
ctgaagctga gctctgtgac cgctgtggac actgcagtgt attactgtgc gagaaaagat    300
agcggcaagt ggttgcctta ctggggccaa gggactctgg tcactgtctc ttcc           354
```

<210> SEQ ID NO 84
<211> LENGTH: 118
<212> TYPE: PRT
<213> ORGANISM: Artificial Sequence
<220> FEATURE:
<223> OTHER INFORMATION: Anti-TLR4 variable heavy chain

<400> SEQUENCE: 84

```
Gln Val Gln Leu Gln Glu Ser Gly Pro Gly Leu Val Lys Pro Ser Asp
1               5                   10                  15
Thr Leu Ser Leu Thr Cys Ala Val Ser Gly Tyr Ser Ile Thr Gly Gly
            20                  25                  30
Tyr Ser Trp His Trp Ile Arg Gln Pro Pro Gly Lys Gly Leu Glu Trp
        35                  40                  45
Met Gly Tyr Ile His Tyr Ser Gly Tyr Thr Asp Phe Asn Pro Ser Leu
    50                  55                  60
Lys Thr Arg Ile Thr Ile Ser Arg Asp Thr Ser Lys Asn Gln Phe Ser
65                  70                  75                  80
Leu Lys Leu Ser Ser Val Thr Ala Val Asp Thr Ala Val Tyr Tyr Cys
                85                  90                  95
Ala Arg Lys Asp Ser Gly Lys Trp Leu Pro Tyr Trp Gly Gln Gly Thr
            100                 105                 110
Leu Val Thr Val Ser Ser
        115
```

<210> SEQ ID NO 85
<211> LENGTH: 354
<212> TYPE: DNA
<213> ORGANISM: Artificial Sequence
<220> FEATURE:
<223> OTHER INFORMATION: Anti-TLR4 variable heavy chain

<400> SEQUENCE: 85

```
caggtgcagc ttcaggagtc cggcccagga ctggtgaagc cttcggacac cctgtccctc    60
acctgcgctg tctctggtta ctccatcacc ggtggttata ctggcactg gatacggcag    120
cccccaggga agggactgga gtggatgggg tatatccact acagtggtta cactgacttc    180
aaccccctccc tcaagactcg aatcaccata tcacgtgaca cgtccaagaa ccagttctcc    240
ctgaagctga gctctgtgac cgctgtggac actgcagtgt attactgtgc gagaaaagat    300
agcgggcacc tcatgcctta ctggggccaa gggactctgg tcactgtctc ttcc           354
```

-continued

<210> SEQ ID NO 86
<211> LENGTH: 118
<212> TYPE: PRT
<213> ORGANISM: Artificial Sequence
<220> FEATURE:
<223> OTHER INFORMATION: Anti-TLR4 variable heavy chain

<400> SEQUENCE: 86

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly His Leu Met Pro Tyr Trp Gly Gln Gly Thr
            100                 105                 110

Leu Val Thr Val Ser Ser
        115

<210> SEQ ID NO 87
<211> LENGTH: 354
<212> TYPE: DNA
<213> ORGANISM: Artificial Sequence
<220> FEATURE:
<223> OTHER INFORMATION: Anti-TLR4 variable heavy chain

<400> SEQUENCE: 87
caggtgcagc ttcaggagtc cggcccagga ctggtgaagc cttcggacac cctgtccctc      60
acctgcgctg tctctggtta ctccatcacc ggtggttata gctggcactg gatacgcag     120 cccccaggga agggactgga gtggatgggg tatatccact acagtggtta cactgacttc    180 aaccccctccc tcaagactcg aatcaccata tcacgtgaca cgtccaagaa ccagttctcc   240
ctgaagctga gctctgtgac cgctgtggac actgcagtgt attactgtgc gagaaaagat    300
tccgggcaca actacccta ctggggccaa gggactctgg tcactgtctc ttcc            354

<210> SEQ ID NO 88
<211> LENGTH: 118
<212> TYPE: PRT
<213> ORGANISM: Artificial Sequence
<220> FEATURE:
<223> OTHER INFORMATION: Anti-TLR4 variable heavy chain

<400> SEQUENCE: 88

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

```
Lys Thr Arg Ile Thr Ile Ser Arg Asp Thr Ser Lys Asn Gln Phe Ser
 65                  70                  75                  80

Leu Lys Leu Ser Ser Val Thr Ala Val Asp Thr Ala Val Tyr Tyr Cys
                 85                  90                  95

Ala Arg Lys Asp Ser Gly His Asn Tyr Pro Tyr Trp Gly Gln Gly Thr
            100                 105                 110

Leu Val Thr Val Ser Ser
        115

<210> SEQ ID NO 89
<211> LENGTH: 354
<212> TYPE: DNA
<213> ORGANISM: Artificial Sequence
<220> FEATURE:
<223> OTHER INFORMATION: Anti-TLR4 variable heavy chain

<400> SEQUENCE: 89
caggtgcagc ttcaggagtc cggcccagga ctggtgaagc cttcggacac cctgtccctc      60
acctgcgctg tctctggtta ctccatcacc ggtggttata gctggcactg gatacggcag     120
cccccaggga agggactgga gtggatgggg tatatccact acagtggtta cactgacttc     180 aaccccctccc tcaagactcg aatcaccata tcacgtgaca cgtccaagaa ccagttctcc    240
ctgaagctga gctctgtgac cgctgtggac actgcagtgt attactgtgc gagaaaagat    300
agcggcaaga acttccctta ctggggccaa gggactctgg tcactgtctc ttcc          354

<210> SEQ ID NO 90
<211> LENGTH: 118
<212> TYPE: PRT
<213> ORGANISM: Artificial Sequence
<220> FEATURE:
<223> OTHER INFORMATION: Anti-TLR4 variable heavy chain

<400> SEQUENCE: 90

Gln Val Gln Leu Gln Glu Ser Gly Pro Gly Leu Val Lys Pro Ser Asp
 1               5                  10                  15

Thr Leu Ser Leu Thr Cys Ala Val Ser Gly Tyr Ser Ile Thr Gly Gly
                 20                  25                  30

Tyr Ser Trp His Trp Ile Arg Gln Pro Pro Gly Lys Gly Leu Glu Trp
             35                  40                  45

Met Gly Tyr Ile His Tyr Ser Gly Tyr Thr Asp Phe Asn Pro Ser Leu
     50                  55                  60

Lys Thr Arg Ile Thr Ile Ser Arg Asp Thr Ser Lys Asn Gln Phe Ser
 65                  70                  75                  80

Leu Lys Leu Ser Ser Val Thr Ala Val Asp Thr Ala Val Tyr Tyr Cys
                 85                  90                  95

Ala Arg Lys Asp Ser Gly Lys Asn Phe Pro Tyr Trp Gly Gln Gly Thr
            100                 105                 110

Leu Val Thr Val Ser Ser
        115

<210> SEQ ID NO 91
<211> LENGTH: 354
<212> TYPE: DNA
<213> ORGANISM: Artificial Sequence
<220> FEATURE:
<223> OTHER INFORMATION: Anti-TLR4 variable heavy chain

<400> SEQUENCE: 91
caggtgcagc ttcaggagtc cggcccagga ctggtgaagc cttcggacac cctgtccctc      60
```

```
acctgcgctg tctctggtta ctccatcacc ggtggttata gctggcactg gatacggcag    120
cccccaggga agggactgga gtggatgggg tatatccact acagtggtta cactgacttc    180
aacccctccc tcaagactcg aatcaccata tcacgtgaca cgtccaagaa ccagttctcc    240
ctgaagctga gctctgtgac cgctgtggac actgcagtgt attactgtgc gagaaaagat    300
agcggccagt tgttccctta ctggggccaa gggactctgg tcactgtctc ttcc          354
```

```
<210> SEQ ID NO 92
<211> LENGTH: 118
<212> TYPE: PRT
<213> ORGANISM: Artificial Sequence
<220> FEATURE:
<223> OTHER INFORMATION: Anti-TLR4 variable heavy chain

<400> SEQUENCE: 92
```

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Gln Leu Phe Pro Tyr Trp Gly Gln Gly Thr
            100                 105                 110

Leu Val Thr Val Ser Ser
        115
```

```
<210> SEQ ID NO 93
<211> LENGTH: 354
<212> TYPE: DNA
<213> ORGANISM: Artificial Sequence
<220> FEATURE:
<223> OTHER INFORMATION: Anti-TLR4 variable heavy chain

<400> SEQUENCE: 93
```

```
caggtgcagc ttcaggagtc cggcccagga ctggtgaagc cttcggacac cctgtccctc     60
acctgcgctg tctctggtta ctccatcacc ggtggttata gctggcactg gatacggcag    120
cccccaggga agggactgga gtggatgggg tatatccact acagtggtta cactgacttc    180
aacccctccc tcaagactcg aatcaccata tcacgtgaca cgtccaagaa ccagttctcc    240
ctgaagctga gctctgtgac cgctgtggac actgcagtgt attactgtgc gagaaaagat    300
agcggccaca acttgcctta ctggggccaa gggactctgg tcactgtctc ttcc          354
```

```
<210> SEQ ID NO 94
<211> LENGTH: 118
<212> TYPE: PRT
<213> ORGANISM: Artificial Sequence
<220> FEATURE:
<223> OTHER INFORMATION: Anti-TLR4 variable heavy chain

<400> SEQUENCE: 94
```

```
Gln Val Gln Leu Gln Glu Ser Gly Pro Gly Leu Val Lys Pro Ser Asp
1               5                   10                  15
```

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
            35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly His Asn Leu Pro Tyr Trp Gly Gln Gly Thr
            100                 105                 110

Leu Val Thr Val Ser Ser
            115

<210> SEQ ID NO 95
<211> LENGTH: 354
<212> TYPE: DNA
<213> ORGANISM: Artificial Sequence
<220> FEATURE:
<223> OTHER INFORMATION: Anti-TLR4 variable heavy chain

<400> SEQUENCE: 95
caggtgcagc ttcaggagtc cggcccagga ctggtgaagc cttcggacac cctgtccctc      60
acctgcgctg tctctggtta ctccatcacc ggtggttata gctggcactg gatacggcag     120
cccccaggga agggactgga gtggatgggg tatatcccact acagtggtta cactgacttc    180
aacccctccc tcaagactcg aatcaccata tcacgtgaca cgtccaagaa ccagttctcc     240
ctgaagctga gctctgtgac cgctgtggac actgcagtgt attactgtgc gagaaaagat     300
tcgggcgact acttccctta ctggggccaa gggactctgg tcactgtctc ttcc           354

<210> SEQ ID NO 96
<211> LENGTH: 118
<212> TYPE: PRT
<213> ORGANISM: Artificial Sequence
<220> FEATURE:
<223> OTHER INFORMATION: Anti-TLR4 variable heavy chain

<400> SEQUENCE: 96

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
            35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asp Tyr Phe Pro Tyr Trp Gly Gln Gly Thr
            100                 105                 110

Leu Val Thr Val Ser Ser
            115

<210> SEQ ID NO 97
<211> LENGTH: 354
<212> TYPE: DNA
<213> ORGANISM: Artificial Sequence
<220> FEATURE:
<223> OTHER INFORMATION: Anti-TLR4 variable heavy chain

<400> SEQUENCE: 97

```
caggtgcagc ttcaggagtc cggcccagga ctggtgaagc cttcggacac cctgtccctc      60
acctgcgctg tctctggtta ctccatcacc ggtggttata gctggcactg gatacggcag     120
cccccaggga agggactgga gtggatgggg tatatccact acagtggtta cactgacttc     180
aacccctccc tcaagactcg aatcaccata tcacgtgaca cgtccaagaa ccagttctcc     240
ctgaagctga gctctgtgac cgctgtggac actgcagtgt attactgtgc gagaaaagat     300
tccgggcggt actggcctta ctggggccaa gggactctgg tcactgtctc ttcc           354
```

<210> SEQ ID NO 98
<211> LENGTH: 118
<212> TYPE: PRT
<213> ORGANISM: Artificial Sequence
<220> FEATURE:
<223> OTHER INFORMATION: Anti-TLR4 variable heavy chain

<400> SEQUENCE: 98

```
Gln Val Gln Leu Gln Glu Ser Gly Pro Gly Leu Val Lys Pro Ser Asp
1               5                   10                  15
Thr Leu Ser Leu Thr Cys Ala Val Ser Gly Tyr Ser Ile Thr Gly Gly
            20                  25                  30
Tyr Ser Trp His Trp Ile Arg Gln Pro Pro Gly Lys Gly Leu Glu Trp
        35                  40                  45
Met Gly Tyr Ile His Tyr Ser Gly Tyr Thr Asp Phe Asn Pro Ser Leu
    50                  55                  60
Lys Thr Arg Ile Thr Ile Ser Arg Asp Thr Ser Lys Asn Gln Phe Ser
65                  70                  75                  80
Leu Lys Leu Ser Ser Val Thr Ala Val Asp Thr Ala Val Tyr Tyr Cys
                85                  90                  95
Ala Arg Lys Asp Ser Gly Arg Tyr Trp Pro Tyr Trp Gly Gln Gly Thr
            100                 105                 110
Leu Val Thr Val Ser Ser
        115
```

<210> SEQ ID NO 99
<211> LENGTH: 354
<212> TYPE: DNA
<213> ORGANISM: Artificial Sequence
<220> FEATURE:
<223> OTHER INFORMATION: Anti-TLR4 variable heavy chain

<400> SEQUENCE: 99

```
caggtgcagc ttcaggagtc cggcccagga ctggtgaagc cttcggacac cctgtccctc      60
acctgcgctg tctctggttt cccgatccgc tacgggtata gctggcactg gatacggcag     120
cccccaggga agggactgga gtggatgggg tatatccact acagtggtta cactgacttc     180
aacccctccc tcaagactcg aatcaccata tcacgtgaca cgtccaagaa ccagttctcc     240
ctgaagctga gctctgtgac cgctgtggac actgcagtgt attactgtgc gagaaaagat     300
tcgggcaact acttcccttcg ctggggccaa gggactctgg tcactgtctc ttcc           354
```

<210> SEQ ID NO 100

<211> LENGTH: 118
<212> TYPE: PRT
<213> ORGANISM: Artificial Sequence
<220> FEATURE:
<223> OTHER INFORMATION: Anti-TLR4 variable heavy chain

<400> SEQUENCE: 100

Gln Val Gln Leu Gln Glu Ser Gly Pro Gly Leu Val Lys Pro Ser Asp
1               5                   10                  15

Thr Leu Ser Leu Thr Cys Ala Val Ser Gly Phe Pro Ile Arg Tyr Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser
        115

<210> SEQ ID NO 101
<211> LENGTH: 354
<212> TYPE: DNA
<213> ORGANISM: Artificial Sequence
<220> FEATURE:
<223> OTHER INFORMATION: Anti-TLR4 variable heavy chain

<400> SEQUENCE: 101
caggtgcagc ttcaggagtc cggcccagga ctggtgaagc cttcggacac cctgtccctc      60
acctgcgctg tctctggtta cccgatccgg ttcggctata gctggcactg gatacgcag     120
cccccaggga agggactgga gtggatgggg tatatccact acagtggtta cactgacttc    180
aaccctcccc tcaagactcg aatcaccata tcacgtgaca cgtccaagaa ccagttctcc    240
ctgaagctga gctctgtgac cgctgtggac actgcagtgt attactgtgc gagaaaagat    300
tcgggcaact acttccctta ctggggccaa gggactctgg tcactgtctc ttcc          354

<210> SEQ ID NO 102
<211> LENGTH: 118
<212> TYPE: PRT
<213> ORGANISM: Artificial Sequence
<220> FEATURE:
<223> OTHER INFORMATION: Anti-TLR4 variable heavy chain

<400> SEQUENCE: 102

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Pro Ile Arg Phe Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

```
Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser
        115

<210> SEQ ID NO 103
<211> LENGTH: 354
<212> TYPE: DNA
<213> ORGANISM: Artificial Sequence
<220> FEATURE:
<223> OTHER INFORMATION: Anti-TLR4 variable heavy chain

<400> SEQUENCE: 103
caggtgcagc ttcaggagtc cggcccagga ctggtgaagc cttcggacac cctgtccctc      60
acctgcgctg tctctggtta ccccatccgg cacgggtaca gctggcactg gatacggcag     120
cccccaggga agggactgga gtggatgggg tatatccact acagtggtta cactgacttc     180
aacccctccc tcaagactcg aatcaccata tcacgtgaca cgtccaagaa ccagttctcc     240
ctgaagctga gctctgtgac cgctgtggac actgcagtgt attactgtgc gagaaaagat     300
tcgggcaact acttccctta ctggggccaa gggactctgg tcactgtctc ttcc           354

<210> SEQ ID NO 104
<211> LENGTH: 118
<212> TYPE: PRT
<213> ORGANISM: Artificial Sequence
<220> FEATURE:
<223> OTHER INFORMATION: Anti-TLR4 variable heavy chain

<400> SEQUENCE: 104

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Pro Ile Arg His Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser
        115

<210> SEQ ID NO 105
<211> LENGTH: 354
<212> TYPE: DNA
<213> ORGANISM: Artificial Sequence
<220> FEATURE:
<223> OTHER INFORMATION: Anti-TLR4 variable heavy chain

<400> SEQUENCE: 105
caggtgcagc ttcaggagtc cggcccagga ctggtgaagc cttcggacac cctgtccctc      60
acctgcgctg tctctggttt cccgatcggc caggggtata gctggcactg gatacggcag     120
```

```
cccccaggga agggactgga gtggatgggg tatatccact acagtggtta cactgacttc    180
aacccctccc tcaagactcg aatcaccata tcacgtgaca cgtccaagaa ccagttctcc    240
ctgaagctga gctctgtgac cgctgtggac actgcagtgt attactgtgc gagaaaagat    300
tcgggcaact acttcccttta ctggggccaa gggactctgg tcactgtctc ttcc         354
```

<210> SEQ ID NO 106
<211> LENGTH: 118
<212> TYPE: PRT
<213> ORGANISM: Artificial Sequence
<220> FEATURE:
<223> OTHER INFORMATION: Anti-TLR4 variable heavy chain

<400> SEQUENCE: 106

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Phe Pro Ile Gly Gln Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser
        115
```

<210> SEQ ID NO 107
<211> LENGTH: 363
<212> TYPE: DNA
<213> ORGANISM: Artificial Sequence
<220> FEATURE:
<223> OTHER INFORMATION: Anti-TLR4 variable heavy chain

<400> SEQUENCE: 107

```
caggtgcagc ttcaggagtc cggcccagga ctggtgaagc cttcggacac cctgtccctc    60
acctgcgctg tctctggtta cccgatctgg ggggctata gctggcactg gatacggcag   120
cccccaggga agggactgga gtggatgggg tatatccact acagtggtta cactgacttc   180
aacccctccc tcaagactcg aatcaccata tcacgtgaca cgtccaagaa ccagttctcc   240
ctgaagctga gctctgtgac cgctgtggac actgcagtgt attactgtgc gagaaaagat   300
tcgggcaact acttcccttta ctggggccaa gggactctgg tcactgtctc ttccgcctcc   360
acc                                                                 363
```

<210> SEQ ID NO 108
<211> LENGTH: 118
<212> TYPE: PRT
<213> ORGANISM: Artificial Sequence
<220> FEATURE:
<223> OTHER INFORMATION: Anti-TLR4 variable heavy chain

<400> SEQUENCE: 108

```
Gln Val Gln Leu Gln Glu Ser Gly Pro Gly Leu Val Lys Pro Ser Asp
1               5                   10                  15
```

```
Thr Leu Ser Leu Thr Cys Ala Val Ser Gly Tyr Pro Ile Trp Gly Gly
        20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
 50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser
        115

<210> SEQ ID NO 109
<211> LENGTH: 354
<212> TYPE: DNA
<213> ORGANISM: Artificial Sequence
<220> FEATURE:
<223> OTHER INFORMATION: Anti-TLR4 variable heavy chain

<400> SEQUENCE: 109
caggtgcagc ttcaggagtc cggcccagga ctggtgaagc cttcggacac cctgtccctc      60
acctgcgctg tctctggtta ccccatcggc ggcggctata gctggcactg gatacggcag     120
cccccaggga agggactgga gtggatgggg tatatccact acagtggtta cactgacttc     180
aaccccctcc tcaagactcg aatcaccata tcacgtgaca cgtccaagaa ccagttctcc     240
ctgaagctga gctctgtgac cgctgtggac actgcagtgt attactgtgc gagaaaagat     300
tcgggcaact acttccctta ctggggccaa gggactctgg tcactgtctc ttcc           354

<210> SEQ ID NO 110
<211> LENGTH: 118
<212> TYPE: PRT
<213> ORGANISM: Artificial Sequence
<220> FEATURE:
<223> OTHER INFORMATION: Anti-TLR4 variable heavy chain

<400> SEQUENCE: 110

Gln Val Gln Leu Gln Glu Ser Gly Pro Gly Leu Val Lys Pro Ser Asp
 1               5                  10                  15

Thr Leu Ser Leu Thr Cys Ala Val Ser Gly Tyr Pro Ile Gly Gly Gly
        20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
 50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser
        115

<210> SEQ ID NO 111
```

-continued

```
<211> LENGTH: 321
<212> TYPE: DNA
<213> ORGANISM: Artificial Sequence
<220> FEATURE:
<223> OTHER INFORMATION: Anti-TLR4 variable light chain

<400> SEQUENCE: 111
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag gggaacgact cccggtgac tttcggcgga     300 gggaccaagg tggagatcaa a                                               321

<210> SEQ ID NO 112
<211> LENGTH: 107
<212> TYPE: PRT
<213> ORGANISM: Artificial Sequence
<220> FEATURE:
<223> OTHER INFORMATION: Anti-TLR4 variable light chain

<400> SEQUENCE: 112

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly Asn Asp Phe Pro Val
                85                  90                  95

Thr Phe Gly Gly Gly Thr Lys Val Glu Ile Lys
            100                 105

<210> SEQ ID NO 113
<211> LENGTH: 321
<212> TYPE: DNA
<213> ORGANISM: Artificial Sequence
<220> FEATURE:
<223> OTHER INFORMATION: Anti-TLR4 variable light chain

<400> SEQUENCE: 113
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag gggtacgacg agccgttcac tttcggcgga     300
gggaccaagg tggagatcaa a                                               321

<210> SEQ ID NO 114
<211> LENGTH: 107
<212> TYPE: PRT
<213> ORGANISM: Artificial Sequence
<220> FEATURE:
```

<223> OTHER INFORMATION: Anti-TLR4 variable light chain

<400> SEQUENCE: 114

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly Tyr Asp Glu Pro Phe
                85                  90                  95

Thr Phe Gly Gly Gly Thr Lys Val Glu Ile Lys
            100                 105
```

<210> SEQ ID NO 115
<211> LENGTH: 321
<212> TYPE: DNA
<213> ORGANISM: Artificial Sequence
<220> FEATURE:
<223> OTHER INFORMATION: Anti-TLR4 variable light chain

<400> SEQUENCE: 115

```
gaaattgtgt tgacgcagtc tccagacttt cagtctgtga ctccaaagga aaaagtcacc     60
atcacctgca gggccagtca gagtatcagc gaccacttac actggtacca acagaaacct    120
gatcagtctc ccaagctcct catcaaatat gcttcccatg ccatttctgg ggtcccatcg    180
aggttcagtg gcagtgggtc tgggacagac ttcactctca ccatcaatag cctagaggct    240
gaagatgctg caacgtatta ctgtcagcag ggctacgact cccgttgac tttcggcgga    300
gggaccaagg tggagatcaa a                                              321
```

<210> SEQ ID NO 116
<211> LENGTH: 107
<212> TYPE: PRT
<213> ORGANISM: Artificial Sequence
<220> FEATURE:
<223> OTHER INFORMATION: Anti-TLR4 variable light chain

<400> SEQUENCE: 116

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly Tyr Asp Phe Pro Leu
                85                  90                  95

Thr Phe Gly Gly Gly Thr Lys Val Glu Ile Lys
            100                 105
```

```
<210> SEQ ID NO 117
<211> LENGTH: 321
<212> TYPE: DNA
<213> ORGANISM: Artificial Sequence
<220> FEATURE:
<223> OTHER INFORMATION: Anti-TLR4 variable light chain

<400> SEQUENCE: 117
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag ggctacgact acccgctcac tttcggcgga     300
gggaccaagg tggagatcaa a                                               321

<210> SEQ ID NO 118
<211> LENGTH: 107
<212> TYPE: PRT
<213> ORGANISM: Artificial Sequence
<220> FEATURE:
<223> OTHER INFORMATION: Anti-TLR4 variable light chain

<400> SEQUENCE: 118

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly Tyr Asp Tyr Pro Leu
                85                  90                  95

Thr Phe Gly Gly Gly Thr Lys Val Glu Ile Lys
            100                 105

<210> SEQ ID NO 119
<211> LENGTH: 321
<212> TYPE: DNA
<213> ORGANISM: Artificial Sequence
<220> FEATURE:
<223> OTHER INFORMATION: Anti-TLR4 variable light chain

<400> SEQUENCE: 119
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag ggctacgagt cccgttgac tttcggcgga     300 gggaccaagg tggagatcaa a                                               321

<210> SEQ ID NO 120
<211> LENGTH: 107
<212> TYPE: PRT
<213> ORGANISM: Artificial Sequence
```

```
<220> FEATURE:
<223> OTHER INFORMATION: Anti-TLR4 variable light chain

<400> SEQUENCE: 120

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly Tyr Glu Phe Pro Leu
                85                  90                  95

Thr Phe Gly Gly Gly Thr Lys Val Glu Ile Lys
            100                 105

<210> SEQ ID NO 121
<211> LENGTH: 321
<212> TYPE: DNA
<213> ORGANISM: Artificial Sequence
<220> FEATURE:
<223> OTHER INFORMATION: Anti-TLR4 variable light chain

<400> SEQUENCE: 121
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag gggaacgact tcccggtgac tttcggcgga     300
gggaccaagg tggagatcaa a                                                321

<210> SEQ ID NO 122
<211> LENGTH: 107
<212> TYPE: PRT
<213> ORGANISM: Artificial Sequence
<220> FEATURE:
<223> OTHER INFORMATION: Anti-TLR4 variable light chain

<400> SEQUENCE: 122

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly Asn Asp Phe Pro Val
                85                  90                  95

Thr Phe Gly Gly Gly Thr Lys Val Glu Ile Lys
            100                 105
```

<210> SEQ ID NO 123
<211> LENGTH: 321
<212> TYPE: DNA
<213> ORGANISM: Artificial Sequence
<220> FEATURE:
<223> OTHER INFORMATION: Anti-TLR4 variable light chain

<400> SEQUENCE: 123

```
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag ggctacgact cccgttgac tttcggcgga      300 gggaccaagg tggagatcaa a                                               321
```

<210> SEQ ID NO 124
<211> LENGTH: 107
<212> TYPE: PRT
<213> ORGANISM: Artificial Sequence
<220> FEATURE:
<223> OTHER INFORMATION: Anti-TLR4 variable light chain

<400> SEQUENCE: 124

```
Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Ser Ile Ser Asp His
             20                  25                  30

Leu His Trp Tyr Gln Gln Lys Pro Asp Gln Ser Pro Lys Leu Leu Ile
         35                  40                  45

Lys Tyr Ala Ser His Ala Ile Ser Gly Val Pro Ser Arg Phe Ser Gly
     50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Gly Tyr Asp Phe Pro Leu
                 85                  90                  95

Thr Phe Gly Gly Gly Thr Lys Val Glu Ile Lys
            100                 105
```

<210> SEQ ID NO 125
<211> LENGTH: 321
<212> TYPE: DNA
<213> ORGANISM: Artificial Sequence
<220> FEATURE:
<223> OTHER INFORMATION: Anti-TLR4 variable light chain

<400> SEQUENCE: 125

```
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag ggctacgact acccgctcac tttcggcgga    300
gggaccaagg tggagatcaa a                                              321
```

<210> SEQ ID NO 126
<211> LENGTH: 107
<212> TYPE: PRT

<213> ORGANISM: Artificial Sequence
<220> FEATURE:
<223> OTHER INFORMATION: Anti-TLR4 variable light chain

<400> SEQUENCE: 126

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly Tyr Asp Tyr Pro Leu
                85                  90                  95

Thr Phe Gly Gly Gly Thr Lys Val Glu Ile Lys
            100                 105
```

<210> SEQ ID NO 127
<211> LENGTH: 321
<212> TYPE: DNA
<213> ORGANISM: Artificial Sequence
<220> FEATURE:
<223> OTHER INFORMATION: Anti-TLR4 variable light chain

<400> SEQUENCE: 127

```
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag ggctacgagt tcccgttgac tttcggcgga     300
gggaccaagg tggagatcaa a                                               321
```

<210> SEQ ID NO 128
<211> LENGTH: 107
<212> TYPE: PRT
<213> ORGANISM: Artificial Sequence
<220> FEATURE:
<223> OTHER INFORMATION: Anti-TLR4 variable light chain

<400> SEQUENCE: 128

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly Tyr Glu Phe Pro Leu
                85                  90                  95

Thr Phe Gly Gly Gly Thr Lys Val Glu Ile Lys
            100                 105
```

<210> SEQ ID NO 129
<211> LENGTH: 1398
<212> TYPE: DNA
<213> ORGANISM: Artificial Sequence
<220> FEATURE:
<223> OTHER INFORMATION: Anti-TLR4 heavy chain

<400> SEQUENCE: 129

```
atggaatgga gctgggtctt tctcttcttc ctgtcagtaa ctacaggtgt ccaccaggtg      60
cagcttcagg agtccggccc aggactggtg aagccttcgg acaccctgtc cctcacctgc     120
gctgtctctg gttactccat caccggtggt tatagctggc actggatacg gcagccccca     180
gggaagggac tggagtggat ggggtatatc cactacagtg gttacactga cttcaacccc     240
tccctcaaga ctcgaatcac catatcacgt gacacgtcca agaaccagtt ctccctgaag     300
ctgagctctg tgaccgctgt ggacactgca gtgtattact gtgcgagaaa agatccgtcc     360
gacgcctttc cttactgggg ccaagggact ctggtcactg tctcttccgc ctccaccaag     420
ggcccatcgg tcttccccct ggcaccctcc tccaagagca cctctggggg cacagcggcc     480
ctgggctgcc tggtcaagga ctacttcccc gaaccggtga cagtctcgtg gaactcagga     540
gccctgacca gcggcgtgca caccttcccg gctgtcctac agtcctcagg actctactcc     600
ctcagcagcg tggtgactgt gccctccagc agcttgggca cccagaccta catctgcaac     660
gtgaatcaca agcccagcaa caccaaggtg gacaagagag ttgagcccaa atcttgtgac     720
aaaactcaca catgcccacc gtgcccagca cctgaactcc tggggggacc gtcagtcttc     780
ctcttccccc caaaacccaa ggacaccctc atgatctccc ggacccctga ggtcacatgc     840
gtggtggtgg acgtgagcca cgaagaccct gaggtcaagt tcaactggta cgtggacggc     900
gtggaggtgc ataatgccaa gacaaagccg cgggaggagc agtacaacag cacgtaccgt     960
gtggtcagcg tcctcaccgt cctgcaccag gactggctga atggcaagga gtacaagtgc    1020
aaggtctcca acaaagccct cccagccccc atcgagaaaa ccatctccaa agccaaaggg    1080
cagccccgag aaccacaggt gtataccctg cccccatctc gggaggagat gaccaagaac    1140
caggtcagcc tgacttgcct ggtcaaaggc ttctatccca gcgacatcgc cgtggagtgg    1200
gagagcaacg ggcagccgga gaacaactac aagaccacgc ctcccgtgct ggactccgac    1260
ggctccttct tcctctatag caagctcacc gtggacaagt ccaggtggca gcaggggaac    1320
gtcttctcat gctccgtgat gcatgaggct ctgcacaacc actacacgca gaagagcctc    1380
tccctgtctc cgggttaa                                                  1398
```

<210> SEQ ID NO 130
<211> LENGTH: 447
<212> TYPE: PRT
<213> ORGANISM: Artificial Sequence
<220> FEATURE:
<223> OTHER INFORMATION: Anti-TLR4 heavy chain

<400> SEQUENCE: 130

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
```

```
                50             55             60
Lys Thr Arg Ile Thr Ile Ser Arg Asp Thr Ser Lys Asn Gln Phe Ser
 65                      70                     75                     80

Leu Lys Leu Ser Ser Val Thr Ala Val Asp Thr Ala Val Tyr Tyr Cys
                     85                     90                     95

Ala Arg Lys Asp Ser Gly Asn Tyr Phe Pro Tyr Trp Gly Gln Gly Thr
                    100                    105                    110

Leu Val Thr Val Ser Ser Ala Ser Thr Lys Gly Pro Ser Val Phe Pro
                    115                    120                    125

Leu Ala Pro Ser Ser Lys Ser Thr Ser Gly Gly Thr Ala Ala Leu Gly
            130                    135                    140

Cys Leu Val Lys Asp Tyr Phe Pro Glu Pro Val Thr Val Ser Trp Asn
145                    150                    155                    160

Ser Gly Ala Leu Thr Ser Gly Val His Thr Phe Pro Ala Val Leu Gln
                    165                    170                    175

Ser Ser Gly Leu Tyr Ser Leu Ser Ser Val Val Thr Val Pro Ser Ser
                    180                    185                    190

Ser Leu Gly Thr Gln Thr Tyr Ile Cys Asn Val Asn His Lys Pro Ser
            195                    200                    205

Asn Thr Lys Val Asp Lys Arg Val Glu Pro Lys Ser Cys Asp Lys Thr
210                    215                    220

His Thr Cys Pro Pro Cys Pro Ala Pro Glu Leu Leu Gly Gly Pro Ser
225                    230                    235                    240

Val Phe Leu Phe Pro Pro Lys Pro Lys Asp Thr Leu Met Ile Ser Arg
                    245                    250                    255

Thr Pro Glu Val Thr Cys Val Val Val Asp Val Ser His Glu Asp Pro
                    260                    265                    270

Glu Val Lys Phe Asn Trp Tyr Val Asp Gly Val Glu Val His Asn Ala
            275                    280                    285

Lys Thr Lys Pro Arg Glu Glu Gln Tyr Asn Ser Thr Tyr Arg Val Val
            290                    295                    300

Ser Val Leu Thr Val Leu His Gln Asp Trp Leu Asn Gly Lys Glu Tyr
305                    310                    315                    320

Lys Cys Lys Val Ser Asn Lys Ala Leu Pro Ala Pro Ile Glu Lys Thr
                    325                    330                    335

Ile Ser Lys Ala Lys Gly Gln Pro Arg Glu Pro Gln Val Tyr Thr Leu
                    340                    345                    350

Pro Pro Ser Arg Glu Glu Met Thr Lys Asn Gln Val Ser Leu Thr Cys
            355                    360                    365

Leu Val Lys Gly Phe Tyr Pro Ser Asp Ile Ala Val Glu Trp Glu Ser
370                    375                    380

Asn Gly Gln Pro Glu Asn Asn Tyr Lys Thr Thr Pro Pro Val Leu Asp
385                    390                    395                    400

Ser Asp Gly Ser Phe Phe Leu Tyr Ser Lys Leu Thr Val Asp Lys Ser
                    405                    410                    415

Arg Trp Gln Gln Gly Asn Val Phe Ser Cys Ser Val Met His Glu Ala
                    420                    425                    430

Leu His Asn His Tyr Thr Gln Lys Ser Leu Ser Leu Ser Pro Gly
            435                    440                    445

<210> SEQ ID NO 131
<211> LENGTH: 705
<212> TYPE: DNA
<213> ORGANISM: Artificial Sequence
```

<220> FEATURE:
<223> OTHER INFORMATION: Anti-TLR4 light chain

<400> SEQUENCE: 131

```
atgagtgtgc ccactcaggt cctggggttg ctgctgctgt ggcttacaga tgccagatgt      60
gaaattgtgt tgacgcagtc tccagacttt cagtctgtga ctccaaagga aaaagtcacc     120
atcacctgca gggccagtca gagtatcagc gaccacttac actggtacca acagaaacct     180
gatcagtctc ccaagctcct catcaaatat gcttcccatg ccatttctgg ggtcccatcg     240
aggttcagtg gcagtgggtc tgggacagac ttcactctca ccatcaatag cctagaggct     300
gaagatgctg caacgtatta ctgtcagcag ggtcacagtt ttccgctcac tttcggcgga     360
gggaccaagg tggagatcaa acgtacggtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag cacccctgacg    600
ctgagcaaag cagactacga aaacacaaa gtctacgcct gcgaagtcac ccatcagggc      660
ctgagctcgc ccgtcacaaa gagcttcaac aggggagagt gttaa                     705
```

<210> SEQ ID NO 132
<211> LENGTH: 214
<212> TYPE: PRT
<213> ORGANISM: Artificial Sequence
<220> FEATURE:
<223> OTHER INFORMATION: Anti-TLR4 light chain

<400> SEQUENCE: 132

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 133
<211> LENGTH: 1398
<212> TYPE: DNA
<213> ORGANISM: Artificial Sequence
<220> FEATURE:
<223> OTHER INFORMATION: Anti-TLR4 heavy chain

<400> SEQUENCE: 133

```
atggaatgga gctgggtctt tctcttcttc ctgtcagtaa ctacaggtgt ccaccaggtg      60
cagcttcagg agtccggccc aggactggtg aagccttcgg acaccctgtc cctcacctgc     120
gctgtctctg gtttcccgat ccgctacggg tatagctggc actggatacg gcagccccca     180
gggaagggac tggagtggat ggggtatatc cactacagtg gttacactga cttcaacccc     240
tccctcaaga ctcgaatcac catatcacgt gacacgtcca agaaccagtt ctccctgaag     300
ctgagctctg tgaccgctgt ggacactgca gtgtattact gtgcgagaaa agattcgggc     360
aactacttcc cttactgggg ccaagggact ctggtcactg tctcttccgc ctccaccaag     420
ggcccatcgg tcttccccct ggcaccctcc tccaagagca cctctggggg cacagcggcc     480
ctgggctgcc tggtcaagga ctacttcccc gaaccggtga cagtctcgtg gaactcagga     540
gccctgacca gcggcgtgca caccttcccg gctgtcctac agtcctcagg actctactcc     600
ctcagcagcg tggtgactgt gccctccagc agcttgggca cccagaccta catctgcaac     660
gtgaatcaca agcccagcaa caccaaggtg gacaagagag ttgagcccaa atcttgtgac     720
aaaactcaca catgcccacc gtgcccagca cctgaactcc tggggggacc gtcagtcttc     780
ctcttccccc caaaacccaa ggacaccctc atgatctccc ggacccctga ggtcacatgc     840
gtggtggtgg acgtgagcca cgaagaccct gaggtcaagt tcaactggta cgtggacggc     900
gtggaggtgc ataatgccaa gacaaagccg cgggaggagc agtacaacag cacgtaccgt     960
gtggtcagcg tcctcaccgt cctgcaccag gactggctga atggcaagga gtacaagtgc    1020
aaggtctcca acaaagccct cccagccccc atcgagaaaa ccatctccaa agccaaaggg    1080
cagccccgag aaccacaggt gtataccctg cccccatctc gggaggagat gaccaagaac    1140
caggtcagcc tgacttgcct ggtcaaaggc ttctatccca gcgacatcgc cgtggagtgg    1200
gagagcaacg ggcagccgga gaacaactac aagaccacgc ctcccgtgct ggactccgac    1260
ggctccttct tcctctatag caagctcacc gtggacaagt ccaggtggca gcaggggaac    1320
gtcttctcat gctccgtgat gcatgaggct ctgcacaacc actacacgca gaagagcctc    1380
tccctgtctc cgggttaa                                                  1398
```

<210> SEQ ID NO 134
<211> LENGTH: 446
<212> TYPE: PRT
<213> ORGANISM: Artificial Sequence
<220> FEATURE:
<223> OTHER INFORMATION: Anti-TLR4 heavy chain

<400> SEQUENCE: 134

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Phe Pro Ile Arg Tyr Gly
            20                  25                  30

Tyr Ser Trp His Trp Ile Arg Gln Pro Pro Gly Lys Gly Leu Glu Trp
        35                  40                  45
```

```
Met Gly Tyr Ile His Tyr Ser Gly Tyr Thr Asp Phe Asn Pro Leu Lys
 50                  55                  60

Thr Arg Ile Thr Ile Ser Arg Asp Thr Ser Lys Asn Gln Phe Ser Leu
 65                  70                  75                  80

Lys Leu Ser Ser Val Thr Ala Val Asp Thr Ala Val Tyr Tyr Cys Ala
                 85                  90                  95

Arg Lys Asp Ser Gly Asn Tyr Phe Pro Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 135
<211> LENGTH: 705
<212> TYPE: DNA
```

<213> ORGANISM: Artificial Sequence
<220> FEATURE:
<223> OTHER INFORMATION: Anti-TLR4 light chain

<400> SEQUENCE: 135

```
atgagtgtgc ccactcaggt cctggggttg ctgctgctgt ggcttacaga tgccagatgt      60
gaaattgtgt tgacgcagtc tccagacttt cagtctgtga ctccaaagga aaaagtcacc     120
atcacctgca gggccagtca gagtatcagc gaccacttac actggtacca acagaaacct     180
gatcagtctc ccaagctcct catcaaatat gcttcccatg ccatttctgg ggtcccatcg     240
aggttcagtg gcagtgggtc tgggacagac ttcactctca ccatcaatag cctagaggct     300
gaagatgctg caacgtatta ctgtcagcag ggtcacagtt ttccgctcac tttcggcgga     360
gggaccaagg tggagatcaa acgtacggtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga gaaacacaaa gtctacgcct gcgaagtcac ccatcagggc     660
ctgagctcgc ccgtcacaaa gagcttcaac aggggagagt gttaa                     705
```

<210> SEQ ID NO 136
<211> LENGTH: 214
<212> TYPE: PRT
<213> ORGANISM: Artificial Sequence
<220> FEATURE:
<223> OTHER INFORMATION: Anti-TLR4 light chain

<400> SEQUENCE: 136

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210

<210> SEQ ID NO 137
<211> LENGTH: 4
<212> TYPE: PRT
<213> ORGANISM: Artificial Sequence
<220> FEATURE:
<223> OTHER INFORMATION: gamma heavy chain constant region variant
      subsequence

<400> SEQUENCE: 137

Ser Lys Ala Phe
1

<210> SEQ ID NO 138
<211> LENGTH: 9
<212> TYPE: PRT
<213> ORGANISM: Artificial Sequence
<220> FEATURE:
<223> OTHER INFORMATION: Anti-TLR4 VH CDR3 region

<400> SEQUENCE: 138

Lys Asp Pro Ser Asp Gly Phe Pro Tyr
1               5

<210> SEQ ID NO 139
<211> LENGTH: 9
<212> TYPE: PRT
<213> ORGANISM: Artificial Sequence
<220> FEATURE:
<223> OTHER INFORMATION: Anti-TLR4 VL CDR3 region

<400> SEQUENCE: 139

Gln Asn Gly His Ser Phe Pro Leu Thr
1               5
```